(12) United States Patent
Stevens et al.

(10) Patent No.: US 8,435,235 B2
(45) Date of Patent: May 7, 2013

(54) SYSTEMS AND METHODS FOR TREATING HOLLOW ANATOMICAL STRUCTURES

(75) Inventors: Walter J. Stevens, Santa Clara, CA (US); Stephen W. Lee, Sr., San Jose, CA (US); Michael S. Mirizzi, San Jose, CA (US); Hoa D. Nguyen, San Jose, CA (US)

(73) Assignee: Covidien LP, Mansfield, MA (US)

( * ) Notice: Subject to any disclaimer, the term of this patent is extended or adjusted under 35 U.S.C. 154(b) by 903 days.

(21) Appl. No.: 12/110,169

(22) Filed: Apr. 25, 2008

(65) Prior Publication Data

US 2008/0292255 A1 Nov. 27, 2008

Related U.S. Application Data

(60) Provisional application No. 60/914,660, filed on Apr. 27, 2007, provisional application No. 60/986,577, filed on Nov. 8, 2007.

(51) Int. Cl.
*A61B 18/20* (2006.01)

(52) U.S. Cl.
USPC .............................. 606/15; 385/109

(58) Field of Classification Search .................. 606/2–3, 606/7, 10, 13–16; 607/88–92
See application file for complete search history.

(56) References Cited

U.S. PATENT DOCUMENTS

| | | | |
|---|---|---|---|
| 373,399 A | 11/1887 | Hamilton |
| 659,409 A | 10/1900 | Mosher |
| 833,759 A | 10/1906 | Sourwine |
| 985,865 A | 3/1911 | Turner, Jr. |
| 2,671,444 A | 3/1954 | Pease, Jr. |
| 3,230,957 A | 1/1966 | Pease, Jr. |
| 3,301,258 A | 1/1967 | Werner et al. |
| 3,557,794 A | 1/1971 | Van Patten |
| 3,920,021 A | 11/1975 | Hiltebrandt |
| 4,016,886 A | 4/1977 | Doss et al. |
| 4,043,338 A | 8/1977 | Homm et al. |
| 4,119,102 A | 10/1978 | LeVeen |
| 4,154,246 A | 5/1979 | LeVeen |
| 4,312,364 A | 1/1982 | Convert et al. |
| 4,346,715 A | 8/1982 | Gammell |

(Continued)

FOREIGN PATENT DOCUMENTS

| | | |
|---|---|---|
| CN | 1050992 | 5/1991 |
| EP | 0189329 | 7/1986 |

(Continued)

OTHER PUBLICATIONS

International Search Report and Written Opinion in PCT Application No. PCT/US08/061641 dated Jul. 24, 2008 in 4 pages.

(Continued)

*Primary Examiner* — Henry M Johnson, III
(74) *Attorney, Agent, or Firm* — Thomas M. Johnston, Esq.

(57) ABSTRACT

An apparatus for treating a hollow anatomical structure can include a light delivery device. The light delivery device comprises an optical fiber that is located in a lumen of a shaft suitable for insertion into the hollow anatomical structure and has a fiber tip located proximal of a distal end of the shaft during treatment of the hollow anatomical structure. The apparatus can further include a liquid source for providing a liquid flow over the optical fiber at a predetermined liquid flow rate.

26 Claims, 27 Drawing Sheets

U.S. PATENT DOCUMENTS

| | | | |
|---|---|---|---|
| 4,519,390 A | 5/1985 | Horne | |
| 4,522,205 A | 6/1985 | Taylor et al. | |
| 4,564,011 A | 1/1986 | Goldman | |
| 4,643,186 A | 2/1987 | Rosen et al. | |
| 4,648,865 A * | 3/1987 | Aigner | 604/6.09 |
| 4,658,836 A | 4/1987 | Turner | |
| 4,660,571 A | 4/1987 | Hess et al. | |
| 4,664,120 A | 5/1987 | Hess | |
| 4,699,147 A | 10/1987 | Chilson et al. | |
| 4,709,698 A | 12/1987 | Johnston et al. | |
| 4,765,331 A | 8/1988 | Petruzzi et al. | |
| 4,773,413 A | 9/1988 | Hussein et al. | |
| 4,776,349 A | 10/1988 | Nashef et al. | |
| 4,802,650 A * | 2/1989 | Stricker | 251/117 |
| 4,807,620 A | 2/1989 | Strul et al. | |
| 4,823,812 A | 4/1989 | Eshel et al. | |
| 4,862,887 A * | 9/1989 | Weber et al. | 606/15 |
| 4,937,711 A | 6/1990 | Shuen | |
| 4,945,912 A | 8/1990 | Langberg | |
| 4,966,597 A | 10/1990 | Cosman | |
| 4,976,711 A | 12/1990 | Parins et al. | |
| 4,979,948 A | 12/1990 | Geddes et al. | |
| 5,010,894 A | 4/1991 | Edhag | |
| 5,022,399 A | 6/1991 | Biegeleisen | |
| 5,026,366 A | 6/1991 | Leckrone | |
| 5,035,694 A | 7/1991 | Kasprzyk et al. | |
| 5,050,597 A | 9/1991 | Daikuzono | |
| 5,053,033 A | 10/1991 | Clarke | |
| 5,057,106 A | 10/1991 | Kasevich et al. | |
| 5,057,107 A | 10/1991 | Parins et al. | |
| 5,078,717 A | 1/1992 | Parins et al. | |
| 5,098,429 A | 3/1992 | Sterzer | |
| 5,098,431 A | 3/1992 | Rydell | |
| 5,100,388 A | 3/1992 | Behl et al. | |
| 5,117,828 A | 6/1992 | Metzger et al. | |
| 5,122,137 A | 6/1992 | Lennox | |
| 5,152,277 A * | 10/1992 | Honda et al. | 600/116 |
| 5,156,151 A | 10/1992 | Imran | |
| 5,158,560 A | 10/1992 | Sogawa et al. | |
| 5,167,686 A | 12/1992 | Wong | |
| 5,188,602 A | 2/1993 | Nichols | |
| 5,190,517 A | 3/1993 | Zieve et al. | |
| 5,190,538 A | 3/1993 | Hussein et al. | |
| 5,193,549 A | 3/1993 | Bellin et al. | |
| 5,215,103 A | 6/1993 | Desai | |
| 5,242,438 A | 9/1993 | Saadatmanesh et al. | |
| 5,246,436 A | 9/1993 | Rowe | |
| 5,255,678 A | 10/1993 | Deslauriers et al. | |
| 5,257,634 A | 11/1993 | Kroll | |
| 5,257,991 A | 11/1993 | Fletcher et al. | |
| 5,263,493 A | 11/1993 | Avitall | |
| 5,275,610 A | 1/1994 | Eberbach | |
| 5,281,218 A | 1/1994 | Imran | |
| 5,282,845 A | 2/1994 | Bush et al. | |
| 5,293,869 A | 3/1994 | Edwards et al. | |
| 5,304,171 A | 4/1994 | Gregory et al. | |
| 5,312,392 A | 5/1994 | Hofstetter et al. | |
| 5,314,466 A | 5/1994 | Stern et al. | |
| 5,318,024 A | 6/1994 | Kittrell et al. | |
| 5,324,285 A * | 6/1994 | Cannon | 606/15 |
| 5,354,294 A | 10/1994 | Chou | |
| 5,354,324 A | 10/1994 | Gregory | |
| 5,370,677 A | 12/1994 | Rudie et al. | |
| 5,370,678 A | 12/1994 | Edwards et al. | |
| 5,383,917 A | 1/1995 | Desai et al. | |
| 5,397,339 A | 3/1995 | Desai | |
| 5,403,312 A | 4/1995 | Yates et al. | |
| 5,405,322 A | 4/1995 | Lennox et al. | |
| 5,405,346 A | 4/1995 | Grundy et al. | |
| 5,409,000 A | 4/1995 | Imran | |
| 5,411,025 A | 5/1995 | Webster, Jr. | |
| 5,423,815 A | 6/1995 | Fugo | |
| 5,429,130 A | 7/1995 | Goldman | |
| 5,431,649 A | 7/1995 | Mulier et al. | |
| 5,437,660 A | 8/1995 | Johnson et al. | |
| 5,437,664 A | 8/1995 | Cohen et al. | |
| 5,445,608 A | 8/1995 | Chen et al. | |
| 5,445,680 A | 8/1995 | Hamilton | |
| 5,447,529 A | 9/1995 | Marchlinski et al. | |
| 5,449,381 A | 9/1995 | Imran | |
| 5,454,809 A | 10/1995 | Janssen | |
| 5,458,596 A | 10/1995 | Lax et al. | |
| 5,462,545 A | 10/1995 | Wang et al. | |
| 5,465,717 A | 11/1995 | Imran et al. | |
| 5,468,242 A | 11/1995 | Reisberg | |
| 5,472,441 A | 12/1995 | Edwards et al. | |
| 5,486,171 A | 1/1996 | Chou | |
| 5,496,305 A | 3/1996 | Kittrell et al. | |
| 5,496,307 A | 3/1996 | Daikuzono | |
| 5,505,730 A | 4/1996 | Edwards | |
| 5,514,130 A | 5/1996 | Baker | |
| 5,531,739 A | 7/1996 | Trelles | |
| 5,545,161 A | 8/1996 | Imran | |
| 5,562,657 A | 10/1996 | Griffin | |
| 5,571,099 A | 11/1996 | Purcell, Jr. et al. | |
| 5,607,422 A | 3/1997 | Smeets et al. | |
| 5,626,578 A | 5/1997 | Tihon | |
| 5,643,251 A | 7/1997 | Hillsman et al. | |
| 5,681,310 A | 10/1997 | Yuan et al. | |
| 5,693,043 A | 12/1997 | Kittrell et al. | |
| 5,709,224 A | 1/1998 | Behl et al. | |
| 5,746,737 A | 5/1998 | Saadat | |
| 5,766,176 A | 6/1998 | Duncan | |
| 5,772,657 A | 6/1998 | Hmelar et al. | |
| 5,779,698 A | 7/1998 | Clayman et al. | |
| 5,794,628 A | 8/1998 | Dean | |
| 5,810,804 A | 9/1998 | Gough et al. | |
| 5,814,048 A | 9/1998 | Morgan | |
| 5,817,092 A | 10/1998 | Behl | |
| 5,863,290 A | 1/1999 | Gough et al. | |
| 5,868,740 A | 2/1999 | LeVeen et al. | |
| 5,885,278 A | 3/1999 | Fleischman | |
| 5,964,753 A | 10/1999 | Edwards | |
| 6,004,316 A | 12/1999 | Laufer | |
| 6,033,397 A | 3/2000 | Laufer et al. | |
| 6,033,398 A | 3/2000 | Farley et al. | |
| 6,036,687 A | 3/2000 | Laufer et al. | |
| 6,071,277 A | 6/2000 | Farley et al. | |
| 6,071,291 A | 6/2000 | Forst et al. | |
| 6,077,257 A | 6/2000 | Edwards et al. | |
| 6,083,223 A | 7/2000 | Baker | |
| 6,090,105 A | 7/2000 | Zepeda et al. | |
| 6,129,698 A | 10/2000 | Beck | |
| 6,129,721 A | 10/2000 | Kataoka et al. | |
| 6,135,997 A | 10/2000 | Laufer et al. | |
| 6,138,046 A * | 10/2000 | Dalton | 600/476 |
| 6,139,527 A | 10/2000 | Laufer et al. | |
| 6,152,899 A | 11/2000 | Farley et al. | |
| 6,156,032 A | 12/2000 | Lennox | |
| 6,398,780 B1 | 6/2002 | Farley et al. | |
| 6,401,719 B1 | 6/2002 | Farley et al. | |
| 6,517,534 B1 | 2/2003 | McGovern et al. | |
| 6,572,609 B1 * | 6/2003 | Farr et al. | 606/15 |
| 6,613,045 B1 | 9/2003 | Laufer et al. | |
| 6,638,273 B1 | 10/2003 | Farley et al. | |
| 6,652,585 B2 | 11/2003 | Lange | |
| 6,666,858 B2 | 12/2003 | Lafontaine | |
| 6,682,526 B1 | 1/2004 | Jones et al. | |
| 6,689,126 B1 | 2/2004 | Farley et al. | |
| 6,699,239 B1 | 3/2004 | Stiller et al. | |
| 6,769,433 B2 | 8/2004 | Zikorus et al. | |
| 6,800,092 B1 | 10/2004 | Williams et al. | |
| 6,802,838 B2 | 10/2004 | Loeb et al. | |
| 6,805,129 B1 | 10/2004 | Pless et al. | |
| 6,845,193 B2 | 1/2005 | Loeb et al. | |
| 6,911,028 B2 | 6/2005 | Shadduck | |
| 6,969,388 B2 | 11/2005 | Goldman et al. | |
| 6,981,971 B2 | 1/2006 | Caldera et al. | |
| 6,981,972 B1 | 1/2006 | Farley et al. | |
| 7,041,098 B2 | 5/2006 | Farley et al. | |
| 7,137,977 B2 | 11/2006 | Brucker et al. | |
| 7,160,289 B2 | 1/2007 | Cohen | |
| 7,163,533 B2 | 1/2007 | Hobbs et al. | |
| 7,201,748 B2 | 4/2007 | Karino et al. | |
| 7,273,478 B2 | 9/2007 | Appling et al. | |
| 7,396,355 B2 | 7/2008 | Goldman et al. | |
| 7,458,967 B2 | 12/2008 | Appling et al. | |

| | | |
|---|---|---|
| 7,524,316 B2 | 4/2009 | Hennings et al. |
| 2001/0037080 A1 | 11/2001 | Mueller et al. |
| 2002/0068866 A1 | 6/2002 | Zikorus et al. |
| 2002/0123750 A1 | 9/2002 | Eisermann et al. |
| 2003/0078569 A1* | 4/2003 | Caldera et al. .................. 606/15 |
| 2003/0236517 A1 | 12/2003 | Appling |
| 2004/0049175 A1* | 3/2004 | Speck et al. .................... 606/15 |
| 2004/0092913 A1 | 5/2004 | Hennings et al. |
| 2005/0015123 A1 | 1/2005 | Paithankar |
| 2005/0054983 A1* | 3/2005 | Mullen .................... 604/164.02 |
| 2005/0131400 A1 | 6/2005 | Hennings et al. |
| 2005/0215988 A1 | 9/2005 | Altshuler et al. |
| 2005/0259933 A1 | 11/2005 | Temelkuran et al. |
| 2005/0288655 A1 | 12/2005 | Root |
| 2006/0069417 A1 | 3/2006 | Farley et al. |
| 2006/0085054 A1 | 4/2006 | Zikorus et al. |
| 2006/0167442 A1 | 7/2006 | Hebert et al. |
| 2007/0049911 A1 | 3/2007 | Brown |
| 2007/0100329 A1 | 5/2007 | Maglione et al. |
| 2007/0179486 A1 | 8/2007 | Welch et al. |
| 2007/0196414 A1* | 8/2007 | Hammarsten et al. ........ 424/422 |
| 2008/0065058 A1 | 3/2008 | Neuberger |
| 2008/0125705 A1 | 5/2008 | Sato et al. |
| 2008/0188843 A1 | 8/2008 | Appling et al. |
| 2008/0208180 A1 | 8/2008 | Cartier et al. |
| 2008/0287939 A1 | 11/2008 | Appling et al. |
| 2009/0005775 A1 | 1/2009 | Jones et al. |
| 2009/0088695 A1* | 4/2009 | Kapur et al. ............. 604/164.01 |
| 2009/0131924 A1 | 5/2009 | Meyer et al. |
| 2009/0306637 A1 | 12/2009 | Esch et al. |
| 2011/0202047 A1 | 8/2011 | Farley et al. |

FOREIGN PATENT DOCUMENTS

| | | |
|---|---|---|
| EP | 0205851 | 12/1986 |
| EP | 0 441 974 A | 8/1991 |
| EP | 0629382 | 12/1994 |
| EP | 0727184 | 8/1996 |
| EP | 0738501 | 10/1996 |
| WO | WO 90/07303 | 7/1990 |
| WO | WO 92/12681 | 8/1992 |
| WO | WO 93/21846 | 11/1993 |
| WO | WO 94/07446 | 4/1994 |
| WO | WO 94/21170 | 9/1994 |
| WO | WO 95/10322 | 4/1995 |
| WO | WO 95/10978 | 4/1995 |
| WO | WO 95/31142 | 11/1995 |
| WO | WO 96/32885 | 10/1996 |
| WO | WO 97/06739 | 2/1997 |
| WO | WO 97/17892 | 5/1997 |
| WO | WO 98/55072 | 12/1998 |

OTHER PUBLICATIONS

Office Action in U.S. Appl. No. 09/825,741, mailed Mar. 24, 2008.
Office Action in U.S. Appl. No. 09/825,741, mailed Jul. 23, 2008.
Office Action in U.S. Appl. No. 11/222,069, mailed Jun. 3, 2008.
Biegelesian, K., Use of the Venoscope for the Treatment of Varicose Veins, Phelobogie 1989, pp. 419-422.
Brunelle et al., A Bipolar Electrode for Vascular Electrocoagulation with Alternating Current, Technical Notes, Oct. 1980 at 239-40.
Cragg et al., Endovascular Diathermic Vessel Occlusion, Diagnostic Radiology, 144:303-308, Jul. 1982.
Examination Report from European Patent Office (EPO) dated Dec. 2, 2010 for European Patent Application No. 08 746 951.6, filed Apr. 25, 2008.
Gradman, Venoscopic Obliteration of Variceal Tributaries Using Monopolar Electrocautery, Journal of Dermatology Surgery Oncology, 1994, 20, p. 482-485.
Money, Endovascular Electroablation of Peripheral Veins, 22nd Annual Symposium, Current Critical Problems, New Horizons and Techniques in Vascular and Endovascular Surgery (Nov. 1995).
O'Reilly, A Technique of Diathermy Sclerosis of Varicose Veins, The Australian New Zealand Journal of Surgery, vol. 51, No. 4, Aug. 1981, pp. 379-382.
O'Reilly, Endovenous Diathermy Sclerosis as a Unit of the Armamentarium for the Attack on Varicose Veins, The Medical Journal of Australia, Jun. 1, 1974, at 900.
O'Reilly, Endovenous Diathermy Sclerosis of Varicose Veins, The Australian New Zealand Journal of Surgery, vol. 47, No. 3, Jun. 1977, pp. 393-395.
Office Action from the State Intellectual Property Office of the P.R.C (SIPO) for application No. 200880013423, dated Mar. 9, 2011.
Ogawa et al., Electrothrombosis as a Treatment of Cirsoid Angioma in the Face and Scalp and Varicosis of the Leg, Plastic and Reconstructive Surgery, Sep. 1982, vol. 3, at 310-318.
Watts, Endovenous Diathermy Destruction of Internal Saphenous, British Medical Journal, Oct. 7, 1972.
U.S. Appl. No. 11/280,778, filed Nov. 16, 2005, Brian E. Farley, Office Action Oct. 21, 2010, Dec. 11, 2009, Feb. 6, 2009, Notice of Allowance Apr. 4, 2011.
U.S. Appl. No. 13/095,335, filed Apr. 27, 2011, Brian E. Farley, Office Action Aug. 5, 2011.
U.S. Appl. No. 12/126,727, filed May 23, 2008, Christopher S. Jones, Office Action Aug. 9, 2010, Notice of Allowance Jan. 12, 2011.

* cited by examiner

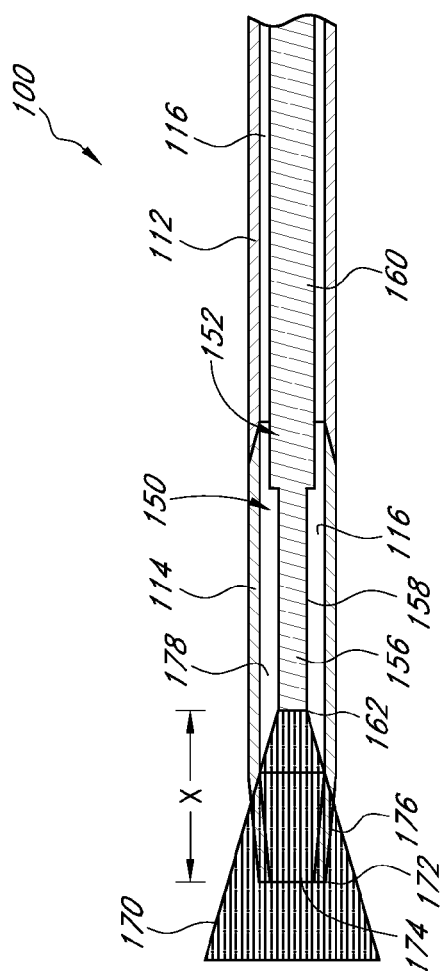
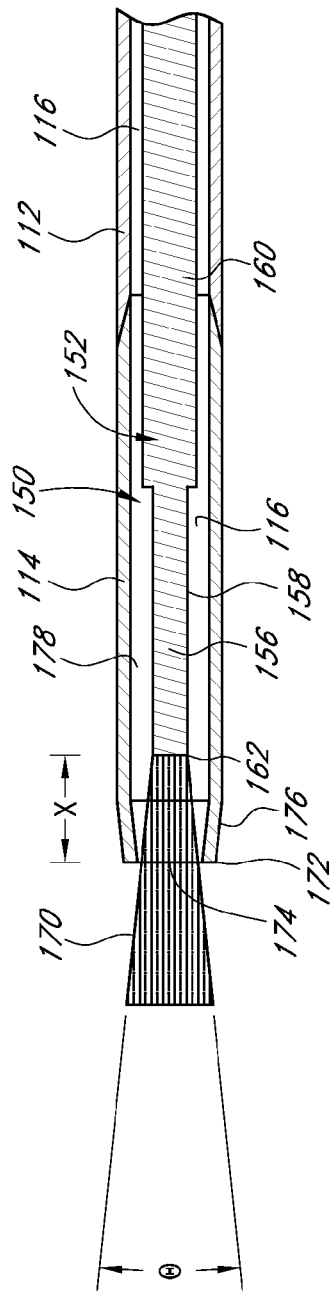
Fig. 3
Fig. 4

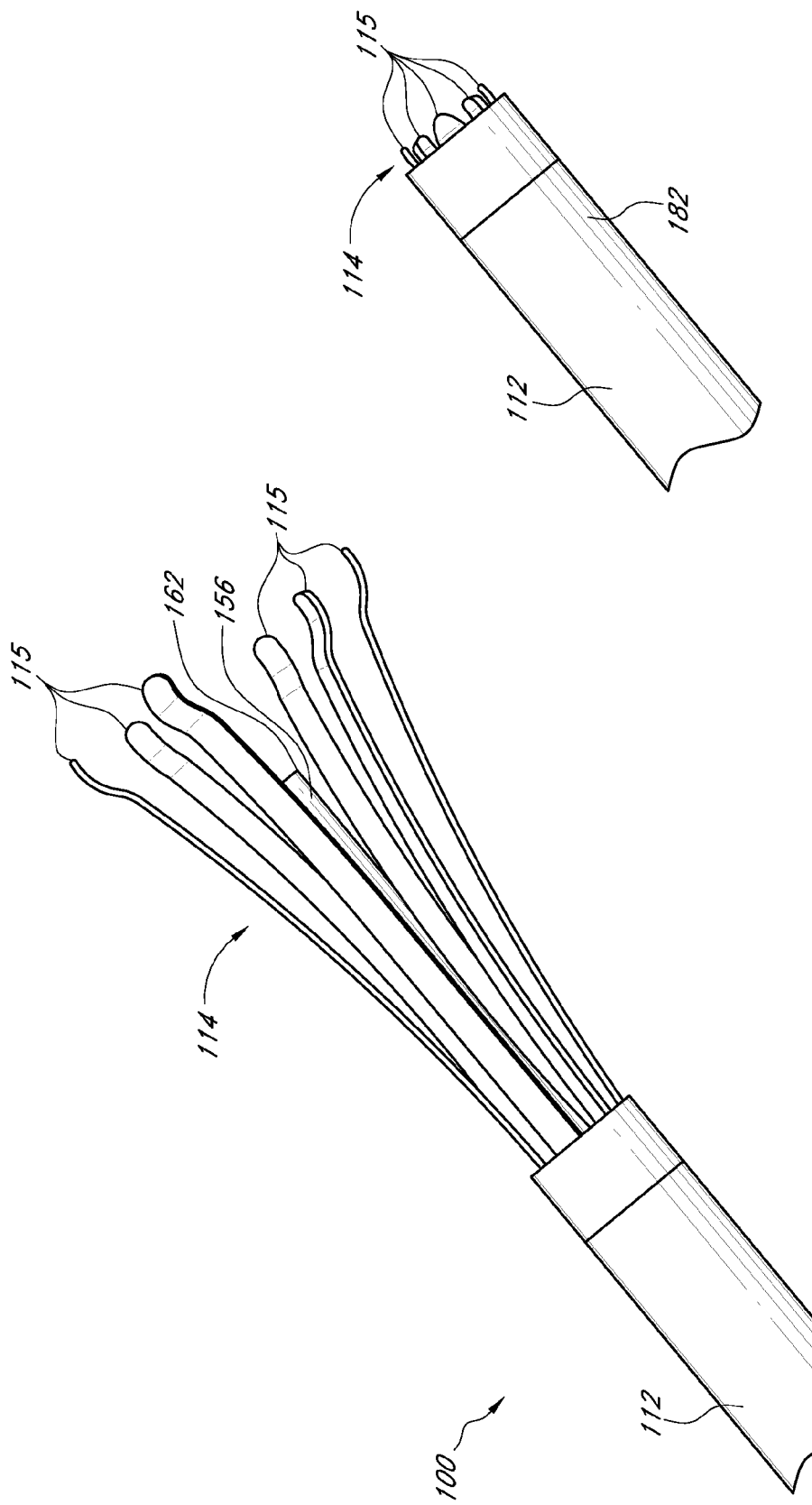

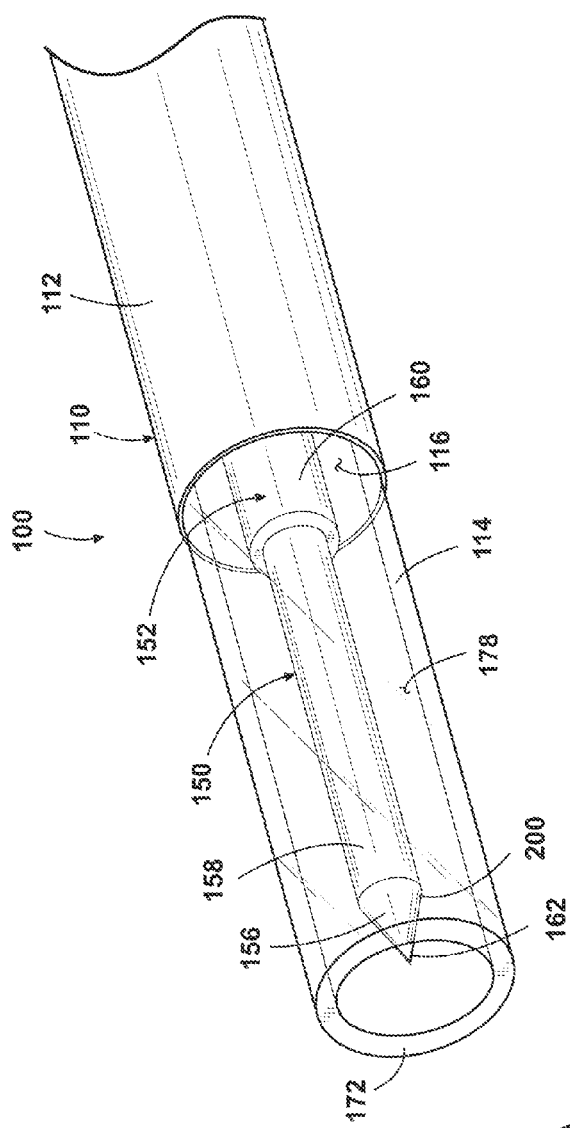
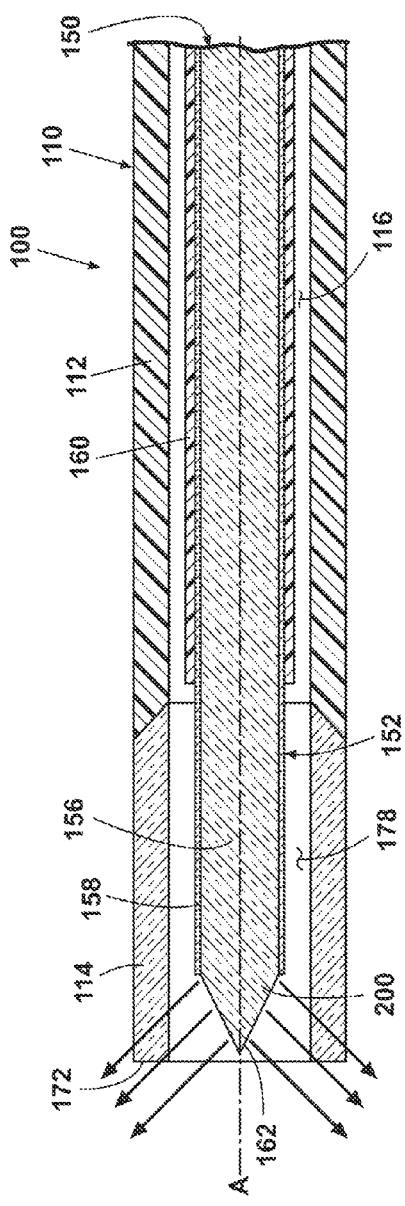
Fig. 12A
Fig. 12B

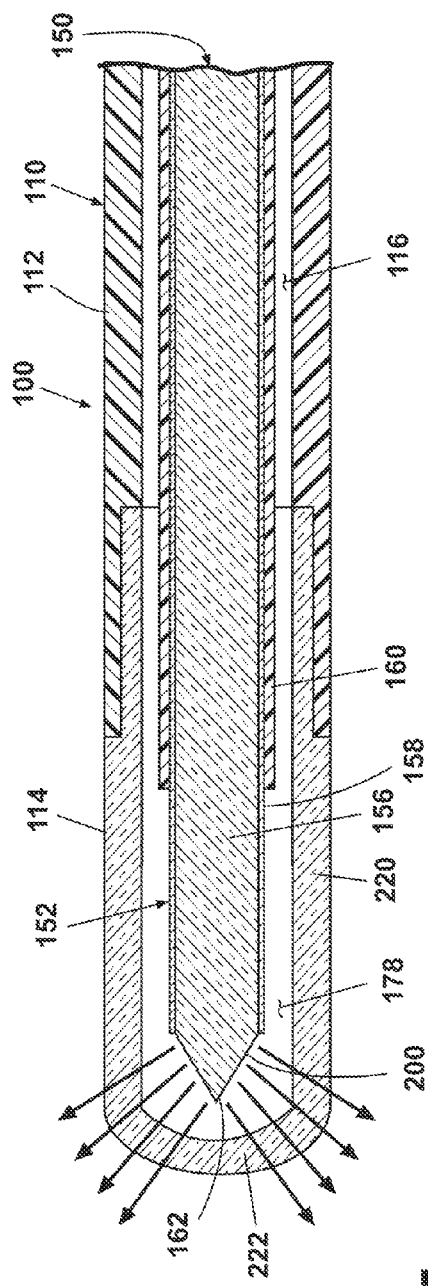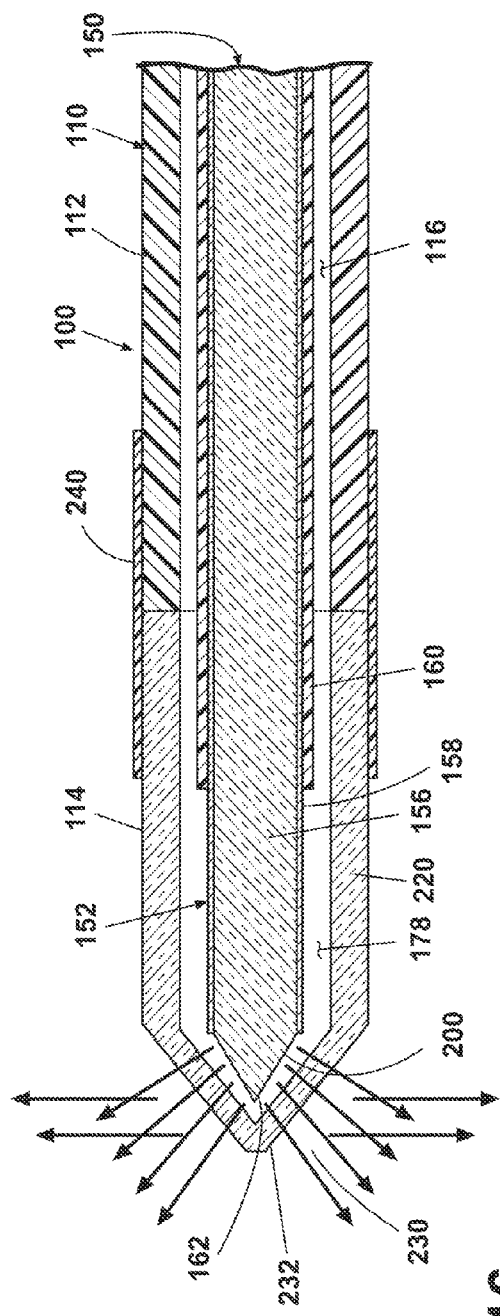

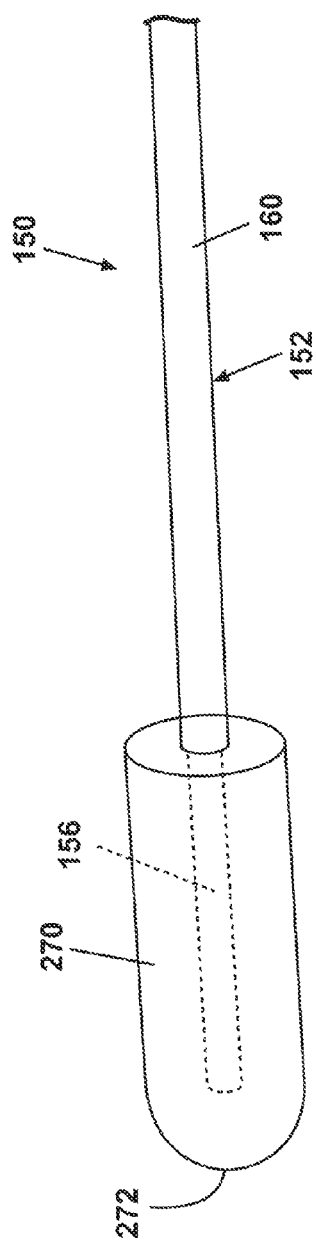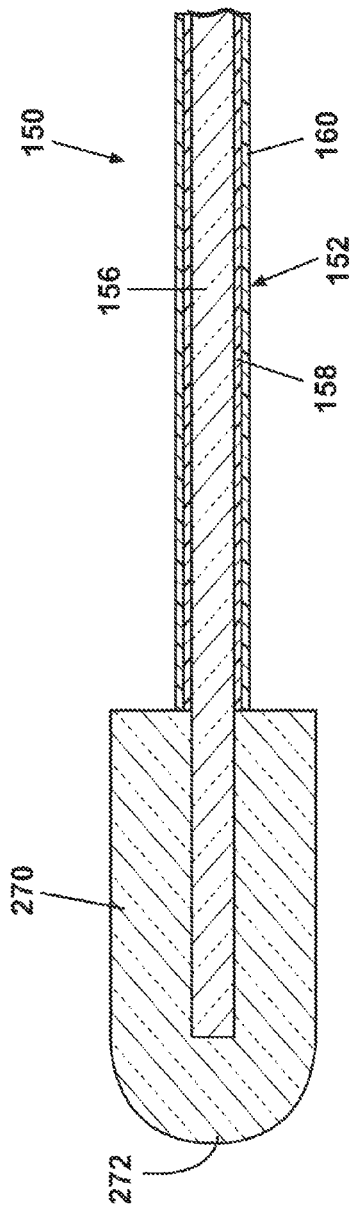
Fig. 20A
Fig. 20B

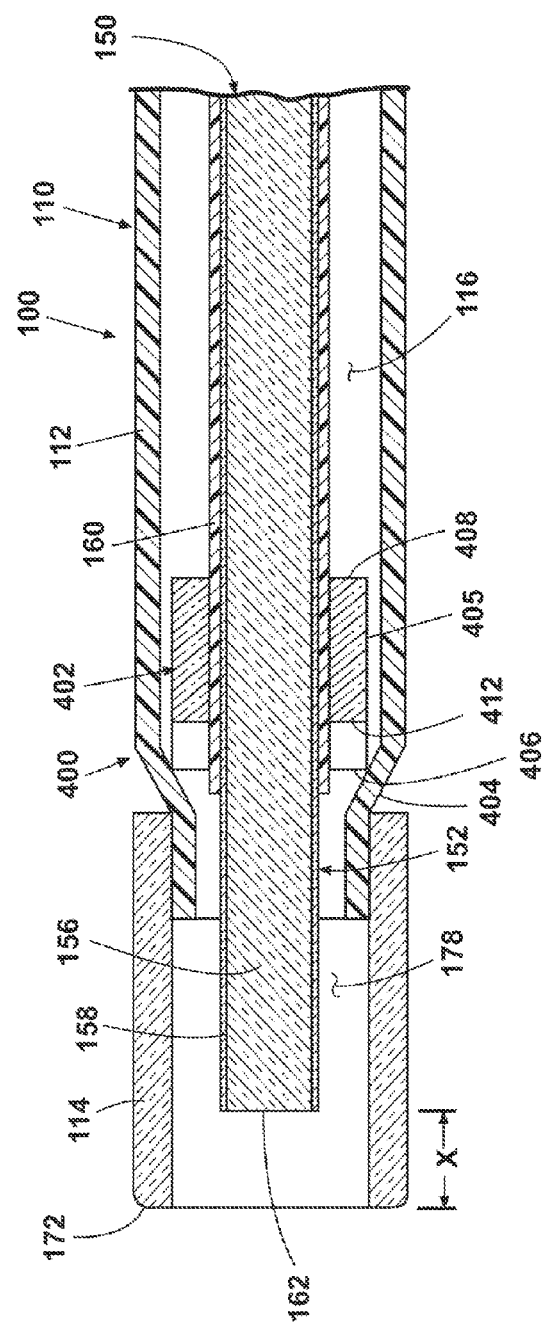
Fig. 22A
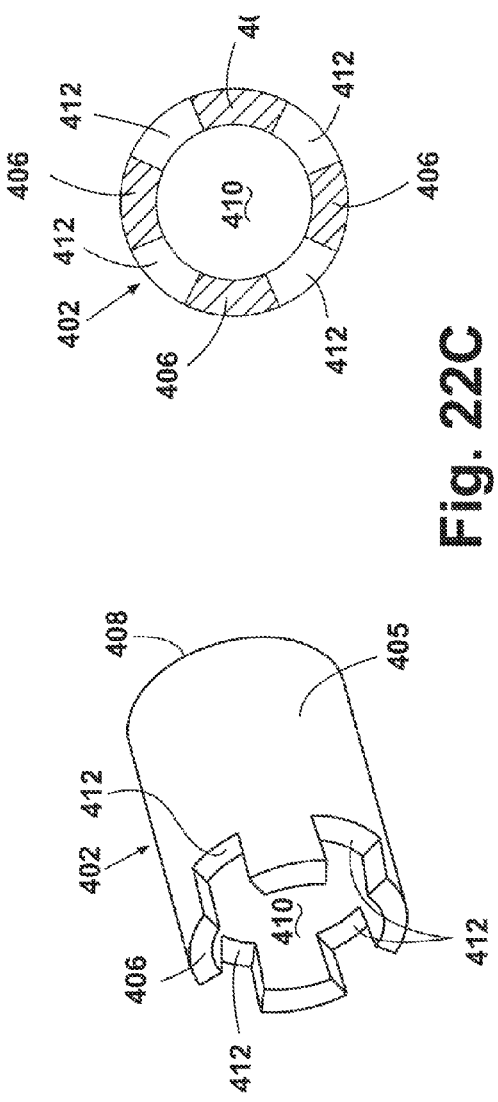
Fig. 22B
Fig. 22C

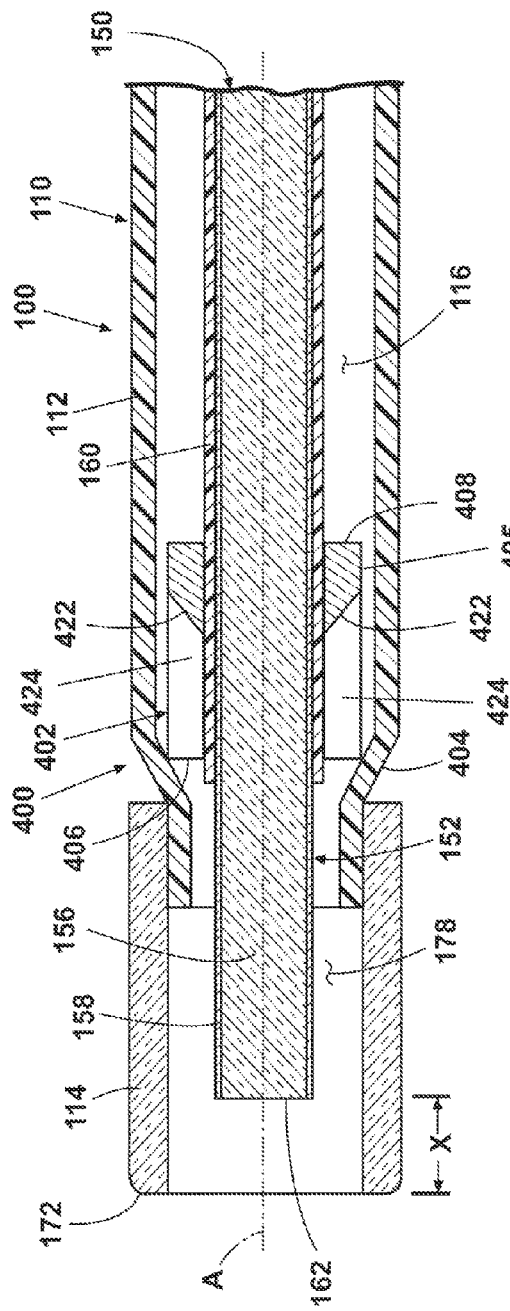
Fig. 25A
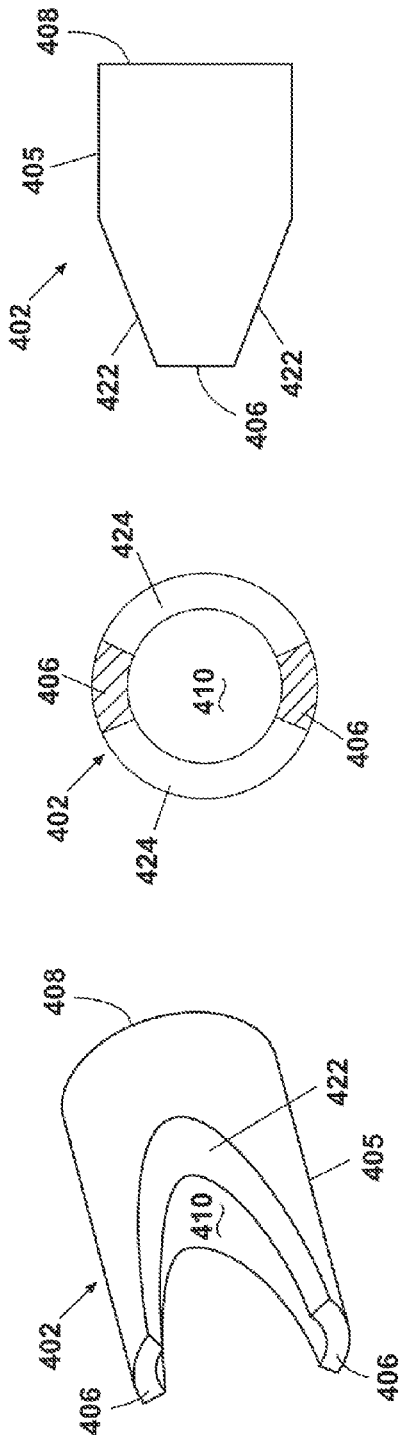
Fig. 25B
Fig. 25C
Fig. 25D

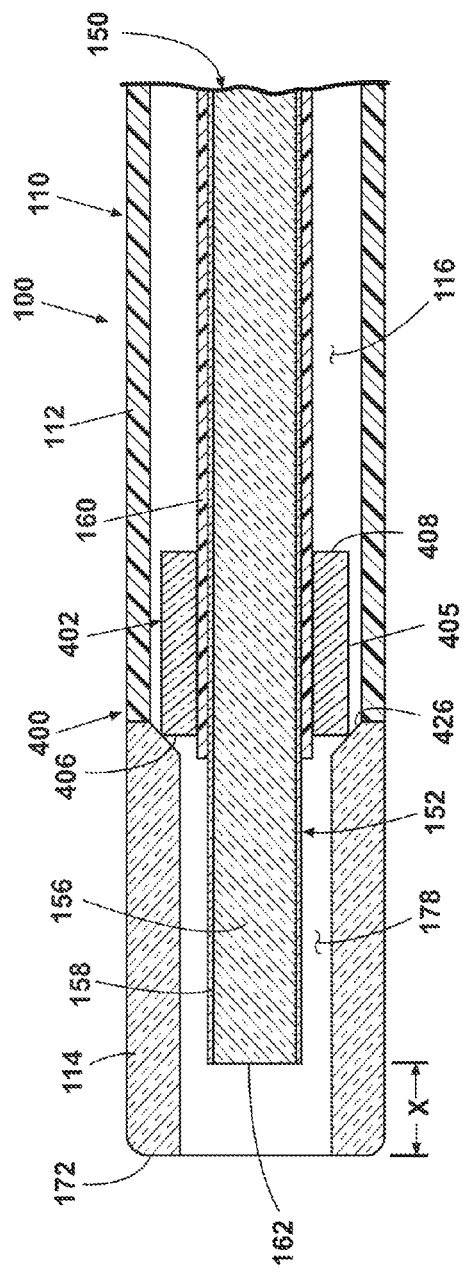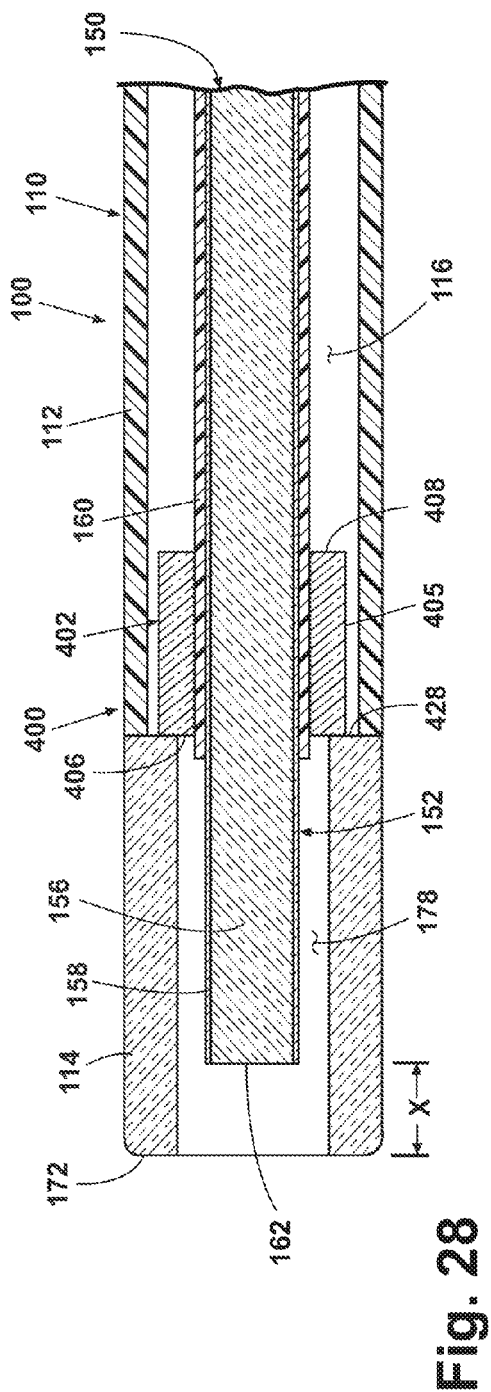

SYSTEMS AND METHODS FOR TREATING HOLLOW ANATOMICAL STRUCTURES

CROSS-REFERENCE TO RELATED APPLICATIONS

This application claims the benefit under 35 U.S.C. §119(e) of U.S. Provisional Applications No. 60/914,660, filed Apr. 27, 2007, titled SYSTEMS AND METHODS FOR TREATING HOLLOW ANATOMICAL STRUCTURES; and No. 60/986,577, filed Nov. 8, 2007, titled SYSTEMS AND METHODS FOR TREATING HOLLOW ANATOMICAL STRUCTURES, each of which is incorporated herein by reference in its entirety and made a part of this specification.

BACKGROUND

Optical fibers have been used in conjunction with laser systems to treat venous reflux for several years. The procedure involves placing an optical fiber in the vein and transmitting laser light through the fiber to the vein walls, causing the vein to close. In current vein ablation systems, an optical fiber is inserted into the vein, either bare or through an introducer sheath. In the latter case, the fiber tip is positioned outside and distal of the distal end of the introducer sheath during the procedure. In either case, when laser light is transmitted to the fiber, the fiber tip may become very hot, potentially causing its cladding and/or buffer material to burn inside the patient's body. In addition, if a hot fiber tip contacts the vein wall, it may cause perforations which can result in bruising and patient discomfort.

SUMMARY

The present disclosure includes, in one embodiment, an apparatus for treating a hollow anatomical structure. The apparatus comprises a shaft suitable for insertion into the hollow anatomical structure. The shaft has an internal lumen, a proximal end and a distal end. The apparatus further comprises an optical fiber located in the lumen. The optical fiber has a light emitting tip which is located in a distal region of the shaft lumen and proximal of the distal end of the shaft.

At least a portion of a sidewall of the shaft distal of the light emitting tip can optionally be transmissive of light. In such a variation the apparatus can optionally further comprise a laser light generator coupled to the optical fiber, wherein the portion of the sidewall is transmissive of at least one wavelength of light output by the generator.

The shaft of the apparatus can optionally further comprise an opening in the distal end of the shaft, and the distal tip of the optical fiber can optionally be spaced proximally from the opening by a distance suitable to substantially prevent buildup of proteins, coagulum and/or carbonization on the optical fiber tip, e.g., 2 mm to 20 mm, 2 mm to 10 mm, 2 mm to 8 mm, 2 mm to 5 mm, 2 mm to 4 mm, or 3 mm. The apparatus can further optionally comprise a fluid flow space in the shaft between the optical fiber and a sidewall of the shaft, and the fluid flow space can be in fluid communication with the opening such that fluid in the space can flow distally through the shaft and exit the shaft via the opening. Such an apparatus can further optionally comprise a liquid source in fluid communication with the fluid flow space and located proximal of the space. Such an apparatus can further optionally comprise a flow of liquid proceeding from the liquid source to the fluid flow space and out the opening of the shaft. The flow of liquid can optionally have a flow rate in the fluid flow space suitable to substantially prevent carbonization and protein buildup on the distal tip of the optical fiber; e.g., a flow rate of 5-60 cc/hour, 5-40 cc/hour, 10-30 cc/hour, 15-25 cc/hour, or about 20 cc/hour. Where employed, the liquid source can be configured to provide a fixed and predetermined flow rate, such as any of the flow rates specified above.

In another embodiment, an apparatus for treating a hollow anatomical structure comprises a cannula suitable for insertion into the hollow anatomical structure. The cannula has a distal end and a proximal end, and a lumen therein. The apparatus further comprises a light delivery device located at least partially in the cannula. The light delivery device has a light emitting portion. The light emitting portion of the light delivery device is located in the lumen of the cannula proximal of the distal end of the cannula. The apparatus further comprises a light field emanating distally from the light emitting portion of the light delivery device.

The cannula can optionally comprise an opening at the distal end of the cannula, and the light field can extend through the opening.

The cannula can optionally comprise a light-transmissive distal portion, and at least a portion of the light field can extend through the light-transmissive distal portion. The light-transmissive distal portion can optionally be sufficiently transmissive of light (optionally including one or more of the wavelengths 810 nm, 940 nm, 980 nm, 1320 nm, or 1470 nm, or the wavelength ranges 400-3000 nm or 800-1500 nm) to permit heating and reduction in diameter of a target hollow anatomical structure such as a vein.

The light delivery device can optionally comprise an optical fiber, and the light emitting portion can comprise a tip of the optical fiber. In such an apparatus the light can optionally comprise laser light.

The cannula can optionally comprise an opening at the distal end of the cannula, and the apparatus can further comprise a flow of liquid proceeding distally through the cannula, out the opening, and through at least a portion of the light field. The flow of liquid can optionally have a flow rate suitable to substantially prevent carbonization and protein buildup on the distal tip of the light delivery device; e.g., a flow rate of 5-60 cc/hour, 5-40 cc/hour, 10-30 cc/hour, 15-25 cc/hour, or about 20 cc/hour. Where employed, a liquid source can be configured to provide a fixed and predetermined flow rate in the cannula, such as any of the flow rates specified above. In such an apparatus, the light delivery device can optionally comprise an optical fiber, and the light emitting portion can comprise a tip of the optical fiber. The light can optionally comprise laser light. Such an apparatus can further optionally comprise a laser light generator coupled to the optical fiber.

The distal tip of the light delivery device can optionally be spaced proximally from the cannula opening by a distance suitable to substantially prevent buildup of proteins, coagulum and/or carbonization on the light delivery device tip, e.g., 2 mm to 20 mm, 2 mm to 10 mm, 2 mm to 8 mm, 2 mm to 5 mm, 2 mm to 4 mm, or about 3 mm.

In another embodiment, an apparatus for treating a hollow anatomical structure comprises a kit including a sheath and an optical fiber. The sheath has a distal end suitable for insertion into the hollow anatomical structure, a reference point located proximal of the distal end on a portion of the sheath intended to remain outside the hollow anatomical structure during use, and a lumen configured to receive the optical fiber. The lumen extends to the distal end of the sheath. The optical fiber has a distal tip suitable for light emission. The optical fiber bears a mark which is positioned along the length of the fiber such that, when the mark is aligned with the reference point, the distal tip of the fiber is located within the lumen, proximal of the distal end of the sheath.

The distal tip of the fiber can optionally be located 2 mm to 20 mm, 2 mm to 10 mm, 2 mm to 8 mm, 2 mm to 5 mm, 2 mm to 4 mm, or about 3 mm proximal of the distal end of the sheath when the mark is aligned with the reference point.

The lumen can optionally extend through a shaft of the sheath, and at least a distal portion of the shaft can be transmissive of the wavelength(s) of light emitted by the apparatus during use. The distal portion can optionally be sufficiently transmissive of light (optionally including one or more of the wavelengths 810 nm, 940 nm, 980 nm, 1320 nm, or 1470 nm, or the wavelength ranges 400-3000 nm or 800-1500 nm) to permit heating and reduction in diameter of a target hollow anatomical structure such as a vein.

The lumen can optionally extend through a shaft of the sheath, and at least a distal portion of the shaft can be formed from material which is substantially transparent or translucent to visible light.

The kit can optionally be contained in a sterile package.

The sheath can optionally comprise an introducer sheath. In such an apparatus, the sheath can optionally comprise a hub and a sidearm connected to the hub, with the sidearm being in fluid communication with the lumen of the sheath.

The sheath can optionally have an opening at its distal end.

In another embodiment, an apparatus for treating a hollow anatomical structure comprises a kit including a sheath and an optical fiber. The sheath has a distal end suitable for insertion into the hollow anatomical structure, and a lumen configured to receive the optical fiber. The lumen extends to the distal end of the sheath. The lumen has a sidewall, and at least a distal portion of the sidewall is transmissive of visible or infrared light. The distal portion can optionally be sufficiently transmissive of light (optionally including one or more of the wavelengths 810 nm, 940 nm, 980 nm, 1320 nm, or 1470 nm, or the wavelength ranges 400-3000 nm or 800-1500 nm) to permit heating and reduction in diameter of a target hollow anatomical structure such as a vein.

At least the distal portion of the sidewall can optionally be substantially transparent or translucent to visible light.

The optical fiber can optionally have a distal tip suitable for light emission. In such an apparatus the optical fiber can bear a mark which is positioned along the length of the fiber such that, when the mark is aligned with a reference point of the sheath, the distal tip of the fiber is located within the lumen, proximal of the distal end of the sheath. In such an apparatus the distal tip of the fiber can optionally be located 2 mm to 20 mm, 2 mm to 10 mm, 2 mm to 8 mm, 2 mm to 5 mm, 2 mm to 4 mm, or about 3 mm proximal of the distal end of the sheath, when the mark is aligned with the reference point.

The kit can optionally be contained in a sterile package.

The sheath can optionally comprise an introducer sheath. In such an apparatus, the sheath can optionally comprise a hub and a sidearm connected to the hub, wherein the sidearm is in fluid communication with the lumen of the sheath.

The sheath can optionally have an opening at its distal end.

The kit can optionally further comprise a liquid source configured for connection to and fluid communication with the lumen of the sheath. The liquid source can be further configured to provide a fixed and predetermined liquid flow rate in the sheath. The fixed and predetermined liquid flow rate can optionally be suitable to substantially prevent carbonization and protein buildup on the distal tip of the optical fiber; e.g., a flow rate of 5-60 cc/hour, 5-40 cc/hour, 10-30 cc/hour, 15-25 cc/hour, or about 20 cc/hour.

In another embodiment, an apparatus for treating a hollow anatomical structure comprises a sheath and a light delivery device. The sheath is configured to receive the light delivery device, and the sheath has an at least partially optically transmissive distal region. The distal region can optionally be sufficiently transmissive of light (optionally including one or more of the wavelengths 810 nm, 940 nm, 980 nm, 1320 nm, or 1470 nm, or the wavelength ranges 400-3000 nm or 800-1500 nm) to permit heating and reduction in diameter of a target hollow anatomical structure such as a vein. The light delivery device has a light emission portion, and the light emission portion is located in the distal region of the sheath, proximal of a distal end of the distal region.

The distal region of the sheath can optionally comprise a tube. Such a tube can optionally be formed from a material which is transmissive of visible or infrared light, or from a material which is substantially transparent or translucent to visible light.

The distal region of the sheath can optionally comprise a plurality of expandable members surrounding the light emission portion. The expandable members can optionally be spaced apart from each other to permit light to pass therebetween.

The light delivery device can optionally comprise an optical fiber. In such an apparatus the light emission portion can optionally comprise a distal tip of the fiber.

The apparatus can optionally further comprise a fluid delivery path in the sheath, which fluid delivery path extends distally to and beyond the light emission portion. The apparatus can further optionally comprise a flow of liquid proceeding distally through the sheath. The flow of liquid can optionally have a flow rate suitable to substantially prevent carbonization and protein buildup on the distal tip of the light delivery device; e.g., a flow rate of 5-60 cc/hour, 5-40 cc/hour, 10-30 cc/hour, 15-25 cc/hour, or about 20 cc/hour. Where employed, a liquid source can be configured to provide a fixed and predetermined flow rate in the sheath, such as any of the flow rates specified above.

In another embodiment, a method of treating a hollow anatomical structure comprises inserting into the hollow anatomical structure an apparatus comprising a sheath having a distal end, and a light emission portion disposed in the sheath proximal of the distal end. The method further comprises heating a wall of the hollow anatomical structure by emitting light from the light emission portion, while the light emission portion is disposed in the sheath proximal of the distal end.

The method can optionally further comprise delivering a liquid through the sheath and past the light emission portion. In such a method, emitting light can optionally comprise passing at least a portion of the light through the liquid, and heating the liquid with the light. Such a method can further optionally comprise delivering the heated liquid to the wall of the hollow anatomical structure and thereby heating the wall of the hollow anatomical structure.

Delivering the liquid can further optionally comprise delivering the liquid at a flow rate in the sheath suitable to substantially prevent carbonization and protein buildup on the distal tip of the light emission portion; e.g., a flow rate of 5-60 cc/hour, 5-40 cc/hour, 10-30 cc/hour, 15-25 cc/hour, or about 20 cc/hour. The liquid can be delivered via a liquid source can be configured to provide a fixed and predetermined flow rate in the sheath, such as any of the flow rates specified above.

In the method, emitting light can optionally comprise passing at least a portion of the light through a sidewall of the sheath.

The light emission portion of the apparatus can optionally comprise a tip of an optical fiber, with the optical fiber being disposed in the sheath.

In the method, the hollow anatomical structure can optionally comprise a vein or a varicose vein.

The method can optionally further comprise preventing, with the sheath, the light emission portion from contacting the wall of the hollow anatomical structure during the emitting light.

In another embodiment, a method of treating a hollow anatomical structure comprises positioning in the hollow anatomical structure a treatment system comprising a sheath and an optical fiber with a distal tip located in a lumen of the sheath; and establishing a liquid flow of 5-60 cc/hour, 5-40 cc/hour, 10-30 cc/hour, 15-25 cc/hour, or about 20 cc/hour proceeding distally through the sheath lumen, past the distal tip of the optical fiber. The method further comprises: while the distal tip is located in the lumen of the sheath and the liquid flow is present, emitting light energy from the optical fiber, and thereby heating a wall of the hollow anatomical structure.

The sheath can optionally comprise a distal tip opening and the distal tip of the optical fiber can be located 2 mm to 20 mm, 2 mm to 10 mm, 2 mm to 8 mm, 2 mm to 5 mm, 2 mm to 4 mm, or about 3 mm proximal of the distal tip opening of the sheath, when emitting the light energy from the optical fiber.

The method can optionally further comprise reducing the diameter of the hollow anatomical structure via the heating. The hollow anatomical structure can optionally comprise a vein.

Establishing the liquid flow can comprise establishing the liquid flow with a liquid source configured to provide liquid at a fixed and predetermined flow rate. The flow rate can be 5-60 cc/hour, 5-40 cc/hour, 10-30 cc/hour, 15-25 cc/hour, or about 20 cc/hour.

The method can optionally further comprise contacting the liquid flow with the distal tip of the optical fiber. At least a portion of the distal tip of the optical fiber can comprise bare core material of the fiber, and contacting the liquid flow with the distal tip of the fiber can comprise contacting the liquid flow with the bare core material. Establishing the liquid flow can comprise establishing the liquid flow distally along the length of the sheath, and then through a space between the distal tip of the optical fiber and an inner wall of the sheath. Establishing the liquid flow can further comprise establishing the flow out an opening in a distal region of the sheath. The opening can be located in a distal tip of the sheath and oriented transverse to a longitudinal axis of the sheath.

In one variation of the method, emitting light energy from the optical fiber can comprise passing at least a portion of the light energy through a sidewall of the sheath. The portion of the light energy passing through the sidewall can be sufficient to reduce the diameter of the hollow anatomical structure.

In one variation of the method, establishing the liquid flow can comprise establishing the liquid flow in a space in the sheath lumen between the optical fiber and an inner wall of the sheath.

One variation of the method further comprises minimizing carbonization on the distal tip of the optical fiber.

In another embodiment, a method of treating a hollow anatomical structure comprises positioning in the hollow anatomical structure a treatment system comprising a sheath and an optical fiber with a distal tip located in a lumen of the sheath; inhibiting carbonization and protein buildup on the distal tip of the optical fiber by establishing a liquid flow proceeding distally through the sheath lumen, past the distal tip of the optical fiber; and, while the distal tip is located in the lumen of the sheath and the liquid flow is present, emitting light energy from the optical fiber, and thereby heating a wall of the hollow anatomical structure.

In variations of the method, establishing the liquid flow comprises establishing a flow of 5-60 cc/hour, 5-40 cc/hour, 10-30 cc/hour, 15-25 cc/hour, or about 20 cc/hour.

In variations of the method, the sheath comprises a distal tip opening and the distal tip of the optical fiber is located 2 mm to 20 mm, 2 mm to 10 mm, 2 mm to 8 mm, 2 mm to 5 mm, 2 mm to 4 mm, or about 3 mm proximal of the distal tip opening of the sheath, when emitting the light energy from the optical fiber.

The method can further optionally comprise reducing the diameter of the hollow anatomical structure via the heating. The hollow anatomical structure can optionally comprise a vein.

The method can further comprise contacting the liquid flow with the distal tip of the optical fiber. Optionally, at least a portion of the distal tip of the optical fiber comprises bare core material of the fiber, and contacting the liquid flow with the distal tip of the fiber comprises contacting the liquid flow with the bare core material. As a further option, establishing the liquid flow can comprise establishing the liquid flow distally along the length of the sheath, and then through a space between the distal tip of the optical fiber and an inner wall of the sheath. Establishing the liquid flow can still further comprise establishing the flow out an opening in a distal region of the sheath. The opening can be located in a distal tip of the sheath and oriented transverse to a longitudinal axis of the sheath.

In one variation of the method, emitting light energy from the optical fiber can comprise passing at least a portion of the light energy through a sidewall of the sheath. The portion of the light energy passing through the sidewall can be sufficient to reduce the diameter of the hollow anatomical structure.

In one variation of the method, establishing the liquid flow comprises establishing the liquid flow in a space in the sheath lumen between the optical fiber and an inner wall of the sheath.

Establishing the liquid flow can comprise establishing the liquid flow with a liquid source configured to provide liquid at a fixed and predetermined flow rate. The flow rate can be 5-60 cc/hour, 5-40 cc/hour, 10-30 cc/hour, 15-25 cc/hour, or about 20 cc/hour.

Another embodiment comprises an apparatus for treating a hollow anatomical structure. The apparatus comprises a sheath having an inner lumen, the sheath being sized and configured for insertion into the hollow anatomical structure; an optical fiber positioned in the lumen of the sheath, a distal tip of the fiber being positioned in a distal portion of the sheath; and a liquid flow advancing distally along the lumen of the sheath, the distal tip of the fiber contacting the liquid flow, the liquid flow having a flow rate of 5-60 cc/hour, 5-40 cc/hour, 10-30 cc/hour, 15-25 cc/hour, or about 20 cc/hour.

In one variation of the apparatus, at least the distal portion of the sheath has a sidewall which is highly transmissive of light. The sidewall can be sufficiently transmissive of light to allow heating and reduction in diameter of the hollow anatomical structure. Additionally the sidewall can be sufficiently transmissive of light in at least one of the wavelengths 810 nm, 940 nm, 980 nm, 1320 nm, and 1470 nm, or in at least one of the wavelength ranges 400-3000 nm and 800-1500 nm to permit heating and reduction in diameter of the hollow anatomical structure.

The sheath can optionally comprise a distal tip opening and the distal tip of the optical fiber can be located 2 mm to 20 mm, 2 mm to 10 mm, 2 mm to 8 mm, 2 mm to 5 mm, 2 mm to 4 mm, or about 3 mm proximal of the distal tip opening of the sheath. The liquid flow can optionally advance through the distal tip opening and out the sheath.

The apparatus can optionally further comprise a beam of light emanating from the optical fiber, the beam of light having sufficient intensity to facilitate heating and reduction in diameter of the hollow anatomical structure. At least a portion of the beam of light can pass through a sidewall of the sheath.

The hollow anatomical structure can optionally comprise a vein.

At least a portion of the distal tip of the optical fiber can comprise bare core material of the fiber, and the liquid flow can contact the bare core material.

The liquid flow can extend distally within the lumen of the sheath, and through a space between the distal tip of the optical fiber and a sidewall of the sheath. At least a portion of the sidewall alongside the distal tip of the optical fiber can be sufficiently transmissive of light to allow heating and reduction in diameter of the hollow anatomical structure. The sidewall portion can be sufficiently transmissive of light in at least one of the wavelengths 810 nm, 940 nm, 980 nm, 1320 nm, and 1470 nm, or at least one of the wavelength ranges 400-3000 nm and 800-1500 nm to permit heating and reduction in diameter of the hollow anatomical structure.

The apparatus can optionally further comprise a liquid source in fluid communication with the lumen of the sheath. The liquid source can be configured to provide a fixed and predetermined liquid flow rate in the sheath, e.g., a flow rate of 5-60 cc/hour, 5-40 cc/hour, 10-30 cc/hour, 15-25 cc/hour, or about 20 cc/hour.

Another embodiment comprises an apparatus for treating a hollow anatomical structure. The apparatus comprises a sheath having an inner lumen, the sheath being sized and configured for insertion into the hollow anatomical structure; an optical fiber positioned in the lumen of the sheath, a distal tip of the fiber being positioned in a distal portion of the sheath; and a liquid flow advancing distally along the lumen of the sheath, the distal tip of the fiber contacting the liquid flow, the liquid flow having a flow rate suitable to inhibit carbonization and protein buildup on the distal tip of the optical fiber.

The liquid flow rate can optionally be 5-60 cc/hour, 5-40 cc/hour, 10-30 cc/hour, 15-25 cc/hour, or about 20 cc/hour.

At least the distal portion of the sheath can have a sidewall which is highly transmissive of light. Such a sidewall can be sufficiently transmissive of light to allow heating and reduction in diameter of the hollow anatomical structure. Such a sidewall can be sufficiently transmissive of light in at least one of the wavelengths 810 nm, 940 nm, 980 nm, and 1320 nm, or at least one of the wavelength ranges 400-3000 nm and 800-1500 nm to permit heating and reduction in diameter of the hollow anatomical structure.

The sheath can optionally comprise a distal tip opening and the distal tip of the optical fiber can be located 2 mm to 20 mm, 2 mm to 10 mm, 2 mm to 8 mm, 2 mm to 5 mm, 2 mm to 4 mm, or about 3 mm proximal of the distal tip opening of the sheath. The liquid flow can advance through the distal tip opening and out the sheath.

The apparatus can optionally further comprise a beam of light emanating from the optical fiber, the beam of light having sufficient intensity to facilitate heating and reduction in diameter of the hollow anatomical structure. At least a portion of the beam of light can pass through a sidewall of the sheath.

The hollow anatomical structure can comprise a vein.

In one variation of the apparatus, at least a portion of the distal tip of the optical fiber comprises bare core material of the fiber, and the liquid flow contacts the bare core material.

In one variation of the apparatus, the liquid flow extends distally within the lumen of the sheath, and through a space between the distal tip of the optical fiber and a sidewall of the sheath.

In one variation of the apparatus, at least a portion of the sidewall alongside the distal tip of the optical fiber is sufficiently transmissive of light to allow heating and reduction in diameter of the hollow anatomical structure. The sidewall portion can be sufficiently transmissive of light in at least one of the wavelengths 810 nm, 940 nm, 980 nm, 1320 nm, and 1470 nm, or at least one of the wavelength ranges 400-3000 nm or 800-1500 nm to permit heating and reduction in diameter of the hollow anatomical structure.

The apparatus can optionally further comprise a liquid source in fluid communication with the lumen of the sheath. The liquid source can be configured to provide a fixed and predetermined liquid flow rate in the sheath, e.g., a flow rate of 5-60 cc/hour, 5-40 cc/hour, 10-30 cc/hour, 15-25 cc/hour, or about 20 cc/hour.

In another embodiment, an apparatus for treating a hollow anatomical structure comprises a sheath having an elongate shaft defining an internal lumen. The shaft has a sidewall, a proximal portion, and a distal portion, the sidewall being more transmissive of therapeutic light energy in the distal portion than in the proximal portion. The distal portion of the shaft forms a distal tip of the shaft and has a distal-facing opening at the distal tip. The apparatus further comprises an optical fiber disposed within and movable along the lumen. The optical fiber has a fiber tip located in the distal portion of the shaft at a firing position which is 2-20 mm proximal of the distal tip of the shaft. The apparatus further comprises a light propagation path which extends distally from the fiber tip and through the distal-facing opening.

The firing position can be a static firing position relative to sheath.

The sidewall can be made from a first material in the proximal portion and from a second material in the distal portion, the second material being more transmissive of therapeutic light than the first material. In such a variation, the first material can be more flexible than the second material. The second material can be one of quartz, sapphire, synthetic fused silica, polycarbonate, polyetheretherketone, polysufone, polyarylethersulfone, polyetherimide, and polyamide-imide. The second material can optionally be transmissive of wavelengths of light from 400 to 3000 nm, or from 800 to 1500 nm.

The optical fiber can be insertable into the hollow anatomical structure separately from the sheath.

The shaft can be sized for insertion into a vein. In such a variation, the outer diameter of the shaft can be less than 5 mm.

The apparatus can further comprise a liquid flow advancing distally along the shaft lumen and contacting the fiber tip. Such an apparatus can further comprise a liquid source in fluid communication with the lumen, the liquid source being configured to provide the liquid flow at a fixed and predetermined liquid flow rate. The liquid flow rate can optionally be 5-60 cc/hr. In one variation, the liquid source can comprise a saline bag fluidly coupled to the shaft lumen through a flow regulator. The flow regulator can comprise a flow restriction fluidly coupling the saline bag to the lumen. The flow restriction can comprise an orifice having a predetermined effective opening that is sized to provide the predetermined liquid flow rate. The liquid source can comprise a liquid reservoir and a liquid flow path from the reservoir to the shaft lumen, and the flow restriction comprises an orifice of a fixed size positioned in the flow path, the orifice size being smaller than that of the rest of the liquid flow path.

The apparatus can further comprise a position limiter configured to limit the position of the fiber tip relative to the distal tip of the shaft at the firing position. In one variation, the position limiter can comprise a stop configured to limit the distal movement of the optical fiber within the shaft lumen when the fiber tip is at the firing position The stop can comprise cooperating structures of the optical fiber and the distal shaft portion that are configured to limit the relative insertion of the fiber tip within the lumen to the firing position. The stop can optionally be located 12 mm from the distal tip of the optical fiber, or within 10-20 mm of the distal tip of the optical fiber.

The fiber tip can be optically coupled to the distal-facing opening to form the light propagation path.

In another embodiment, a method of treating a hollow anatomical structure comprises inserting a sheath with a distal end into the hollow anatomical structure, inserting an optical fiber into the sheath, and positioning a tip of the optical fiber at a firing position anywhere from 2-20 mm proximal of the distal end. The method further comprises emitting light energy from the fiber tip while the tip is disposed in the sheath proximal of the distal end and withdrawing the sheath and optical fiber along the hollow anatomical structure while emitting the light energy.

The method can further comprise maintaining the position of the fiber tip in the firing position during the emitting and the withdrawing.

The insertion of the optical fiber in the sheath optionally occurs prior to inserting the sheath into the hollow anatomical structure. In such a method, the optical fiber can be moveable with respect to the sheath after the optical fiber is inserted into the sheath.

The insertion of the sheath into the hollow anatomical structure optionally occurs prior to inserting the optical fiber into the sheath.

The emitting can comprise emitting light energy through a sidewall of the sheath.

The emitting can comprise emitting light energy through a distal portion of a sidewall of the sheath that is more transmissive of light energy than is a proximal portion of the sidewall.

The method can further comprise establishing a liquid flow proceeding distally through the sheath and past the tip of the optical fiber. In such a method, the establishing can further comprise providing a predetermined liquid flow rate via a liquid source. The predetermined flow rate can be fixed. The predetermined liquid flow rate can optionally be provided at 5-60 cc/hour.

The emitting can comprise emitting light energy distally from the fiber tip. In one variation, the emitting light energy distally can comprise emitting light energy through a distal-facing opening formed in the distal end of the sheath.

The emitting can comprise emitting light energy into a wall of the hollow anatomical structure.

In another embodiment, an apparatus for treating a blood vessel comprises a sheath defining an inner lumen and having a proximal portion and a distal portion, with the sheath configured for insertion into the blood vessel. The apparatus further comprises an optical fiber positioned in the lumen and having a distal tip positioned in the distal portion. The apparatus further comprises a liquid flow advancing distally along the lumen and contacting the distal tip, and a liquid source in fluid communication with the inner lumen, the liquid source configured to provide the liquid flow at a predetermined liquid flow rate of 5-60 cc/hour.

The predetermined liquid flow rate can be fixed.

The proximal portion of the sheath can be formed from a first material and the distal portion of the sheath can be formed from a second material that is more transmissive of light energy than the first material. The proximal portion and the distal portion can have approximately the same outer diameter.

The apparatus can further comprise a flow path from the liquid source to the sheath, the flow path having a flow passage of a predetermined size that restricts the liquid flow to provide the predetermined liquid flow rate. In one variation, at least a portion of the flow passage can be smaller than the remainder of the flow path from the liquid source to the sheath. The flow passage can comprise a channel having a fixed size. The channel can optionally comprise a capillary tube. Such an apparatus can further comprise a flow restrictor member disposed in the channel. In another variation, the liquid source can be non-motorized. Such a liquid source can comprise a liquid reservoir, and the flow of liquid from the liquid reservoir can be driven by at least one of gravity and compression of the liquid reservoir. The liquid reservoir can comprise a saline bag. The saline bag can be fluidly coupled to the inner lumen through a flow regulator. The flow regulator can comprise a flow restriction fluidly coupling the saline bag to the lumen. The flow restriction can comprise an orifice having a predetermined effective opening that is sized to provide the predetermined liquid flow rate.

The optical fiber can be moveable with respect to the sheath.

The distal sheath portion can form a distal tip of the sheath and can have a distal-facing opening at the distal tip of the sheath through which the liquid flow can pass. In one variation, the distal tip of the optical fiber and the sheath can define a light propagation path which extends distally from the distal tip of the optical fiber and through the distal-facing opening.

In another embodiment, a method of treating a hollow anatomical structure comprises positioning a treatment system in the hollow anatomical structure, the treatment system comprising a sheath having a lumen and an optical fiber with a distal tip located in the lumen. The method further comprises establishing a liquid flow at a liquid flow rate of 5-60 cc/hour proceeding distally through the lumen and past the distal tip. The method further comprises emitting light energy from the optical fiber, thereby causing heating of a wall of the hollow anatomical structure, while the distal tip is located in the lumen and the liquid flow is present. The method further comprises withdrawing the treatment system along the hollow anatomical structure while emitting the light energy.

The establishing can further comprise providing the liquid flow at predetermined liquid flow rate. The predetermined liquid flow rate can optionally be fixed. The providing can further comprise restricting the liquid flow from a liquid reservoir to the sheath lumen to provide the fixed and predetermined liquid flow rate. In one variation, the restricting can further comprise flowing liquid through a smaller diameter portion of a flow passage coupling the liquid reservoir to the sheath lumen. In another variation, the restricting can further comprise flowing liquid through a channel having a fixed size. The channel can optionally be rigid. The restricting can further comprise flowing liquid through a capillary tube. The restricting can further comprise flowing liquid past a flow restrictor member disposed in the channel.

The establishing can further comprise providing the liquid flow rate from a non-motorized liquid source. In one variation, the liquid source can comprise a liquid reservoir and the providing further comprises driving the flow of liquid from the liquid reservoir by at least one of gravity and compression of the liquid reservoir. In another variation, the providing can further comprise flowing liquid from a saline bag.

The method can further comprise maintaining the position of the distal fiber tip relative to the distal end of the sheath during the emitting and the withdrawing.

The positioning can comprise sequentially inserting the optical fiber in the sheath and inserting the sheath into the hollow anatomical structure.

The positioning can comprise sequentially inserting the sheath into the hollow anatomical structure and inserting the optical fiber into the sheath.

The emitting can comprise emitting light energy through a sidewall of the sheath.

The emitting can comprise emitting light energy through a distal portion of the sheath. In such a method, the emitting light energy through a distal portion of the sheath can comprise emitting light energy through a portion of the distal portion that is transmissive of light energy.

The emitting can comprise emitting light energy distally from the distal tip. In such a method, the emitting can comprise emitting light energy through a distal-facing opening formed in a distal portion of the sheath.

The emitting can comprises emitting light energy into a wall of the hollow anatomical structure.

The emitting can comprise emitting light energy radially from the distal tip.

BRIEF DESCRIPTION OF THE DRAWINGS

FIG. 3 is a side sectional view of the distal portion of FIG. 2.

FIG. 4 is a side sectional view of a distal portion of another embodiment of the sheath.

FIG. 7A is a side view of the sheath of FIG. 5.

FIG. 7B is a side view of the sheath of FIG. 5, with expandable members thereof in a retracted configuration.

FIG. 12A is a perspective view of a distal portion of another embodiment of the sheath and another embodiment of the light delivery device.

FIG. 12B is a side sectional view of the sheath and the light delivery device of FIG. 12A.

FIG. 15 is a side sectional view of a distal portion of another embodiment of the sheath with the light delivery device of FIG. 12A.

FIG. 16 is a side sectional view of a distal portion of another embodiment of the sheath with the light delivery device of FIG. 12A.

FIG. 20A is a perspective view of a distal portion of another embodiment of the light delivery device.

FIG. 20B is a side sectional view of the light delivery device of FIG. 20A.

FIG. 22A is a side sectional view of a distal portion of another embodiment of the light delivery device comprising a position limiter.

FIG. 22B is a perspective view of a portion of the position limiter of FIG. 22A.

FIG. 22C is a front view of a portion of the position limiter of FIG. 22A.

FIG. 25A is a side sectional view of a distal portion of another embodiment of the light delivery device comprising a position limiter.

FIG. 25B is a perspective view of a portion of the position limiter of FIG. 25A.

FIG. 25C is a front view of a portion of the position limiter of FIG. 25A.

FIG. 25D is a top view of a portion of the position limiter FIG. 25A.

FIG. 27 is a side sectional view of a distal portion of another embodiment of the light delivery device comprising a position limiter.

FIG. 28 is a side sectional view of a distal portion of another embodiment of the light delivery device comprising a position limiter.

DETAILED DESCRIPTION OF THE PREFERRED EMBODIMENTS

The features of the systems and methods will now be described with reference to the drawings summarized above. The drawings, associated descriptions, and specific implementation are provided to illustrate preferred embodiments of the invention(s) disclosed herein, and not to limit the scope of the patent protection sought in connection with this specification.

In addition, methods and functions of treatment systems or devices described herein are not limited to any particular sequence, and the acts relating thereto can be performed in other sequences that are appropriate. For example, described acts may be performed in an order other than that specifically disclosed, or multiple acts may be combined in a single act.

Figure 1:
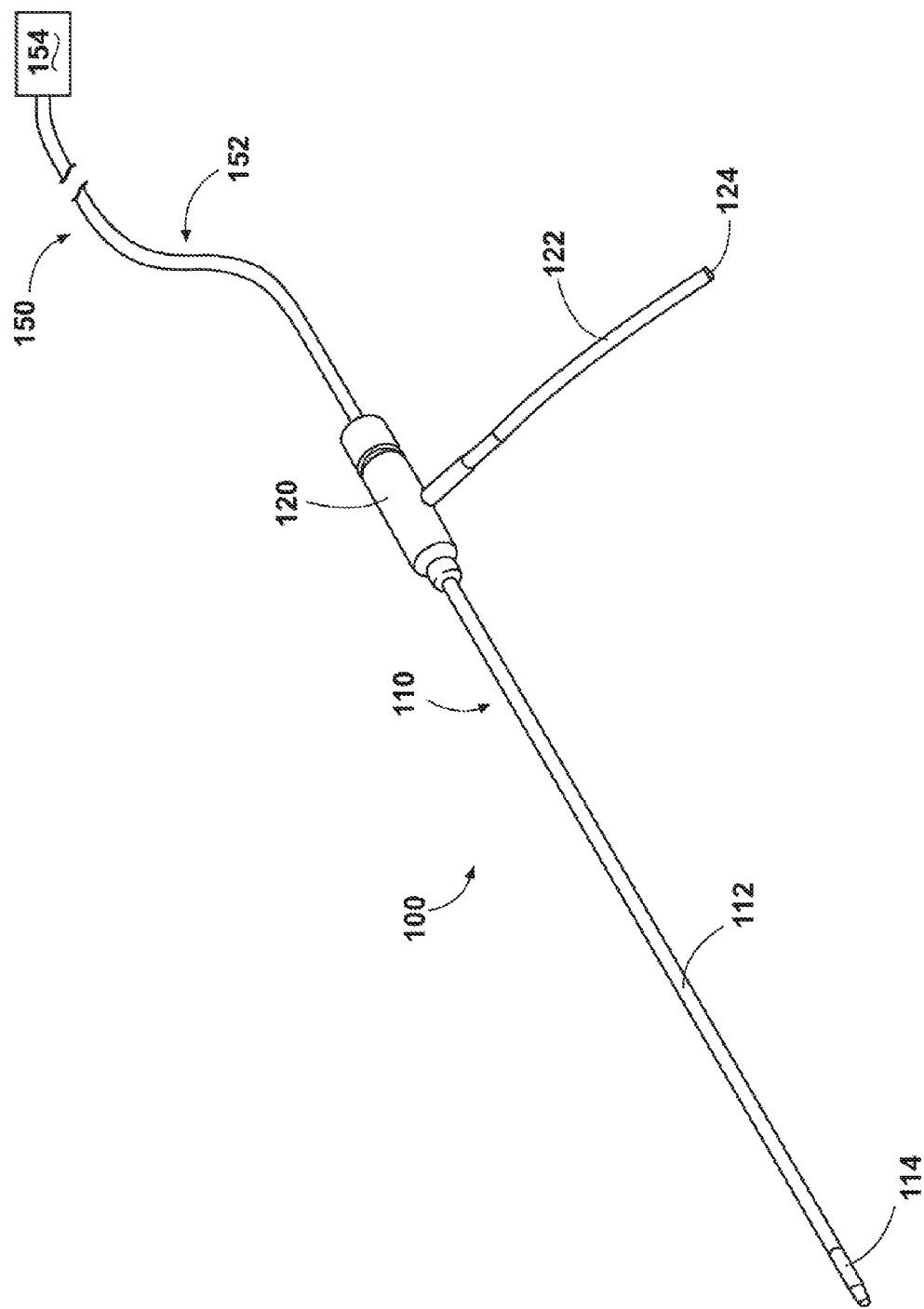
FIG. 1 is a perspective view of one embodiment of a system for treating a hollow anatomical structure.
Figure 2:
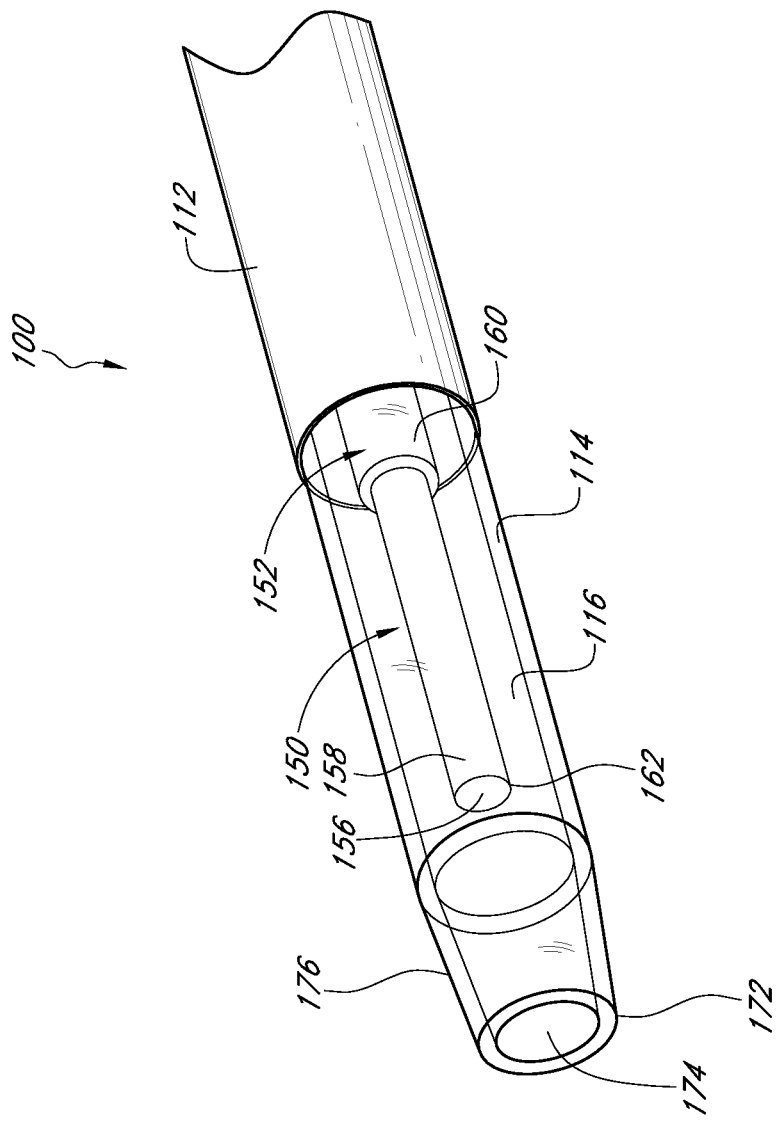
FIG. 2 is a detailed perspective view of a distal portion of a sheath and a light delivery device of the system of FIG. 1.

One embodiment of a system 100 for treating a hollow anatomical structure or "HAS" (e.g., a blood vessel, a vein, a varicose vein, a fallopian tube, ovarian vein, etc.) is depicted in FIGS. 1, 2 and 3. The depicted embodiment of the system 100 includes an introducer sheath 110 having a preferably tubular and flexible shaft 112, a distal end of which includes a protective distal tip portion 114. The sheath 110 preferably further comprises a hub 120 attached to a proximal end of the shaft 112, and a sidearm 122 which can include a port 124 to facilitate introduction of fluids into the sidearm 122. In the depicted embodiment the hub 120 is configured to permit fluid communication between the sidearm 122 and the shaft 112 such that a fluid introduced into the port 124 of the sidearm 122 can flow into a lumen 116 (see FIG. 3) of the shaft 112. An appropriate connector, such as a Luer fitting (not shown) can be included at the port 124 (or on the hub 120 instead of the sidearm 122) to permit connection of medical apparatus, fluid sources, etc. to the sidearm 122. The sheath 110 can be sized for insertion into a HAS, and can have an outer diameter of 1-5 mm.

The system 100 depicted in FIGS. 1-3 can further comprise a light delivery device 150 disposed in the lumen 116 of the shaft 112. In the depicted embodiment the light delivery device 150 comprises an optical fiber 152, which can be coupled to a laser light generator 154. Where employed, the optical fiber 152 can extend proximally through the hub 120 of the introducer sheath 110 to the laser light generator 154, to conduct laser energy output by the generator 154 through the shaft 112 to the desired treatment area as will be discussed in greater detail below. A hemostatic seal or the like can be provided in the hub 120 to provide a seal around the fiber 152 and prevent fluid in the shaft lumen 116 from escaping proximally beyond the hub 120. As an alternative to the depicted optical fiber 152, the light delivery device 150 can comprise a small laser light source or other light source disposed in the lumen 116 of the shaft 112.

In the depicted embodiment, the optical fiber 152 comprises a light-conducting optical core 156 formed from glass, silica or other suitable light-conducting material(s), surrounded by cladding 158 made from silica or polymers or the like, to promote internal reflection within the core 156. A protective jacket 160 surrounds the cladding 158 and the core 156. The jacket 160 is optionally stripped back to expose a distal tip portion of the cladding 158 and core 156, and this distal tip portion is typically between about 2 mm and 8 mm in length. Alternatively, the optical fiber 152 can be employed without any of the jacket 160 stripped from the distal fiber tip, e.g. with only the distal face of the core 156 exposed at the distal tip. The core 156 preferably terminates in an unclad, distal light emitting tip 162. In operation, light 170 (e.g. laser light) propagates distally down the core 156 of the fiber 152, exits the core 156 at the light emitting tip 162 and advances generally distally from the tip 162. The tip 162 is preferably a generally flat surface oriented generally orthogonal to the longitudinal axis of the fiber 152. Alternatively, however, the tip 162 can also be formed, shaped, or ground to create facets, or a spherical or prismatic tip face to direct a portion of the light in the radial direction.

The distal tip portion 114 of the shaft 112 is preferably transparent to, or otherwise highly transmissive of, the wavelength(s) of light 170 emitted via the tip 162 of the fiber 152 (or other light delivery device 150) during operation of the system 100. Such wavelengths of light 170 can optionally range from 400 to 3000 nm, or from 800 to 1500 nm. The distal tip portion 114 can also be sufficiently transmissive of such wavelength(s) of light (or of specific suitable therapeutic wavelengths such as 810 nm, 940 nm, 980 nm, 1320 nm and/or 1470 nm) to permit heating and reduction in diameter of a target hollow anatomical structure such as a vein, and/or to avoid melting and/or burning the distal tip portion 114 when light (optionally including light in the above-noted wavelength(s) is emanating from the fiber 152 at sufficient intensity to lead to heating and reduction in diameter of the HAS or vein. Suitable materials for use in forming the distal tip portion 114 include, without limitation, quartz, sapphire, borosilicate glass (PYREX(™)), synthetic fused silica, polycarbonate, polyetheretherketone, polysulfone, polyarylethersulfone, polyetherimide, and polyamide-imides. The distal tip portion 114 can optionally comprise a tube with a wall thickness of 0.2-1.0 mm.

Some or all of the light 170 can propagate from the tip 162, distally and/or outwardly through the sidewalls and/or end of the distal tip portion 114 and to the desired treatment area. The fiber tip 162 can therefore remain disposed within the distal tip portion 114 of the shaft 112 during treatment, and the distal tip portion 114 can protect the hot fiber tip 162 from contact with the inner wall of the vein or other target HAS (and vice versa).

In the depicted embodiment, the fiber tip 162 is spaced proximally from a distal end 172 of the distal tip portion 114 by a distance X of 2 mm to 20 mm. The distal tip portion 114 can further optionally include an opening 174 to permit light and/or liquids to flow from the tip portion 114, and/or a tapered tip region 176 to facilitate easy and atraumatic insertion of the shaft 112 into small-diameter HAS's.

Preferably, the light delivery device 150 and the lumen 116 of the shaft 112/tip portion 114 are sized so that a fluid delivery space 178 is provided between the light delivery device 150 and the inner wall of the shaft 112/tip portion 114. In such an embodiment, a liquid such as saline (or any other suitable liquid) can be delivered distally through the shaft 112 and tip portion 114, and out the opening 174, during delivery of light 170 from the device 150. The delivered liquid can optionally absorb the wavelength(s) of light 170 emitted from the device 150, to a sufficient degree to induce heating and/or boiling of the delivered liquid as it flows through the delivery space 178 and light 170, and out the opening 174. The hot/boiling liquid will also tend to heat the tip portion 114. Thus, this embodiment of the system 100 can be capable of providing at least three mechanisms of therapeutic HAS wall heating: (1) hot or boiling fluid heating of the HAS walls, (2) conductive heating from the hot sheath tip 114, and (3) light or laser energy 170 transmitted directly to the HAS walls.

By controlling the light/laser power, the distance X, liquid flow rate, and liquid starting temperature, the HAS heating zone/length can be controlled and an optimized thermal therapy can be accomplished. Also, by selecting a preferentially water absorbing light/laser wavelength (e.g. 1320 nm, etc.) the therapy can be one in which substantially all of the light/laser energy is absorbed by the (aqueous) liquid which both flows from the sheath opening 174 and heats the sheath tip 114 to create a heat zone for effecting tissue thermal therapy. The aforementioned parameters are preferably varied to ensure that the heating is maintained at or around 100° C., providing a controlled therapy with minimal complications (e.g., minimizing uncontrolled high temperatures that cause increased depth of thermal injury leading in turn to potential pain and bruising; and avoiding fiber tip wall contact and perforations that lead to blood extravasations and bruising).

In one embodiment of a method of use of the system 100, the target HAS (e.g. a vein such as the greater saphenous vein) can first be accessed by using a suitable access technique (e.g. the standard Seldinger technique). A guide wire is passed into the target HAS, and the introducer sheath 110 is fed over the guidewire into the target HAS and advanced to the desired start location. In the case of the greater saphenous vein, the desired start location is just below the sapheno-femoral junction. The guidewire is then withdrawn from the sheath 110 and the light delivery device 150 is advanced distally through the hub 120 and down the shaft 112 until the device 150 is appropriately positioned within the sheath tip 114. Where the light delivery device 150 comprises the optical fiber 152, the fiber tip 162 is positioned so that it is proximal of the distal end 172 of the tip 114 by the distance X. An appropriate mark (or a projection such as a flange, slidable collar or "donut") can be provided on a proximal region of the fiber 152 to facilitate positioning of the fiber tip 162, such that alignment of the mark with the proximal edge of the hub indicates that the desired position of the fiber tip 162 has been reached. A suitable lock, clamp or Touhy-Borst valve can be provided in the hub 120 to prevent longitudinal movement of the fiber 152 within the sheath, and this lock or clamp can be activated after positioning of the fiber tip 162 within the sheath 110 as described above. Alternatively, the sheath 110 and light delivery device 150 can be combined prior to insertion and advanced into the target HAS together, without need for a guidewire.

Before or after placement of the optical fiber 152 or other light delivery device, the position of the sheath 110 relative to the desired treatment location can be verified using appropriate techniques such as ultrasound. In addition, the target HAS can optionally be prepared for treatment by using any desired combination of manual compression, compression bandages, and/or injection of tumescent anesthesia into the tissues surrounding the target HAS, to exsanguinate the HAS lumen (in the case of treating blood vessels) and reduce the lumenal diameter in preparation for heat treatment.

If desired, a liquid flow via the sidearm 122, through the sheath 110 and into the HAS lumen can be commenced as described above. The light delivery device 150 is activated, providing light, such as laser light, at one or more appropriate wavelengths or wavelength ranges such as 810 nm, 940 nm, 980 nm, 1320 nm, and/or 1470 nm, and/or 400-3000 nm or 800-1500 nm, and at an appropriate power level. The assembly of the sheath 110 and device 150 is slowly withdrawn through the HAS lumen, preferably at a rate about of 0.5-5 millimeters per second. As the assembly is moved along the lumen, therapeutic heat is delivered to the HAS walls via one or more of the following: (1) heating of the HAS walls via any hot or boiled delivered liquid, (2) conductive heating from the hot sheath tip 114, and (3) light or laser energy 170 transmission directly to the HAS walls. After the desired length of the target HAS has been treated with the therapeutic heat, the sheath 110 and device 150 can be removed and appropriate post-procedural care can be administered.

In one embodiment of the method of use of the system 100, a liquid flow suitable to minimize, inhibit or substantially prevent buildup of proteins, coagulum and/or carbonization on the fiber tip 162 (e.g., having a flow rate of 5-60 cc/hour, 5-40 cc/hour, 10-30 cc/hour, 15-25 cc/hour, or about 20 cc/hour) is established in the sheath 110 during treatment of a target HAS. As discussed in further detail below, this liquid flow has also been found suitable to minimize, inhibit or substantially prevent perforation of the hollow anatomical structure being treated (including veins in particular). When employed with the system 100 depicted in FIGS. 1-3, this liquid flow advances distally, along and in contact with the distal portion of the fiber 152, in the (typically annular) fluid delivery space 178 between the distal portion of the fiber and the inner wall of the distal tip portion 114. Where the fiber 152 of the system 100 includes a stripped distal portion as shown in FIGS. 2-3, the liquid flow advances along and in contact with the cladding 158; and/or the unclad, distal light emitting tip 162 points or faces distally toward a portion of the liquid flow located in the sheath tip 114 distal of the tip 162 such that the bare, unclad core material which forms the tip 162 contacts this distal portion of the liquid flow. The liquid flow can comprise saline or any other suitable liquid disclosed herein.

The method of use of the system 100 can also optionally include positioning the fiber tip 162 in the sheath 112 such that the tip 162 is spaced proximally from the distal end 172 and/or opening 174 of the distal tip portion 114 by the distance X (see FIG. 3) of 2 mm to 20 mm, 2 mm to 10 mm, 2 mm to 8 mm, 2 mm to 5 mm, 2 mm to 4 mm, or 3 mm; or otherwise by a distance suitable to minimize, inhibit or substantially prevent buildup of proteins, coagulum and/or carbonization on the fiber tip 162. This tip spacing has also been found suitable to minimize, inhibit or substantially prevent perforation of the hollow anatomical structure being treated (including veins in particular).

It has been found that providing an appropriate fluid flow over the distal portion of the fiber 152, and/or properly spacing the fiber tip 162 from the distal end 172 and/or opening 174 of the distal tip portion 114 helps to minimize buildup of coagulum and/or carbonized blood components on the fiber tip 162. This in turn minimizes perforation of the treated hollow anatomical structure, particularly in veins, possibly due to the elimination of the enlarged hot carbonized mass often observed on the tip of an optical fiber used in treatment of a hollow anatomical structure. Accordingly, a method of minimizing carbonization on the fiber tip 162 and/or minimizing HAS/vein perforation (or a step of minimizing carbonization and/or HAS/vein perforation, as part of a method of use of the system 100) can comprise establishing a liquid flow as specified above, and/or spacing the fiber tip 162 from the distal end 172 and/or opening 174 as specified above.

In addition, a low-carbonization or no-carbonization (or low-perforation or no-perforation) system 100 can include the optical fiber 152 disposed within the sheath 110, with the distal portion of the fiber 152 (including at least a portion of the exposed cladding 158, and/or the light emitting tip 162) located in the distal tip portion 114 (which can be transparent or otherwise highly transmissive of the wavelength(s) of light emitted from the fiber tip 162) and surrounded by (and/or in contact with) the liquid flow specified above. The fiber tip 162 can be spaced from the distal end 172 and/or distal tip opening 174 (if present) of the distal tip portion 114, by the distance X specified above. Where both the fluid flow and the fiber tip spacing are employed, there can exist a distal portion of the fluid flow within the distal tip portion 114 of the sheath 110, which distal portion of the fluid flow extends distally from the fiber tip 162 by the distance X. The distal portion of the fluid flow preferably contacts the fiber tip 162; where the fiber tip 162 is an unclad portion of the fiber core material, the distal portion of the fluid flow contacts the fiber core material at the fiber tip 162.

FIG. 4 depicts an alternative embodiment of the system 100, which can be similar in structure, use and function to any of the variations of the system 100 of FIGS. 1-3, except as further described herein. In the system 100 of FIG. 4, the distal tip portion 114 of the shaft 112 of the sheath 110 is substantially non-transparent to the wavelength(s) of light emitted from the device 150 during use. The distance X between the tip 162 and the sheath distal end 172, and the angle θ through which the light 170 is propagated, can be selected to ensure that most or all of the light 170 will not be transmitted to the sheath tip walls, but will exit through the opening 174 and be transmitted to the target HAS walls.

As a further variation of the system 100 of FIGS. 1-3, a light-absorbing coating can be applied to the distal tip portion 114. The coating can be selected to absorb, highly or completely, the wavelength(s) of light emitted by the device 150. Thus the emitted light is converted to heat in the tip portion 114 and any delivered liquid, and energy is delivered to the target HAS walls via the hot and/or boiled liquid and/or contact with the heated tip portion 114.

As a variation of the systems 100 of FIGS. 1-4, the shaft 112 of the sheath 110 can include two, preferably concentric, lumens. In such a sheath 110, the inner lumen provides space for the fiber 152 or other light delivery device and the outer lumen provides a conduit for any liquid(s) to flow. At the distal end of the shaft 112, the outer lumen communicates with the inner lumen and sheath tip 114, allowing saline to flow around the tip 162 of the fiber 152 or other device 150.

As another variation of the systems 100 of FIGS. 1-4, the light delivery device 150 can be replaced with another energy application device in the form of, e.g., an electrically driven heater wire or heater coil positioned in the sheath tip 114 in a similar manner as the stripped portion of the optical fiber 152 depicted in FIGS. 2-4. Such an electrically driven heater wire or coil can be employed to heat the delivered liquid and/or sheath tip as described elsewhere herein, and thereby therapeutically heat the walls of the target HAS.

As another variation of the systems 100 of FIGS. 1-4, the light delivery device 150 can be replaced with a thermally insulated conduit for the flow of a pre-heated liquid (e.g., saline, etc.) out the distal end of the sheath 110 and to treatment site. The temperature of the liquid and its flow rate can be controlled to optimize the temperature and length of the treatment zone at the sheath tip.

Figure 4A:
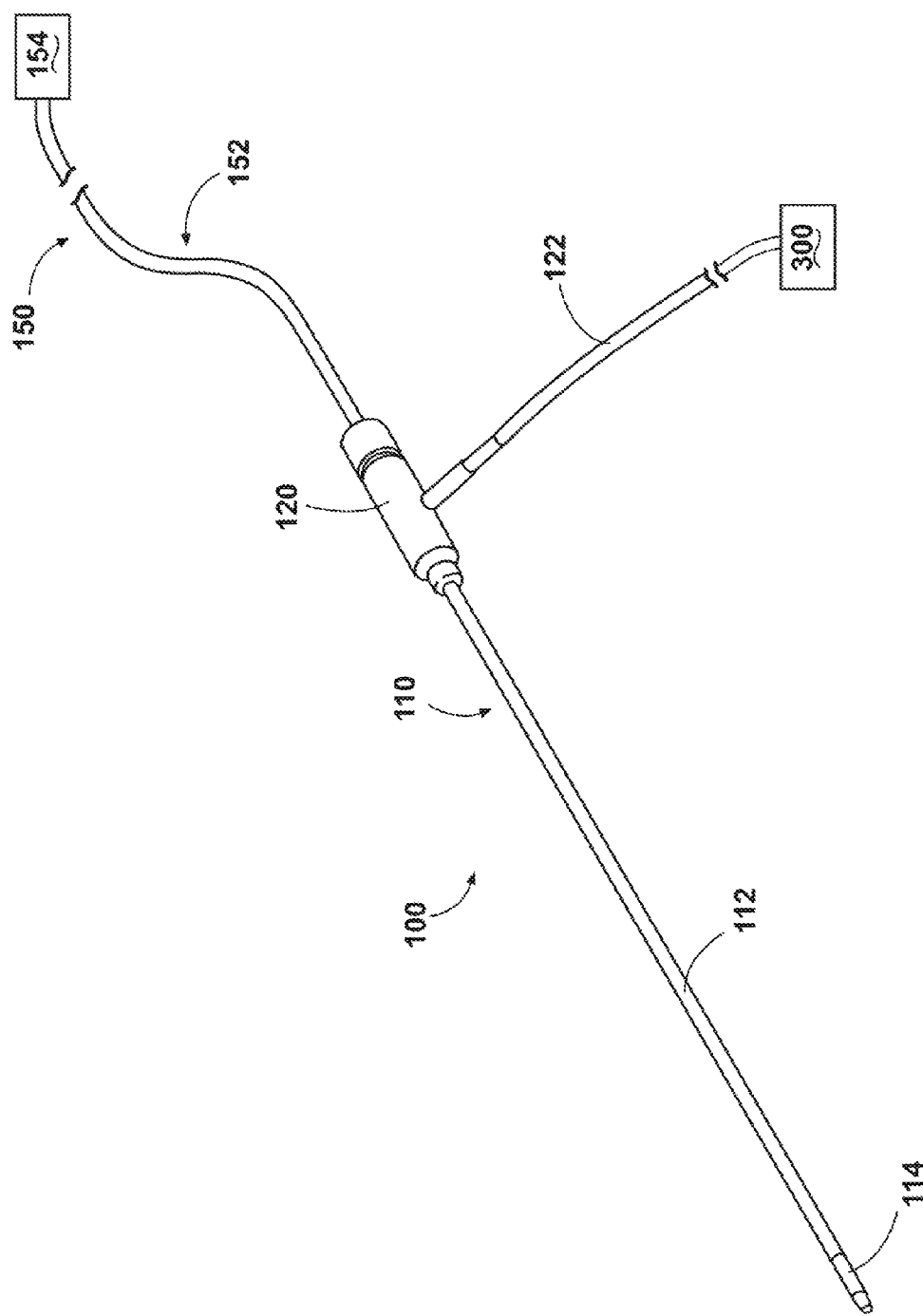
FIG. 4A is a schematic view of another embodiment of a system for treating a hollow anatomical structure having a liquid source.

FIG. 4A depicts an alternative embodiment of the system 100, which can be similar in structure, use and function to any of the variations of the system 100 of FIGS. 1-3, except as described herein. In the system 100 of FIG. 4A, a liquid source 300 is provided which may be used to facilitate delivery of the liquid flow at a desired flow rate as discussed above. The depicted liquid source 300 is in fluid communication with the inner lumen 116 of the sheath 112 via the sidearm 122 or other suitable connection to the sheath 112.

Figure 4B:
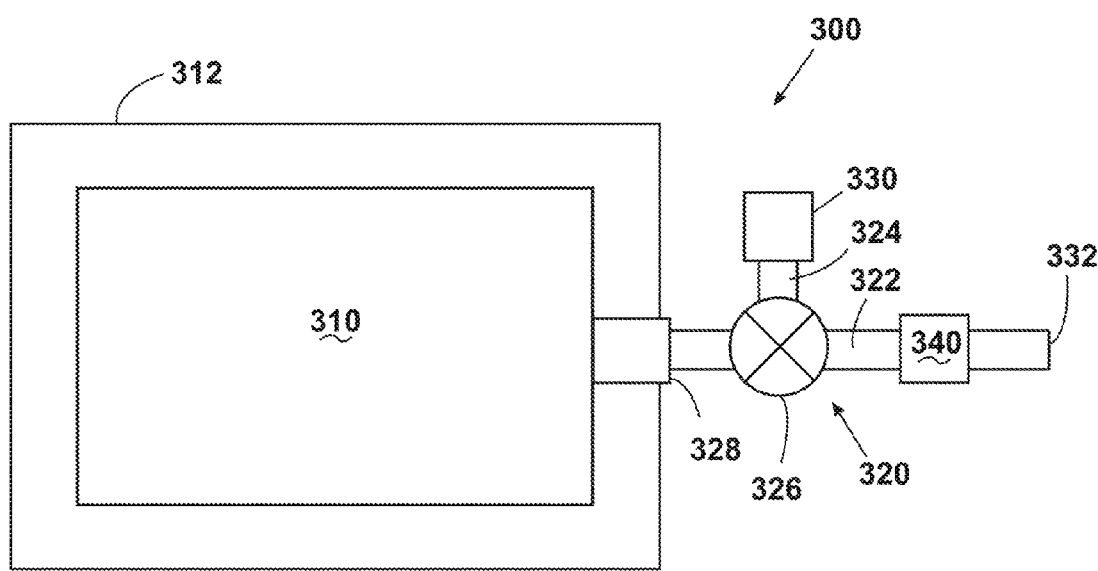
FIG. 4B is a schematic view of a liquid source usable with the systems of FIGS. 1-4A and 5-28.

FIG. 4B depicts one embodiment of the liquid source 300. The depicted liquid source 300 generally comprises a liquid reservoir 310 coupled to a plumbing network 320 which is operable to control the flow of liquid into and out of the reservoir 310. The liquid reservoir 310, which optionally can be housed in a suitable housing 312, preferably comprises a pressurizable liquid reservoir 310, such as an elastic bladder or a cylinder with a spring-loaded piston received therein. Alternatively a non-elastic reservoir 310 can be employed, which can rely on gravity to drive liquid flow out of the liquid source 300.

In the depicted embodiment, the plumbing network 320 comprises a primary passage 322 and a secondary passage 324 which are interconnected by a three-way stopcock 326. The primary passage 322 can be coupled to and in fluid communication with the liquid reservoir 310 via a source connector 328, while the secondary passage 324 terminates in a fill connector 330, which preferably comprises a luer fitting but can comprise any suitable connector to facilitate connection to a syringe for filling the reservoir 310. The primary passage 322 terminates in an outlet 332, which can comprise a luer connector or other hardware suitable for facilitating fluid communication between the outlet 332 and the sheath 110 or sidearm 122.

A flow regulator 340 is preferably located on the primary passage 322, and is operable to regulate the rate at which liquid flows from the liquid source 300. The flow regulator preferably provides a fixed and predetermined flow rate through the primary passage 322, e.g., 5-60 cc/hour, 5-40 cc/hour, 10-30 cc/hour, 15-25 cc/hour, or about 20 cc/hour. This can be implemented via, for example, a restricted passage through the flow regulator 340 that, in combination with the fluid pressure applied by the pressurizable or gravity-driven liquid reservoir 310, yields the desired liquid flow rate. In one embodiment, the flow regulator 340 can provide two or more such fixed and predetermined flow rates with, for example, a rotatable disc that can be turned to select and position one of a number of restricted passages, provided as holes through the disc, in alignment with the primary passage 322. The selected restricted passage thus determines the flow rate through the regulator 340. In one such embodiment, the flow regulator can provide one relatively large fixed and predetermined flow rate, designated as a "prime" setting, which can be used to quickly prime the sheath 110 and the rest of the system 100 with liquid before beginning a treatment of a hollow anatomical structure. This "prime" flow rate can be larger than any of those specified herein for use when treating an HAS. The "prime" flow rate can be provided along with one or more "treatment" flow rates.

To use the liquid source 300, the practitioner can first connect the source 300 to the sheath 100 via the outlet 332 and the sidearm 122 or other apparatus suitable to provide fluid communication between the source 300 and the lumen of the sheath 110. Alternatively, the connection can be made later in the process. The practitioner charges the liquid reservoir by setting the stopcock 326 to provide fluid communication only between the secondary passage 324 and the reservoir 310, and connecting a syringe or other appropriate apparatus to the fill connector 330. Notably, a syringe with a graduated barrel can be employed to fill the reservoir 310 with a precise predetermined volume of liquid. The syringe is operated to pump a desired volume (e.g. less than 100 cc, or less than 50 cc) of liquid through the plumbing network 320 and into the reservoir 310. Where the reservoir 310 is of the pressurizable type, the inflow of liquid pressurizes the reservoir 310 (e.g., by expanding the elastic bladder or forcing the piston back against the spring). Once the reservoir 310 is full, the practitioner can place the stopcock 326 in the closed position, preventing any outflow from the liquid source 300, and if desired remove the syringe or other apparatus from the fill connector 330. The sheath 110 can be primed directly from the syringe, or with the liquid in the reservoir 310, or from the syringe while still connected to the fill connector 330 and with the stopcock 326 at a proper setting. Where suitable, the flow regulator 340 can be placed in the "prime" setting and the stopcock 326 opened to allow liquid to flow from the reservoir 310 to the sheath lumen at the "prime" flow rate until the priming is complete, and the stopcock closed. However primed, the system 100 or sheath 110 is inserted into the target hollow anatomical structure as disclosed elsewhere herein. At the appropriate time after insertion, the stopcock is opened (and the flow regulator 340 set to the appropriate fixed and predetermined flow rate) to deliver liquid from the reservoir 310 and into the lumen of the sheath 110 at an appropriate fixed and predetermined treatment flow rate as discussed herein, e.g., 5-60 cc/hour, 5-40 cc/hour, 10-30 cc/hour, 15-25 cc/hour, or about 20 cc/hour. The flow rate is then sustained, either at a constant rate or within a desirable range, for as long as necessary during the treatment.

Advantageously, the liquid source 300 and flow regulator 340 can be employed to quickly and conveniently provide a liquid flow at a desired flow rate for treating an HAS. In contrast, a conventional saline bag and tubing set can require a great deal of setup and adjustment before the desired flow rate is achieved. This increases the time and cost expended when performing a treatment.

Figure 4D:
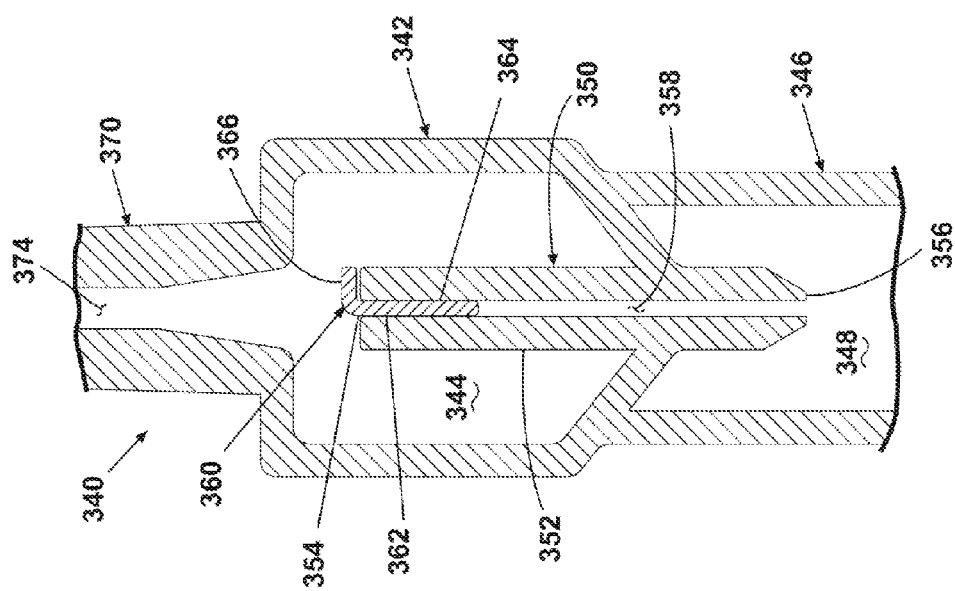
FIG. 4D is a detailed view of FIG. 4C.
Figure 4C:
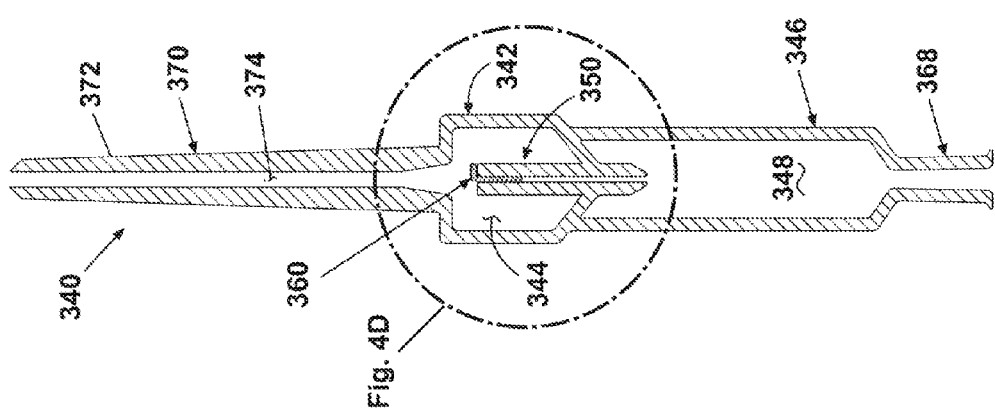
FIG. 4C is a schematic view of a flow regulator usable with the liquid source of FIG. 4B.

FIGS. 4C and 4D depict one embodiment of the flow regulator 340 usable with the liquid source 300. The flow regulator 340 of FIGS. 4C-4D comprises a reservoir chamber 342 having an inlet port 370, a drip chamber 346 having an outlet port 368, and a flow restriction 350. The inlet port 370 is in fluid communication with the liquid reservoir 310 (FIG. 4B) and supplies liquid to the reservoir chamber 342, which is in fluid communication with the drip chamber 346 via the flow restriction 350. The flow restriction 350 regulates the flow rate of liquid into the drip chamber 346. From the drip chamber 346, liquid is fed via the outlet port 368 to the sidearm 122 (FIG. 4A) of the system 100 via, for example, a length of tubing (not shown) interconnecting the flow regulator 340 and the sidearm 122. Thus the flow regulator 340, tubing and sidearm 122 can form a flow path between the liquid reservoir 310 and the sheath lumen 116. The flow regulator 340 can be fabricated from multiple injection-molded pieces which are joined or fixed together to form the illustrated flow regulator 340. At least the drip chamber 346 can be formed from a transparent material so that a user may visually confirm the presence of saline in the drip chamber 346.

The reservoir chamber 342 defines an internal lumen 344 that is in fluid communication with an internal lumen 348 defined by the drip chamber 346. The inlet port 370 can comprise a spike 372 that can be directly coupled to a liquid reservoir 310 (FIG. 4B) such as a saline bag. The spike 372 defines an internal channel 374 forming a flow passage for liquid between the liquid reservoir 310 and the lumen 344. Other suitable connectors, such as luer fittings, can be used in place of the spike 372 in other embodiments.

The flow restriction 350 can be configured to provide a fixed and predetermined liquid flow rate at a desired flow rate for treating an HAS. The flow restriction 350 can comprise a restricted passage with an orifice having a predetermined effective opening that is sized to provide the desired liquid flow rate. As illustrated, the flow restriction 350 comprises a channel 352 having an inlet orifice 354 and an outlet orifice 356 and defining a flow passage 358 between the lumens 344, 348. The flow passage 358 can be sized to provide an appropriate fixed and predetermined treatment flow rate as discussed herein, e.g., 5-60 cc/hour, 5-40 cc/hour, 10-30 cc/hour, 15-25 cc/hour, or about 20 cc/hour. For example, the cross-sectional area of the flow path through the flow regulator 340 can decrease from that of the lumen 344 to that of the flow passage 358 to provide a desired treatment flow rate. The flow passage 358 through the channel 352 can have a fixed size. Optionally, the outlet orifice 356 can have a diameter of approximately 0.5 mm. In another variation, the channel 352 can be a rigid member such as a rigid tube or a rigid (e.g. glass) capillary tube.

The flow restriction 350 can further comprise a flow restrictor member 360 positioned in the channel 352 to provide an appropriate fixed and predetermined treatment flow rate as discussed herein, e.g., 5-60 cc/hour, 5-40 cc/hour, 10-30 cc/hour, 15-25 cc/hour, or about 20 cc/hour. As illustrated, the flow restrictor member 360 can comprise a channel restrictor 362 inserted into the inlet orifice 354 of the channel 352 and extending at least partially into the flow passage 358. The channel 352 and channel restrictor 362 can be sized to provide a gap therebetween for the passage of fluid. The gap can be on the order of 0.025 mm. The gap can form an annulus extending around the channel restrictor 362 and bordered by the channel. Optionally the annulus can include an annular gap between the channel restrictor 362 and the channel 352 of approximately 0.025 mm.

The channel restrictor 362 can comprise a first portion 364 that is inserted into the flow passage 358 and a second portion 366 that is bent with respect to the first portion 364 to hold the restrictor 362 in place in the flow passage 358. The length of the first portion 364, i.e. how far the channel restrictor 362 protrudes into the flow passage 358, can be selected to control the flow rate. As a general rule, increasing the length of the first portion 364 will decrease the flow rate. The cross-sectional size of the first portion 364 can also affect the flow rate. Thus, both the cross-sectional size and length of the first portion 364 of the channel restrictor 362 may be used to control the flow rate through the flow passage. Optionally, the channel restrictor 362 can comprise a wire that is bent to form the first portion 364 and second portion 366. The first portion 364 can itself be slightly bent to impart a springlike characteristic to the first portion that helps to retain the restrictor 362 in the flow passage 358.

Figure 4F:
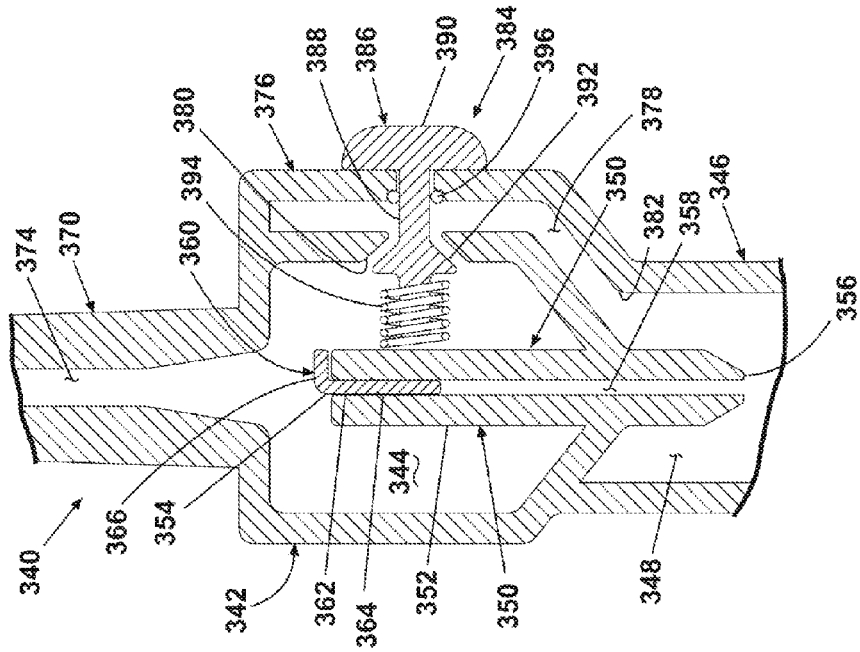
FIG. 4F is a detailed view of FIG. 4E with a bypass controller in an open position.
Figure 4E:
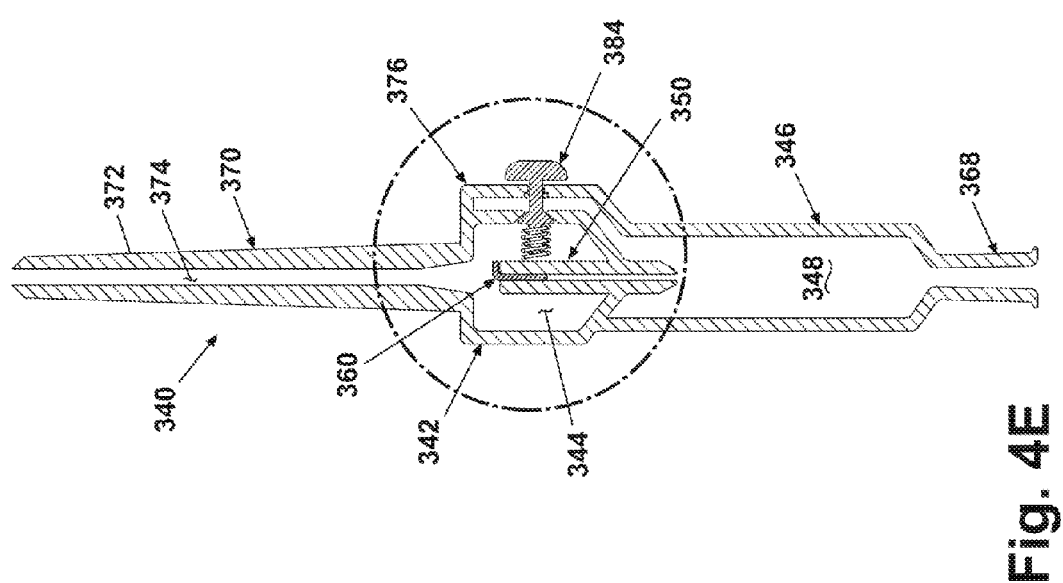
FIG. 4E is a schematic view of another embodiment of a flow regulator usable with the liquid source of FIG. 4B with a bypass controller in a closed position.
Figure 5:
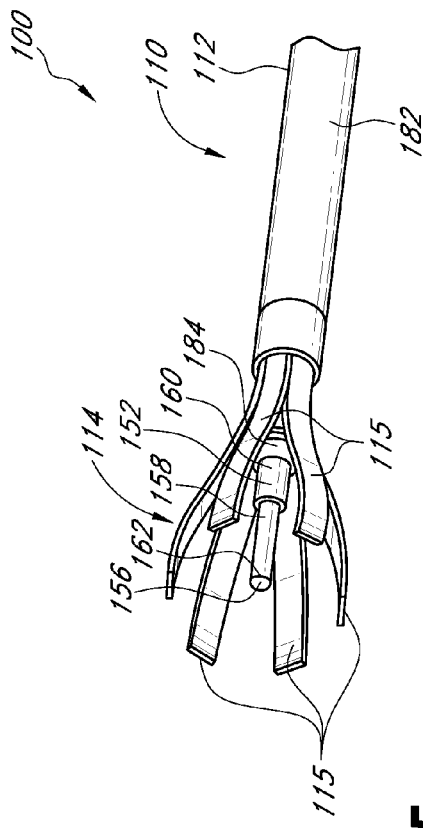
FIG. 5 is a detailed perspective view of a distal portion of another embodiment of the sheath.

FIGS. 4E-F depict an alternate embodiment of the flow regulator 340, which can be similar in structure, use and function to the flow regulator 340 of FIGS. 4C-D, except as further described herein. In the flow regulator 340 of FIGS. 4E-F, a bypass chamber 376 is provided for selectively bypassing the flow restriction 350. The bypass chamber 376 defines a bypass channel 378 that fluidly communicates with the lumen 344 of the reservoir chamber 342 via an inlet orifice 380 and with the lumen 348 of the drip chamber 346 via an outlet orifice 382.

By bypassing the flow restriction 350 using the bypass chamber 376, a higher flow rate can be provided than that used during delivery of energy to a HAS to flush out the system 100. Flushing the system 100 may be done before a treatment procedure to rid the system 100 of any air bubbles by filling the system 100 with fluid or during a treatment procedure to remove a blockage from the system 100.

A bypass controller 384 can be provided that selectively opens one of the orifices 380, 382 to allow fluid flow through the bypass channel 378 to flush the system 100. As illustrated in FIG. 4F, the bypass controller 384 selectively opens that orifice 380 to allow fluid from the reservoir chamber to enter the bypass chamber 376 and pass through the open outlet orifice 382 and into the drip chamber 346. The bypass controller 384 can comprise a spring-biased valve 386 having a valve stem 388 with a push button head 390 at one end and a closure element 392 spaced from the push button head 390. The valve 386 is biased to a closed position, shown in FIG. 4E, in which the closure element 392 is seated against the orifice 380 and prevents fluid flow into the bypass channel 378, by a spring 394 positioned between the closure element 392 and the channel 352. The valve 386 can be moved to an open position, shown in FIG. 4F, in which the closure element 392 is spaced from the orifice 380, permitting fluid flow into the bypass channel 378, by depressing the push button head 390. A sealing element 396 can be placed between the valve stem 388 and the exterior wall of the bypass chamber 376 to prevent fluid leakage.

In a variation of the embodiment of FIGS. 4C and 4D, the channel 352 can comprise a capillary tube that utilizes capillary action to pass liquid through the channel 352. The channel 352 comprising a capillary tube can be sized to provide an appropriate fixed and predetermined treatment flow rate with or without the need for the flow restrictor member 360.

FIGS. 5-7B depict another embodiment of the system 100, which can be similar in structure, use and function to any of the variations of the systems 100 of FIGS. 1-4, except as further described herein. In the system 100 of FIG. 5, the distal tip portion 114 of the shaft 112 of the sheath 110 comprises a number of radially expanded or expandable members 115. The expandable members 115 preferably comprise strips of an appropriate metallic or polymeric material having a springlike bias toward a radially expanded configuration. When the expandable members 115 are in the expanded configuration (FIGS. 5-7A), the members 115 surround and are radially spaced from the emitting tip 162 of the optical fiber 152 (or other light delivery device). The tip 162 is preferably spaced proximally from the distal end of the expandable members 115 by a distance X of 2 mm to 20 mm. The fiber tip 162 can therefore remain disposed within the set of expandable members 115 during treatment, and the expandable members 115 can protect the hot fiber tip 162 from contact with the inner wall of the vein or other target HAS (and vice versa).

Figure 6:
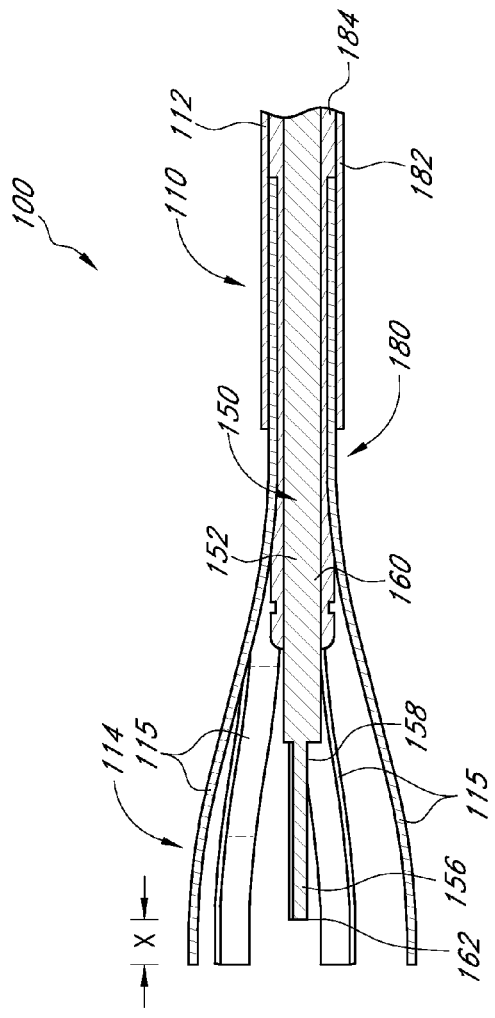
FIG. 6 is a side sectional view of the sheath of FIG. 5.

As can be seen from FIGS. 6 and 7B, the members 115 are preferably retractable into the shaft 112 by drawing an inner tube assembly 180 proximally into a surrounding outer tube 182. The outer tube 182 forces the members 115 radially inward as the inner tube assembly 180 is drawn into the lumen of the outer tube 182. As depicted, the inner tube assembly 180 can comprise an inner tube 184, and the expandable members 115, which are preferably attached to the distal end of the inner tube 184. The inner tube 184 receives the optical fiber 152 or other light delivery device within its inner lumen, in a manner similar to the lumen 116 of the shaft 112 shown in FIGS. 1-4. Preferably, the lumen of the inner tube 184 is sized to accommodate a space for liquid flow between the inner tube 184 and the fiber 152, to facilitate optional delivery of liquid during treatment with the system 100 of FIGS. 5-7B, as described above in connection with the embodiments of FIGS. 1-4.

The system 100 of FIGS. 5-7B can be used in a manner generally similar to the systems 100 of FIGS. 1-4, except as follows. With the expandable members 115 in the retracted configuration as shown in FIG. 7B, the sheath 110 can be delivered over a guidewire (or otherwise) to the desired treatment location. Once the sheath 110 is in position, the guidewire can be withdrawn and the members 115 can be expanded by moving the outer and inner tubes 182, 184 relative to each other such that the members 115 move distally beyond the end of the outer tube 182. Free of the constraint of the outer tube 182, the members 115 then self-expand to the expanded configuration shown in FIGS. 5-7A. The optical fiber 152 or other light delivery device can then be advanced through the hub 120 and down the shaft 112 and positioned so that the tip 162 is disposed within the members 115, and spaced proximally by the distance X from the distal ends of the members 115. As discussed above, the fiber 152 can include a mark (or a projection such as a flange, slidable collar or "donut") appropriately spaced from the tip 162 to indicate proper positioning of the tip 162 relative to the expanded members 115 upon alignment of the mark with a reference point such as the proximal edge of the hub 120.

Once the tip 162 is in position, the treatment can proceed as discussed elsewhere herein. After completion of the treatment, the members 115 can be retracted by drawing the inner tube assembly 180 into the outer tube 182. The system 100 can then be withdrawn from the patient in the usual manner.

Figure 8A:
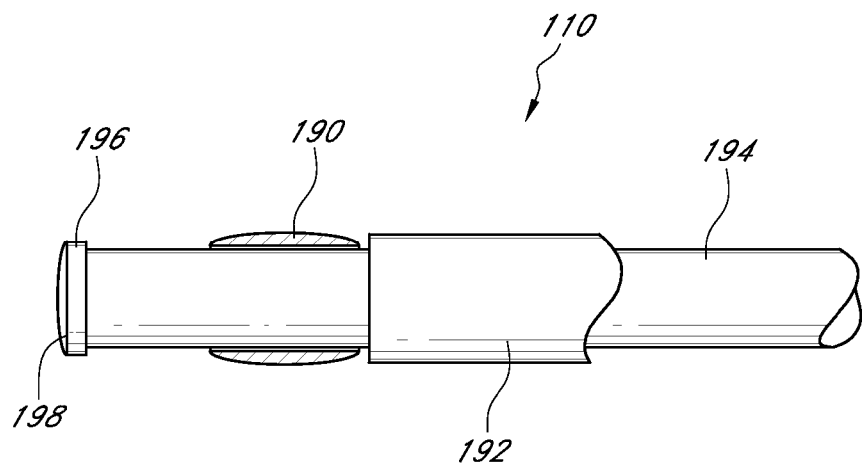
FIG. 8A is a side view of another embodiment of the sheath.
Figure 8B:
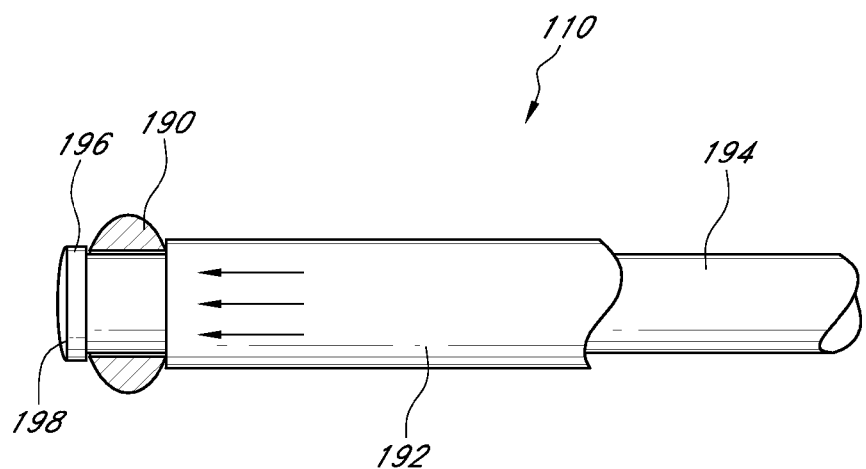
FIG. 8B is a side view of the sheath of FIG. 8A, with an expandable collar thereof in the expanded configuration.

FIGS. 8A-8B depict the distal portion of an alternative embodiment of a sheath 110 for use with the system 100. The sheath 110 of FIG. 8 includes an expandable collar 190 which is expandable via compression created by interaction of an outer tube 192 and an inner tube 194. The tubes 192, 194 are slidable relative to each other so that the collar 190 can be compressed (FIG. 8B) between the distal end of the outer tube 192 and a flange 196 fixed to the distal end of the inner tube 194. The optical fiber 152 or other light delivery device can be received in an inner lumen of the inner tube 194. Preferably, during use, the collar 190 is in the expanded configuration and the light emitting tip 162 of the fiber 152 is positioned close to (e.g., about 2 mm to 20 mm proximal of) a distal opening 198 of the inner tube 194. The expanded collar 190 prevents contact between the hot fiber tip and the HAS wall during treatment. If desired, a liquid flow can be provided via the inner lumen of the inner tube 194 (around the fiber 152) during application of light/laser energy, as discussed elsewhere herein. In various embodiments, the expandable collar 190 can comprise a fluid filled annular balloon, or an annular, solid member formed from a compliant and compressible polymer material, or the like.

Figure 9A:
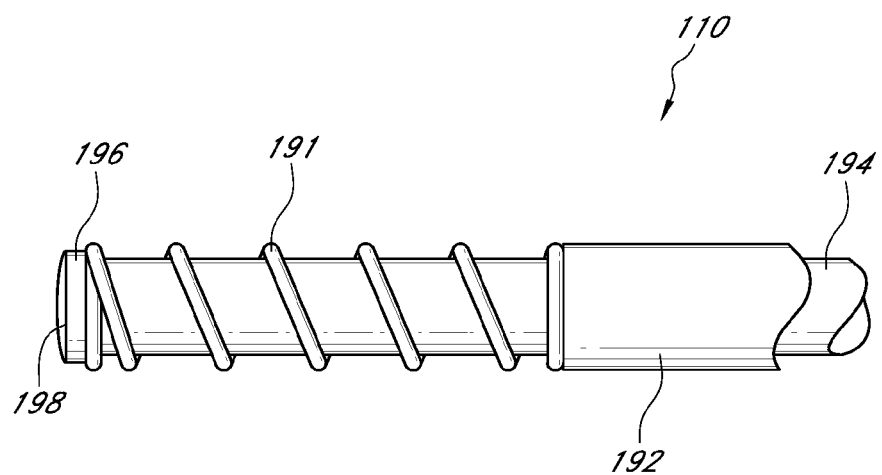
FIG. 9A is a side view of another embodiment of the sheath.
Figure 9B:
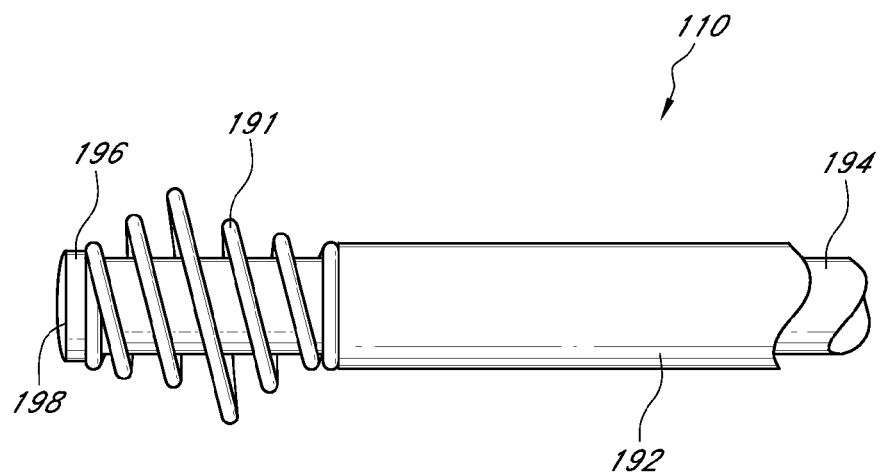
FIG. 9B is a side view of the sheath of FIG. 9A, with an expandable spring thereof in the expanded configuration.

FIGS. 9A-9B depict another embodiment of a sheath 110 which can be similar in structure, function and use to the sheath 110 of FIGS. 8A-8B, except for the use of an expandable coil 191 in place of the expandable collar 190. The coil 191 can alternatively comprise a preshaped memory coil which can be deployed by a technique other than the compression depicted in FIGS. 9A-9B, such as by retraction of an overlying sheath, or a coil formed from power-induced or resistive-heating-induced memory material such as Nitinol or compatible materials, to facilitate expansion of the coil to its "remembered" expanded configuration by passing an electrical current through the coil through electrical leads (not shown) connected thereto.

Figure 10A:
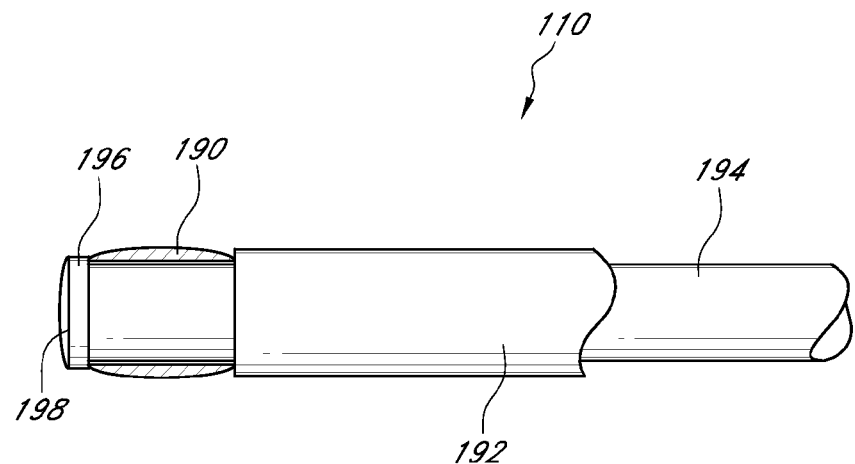
FIG. 10A is a side view of another embodiment of the sheath.
Figure 10B:
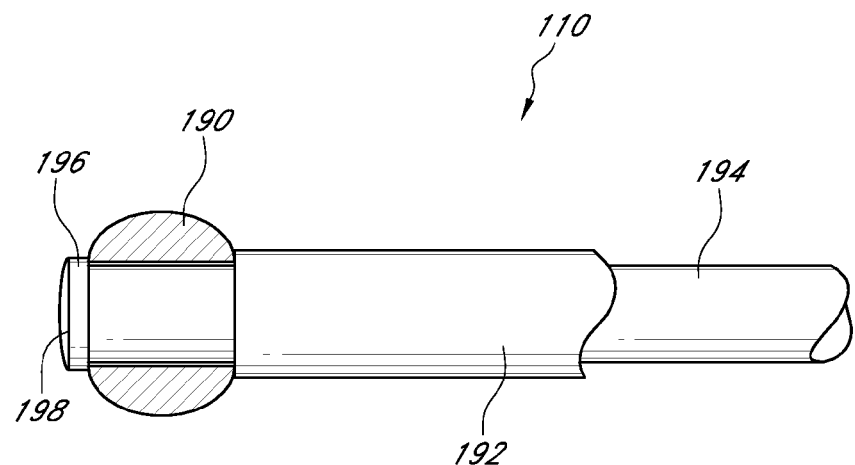
FIG. 10B is a side view of the sheath of FIG. 10A, with a balloon thereof in the inflated configuration.

FIGS. 10A-10B depict another embodiment of a sheath 110 which can be similar in structure, function and use to the sheath 110 of FIGS. 8A-8B, except that the expandable collar 190 is a balloon which is inflatable and deflatable via one or more inflation passages (not shown) disposed in the outer tube 192. In this embodiment, the outer tube 192 and inner tube 194 are preferably not movable relative to each other. In another embodiment, the collar 190 is a mass of compliant, hydrophilic material (e.g. a sponge) that can be expanded by supplying a fluid to it from conduit(s) formed in the sheath 110.

Figure 11:
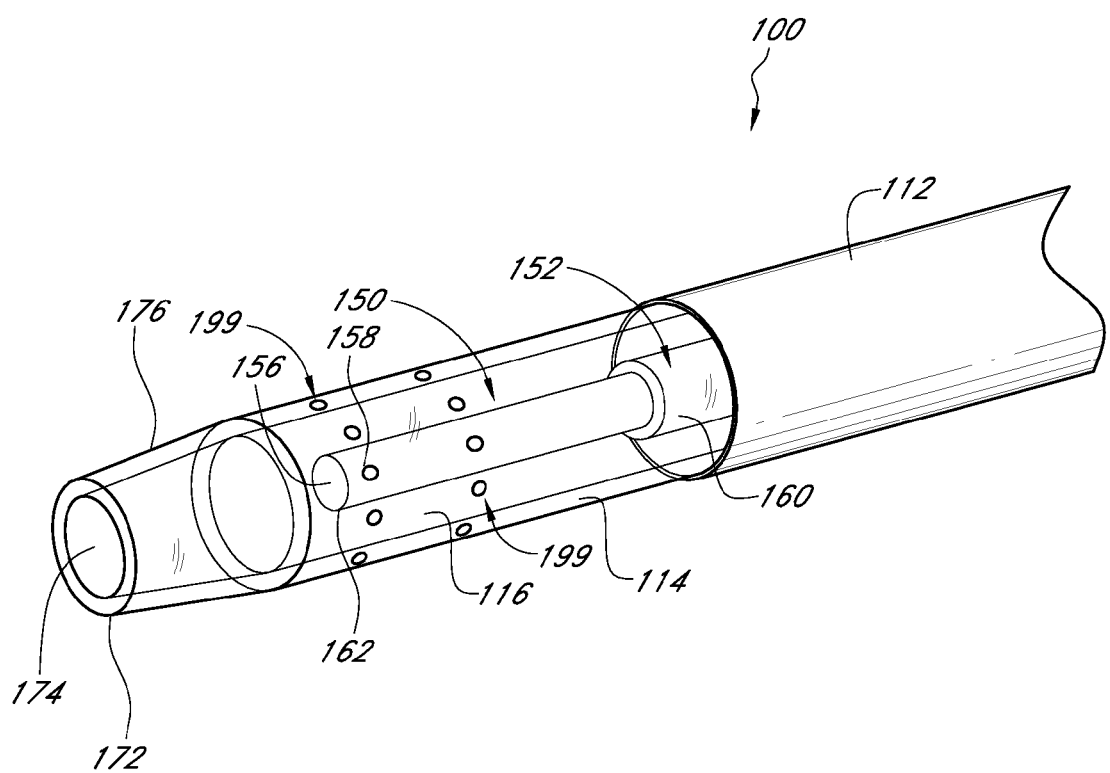
FIG. 11 is a perspective view of another embodiment of the sheath of FIG. 2.

FIG. 11 depicts another embodiment of the system 100, which can be similar in structure, function and use to the systems 100 shown in FIGS. 1-4, except as further discussed below. In this embodiment, the distal tip portion 114 of the sheath 110 contains one or more holes 199 in its sidewall. Where employed, the holes 199 communicate hot or boiling liquid outward to the HAS at location(s) along the length of the sheath tip 114. The holes 199 can be arranged in one or more circumferential bands as depicted. The size of the holes 199, the number of holes in each band, the number of bands, and the position of the bands relative to the distal end of the sheath tip 114 can be varied to control the length of the treatment zone. The holes 199 provide a pressure relief of the hot and/or boiling liquid inside the sheath 110, to reduce the pressure and velocity of the fluid ejected through the opening 174 in the distal end of the tip portion 114 during treatment.

FIGS. 12A and 12B depict another embodiment of the system 100, which can be similar in structure, function, and use to the systems 100 shown in FIGS. 1-3, except as further discussed below. In this embodiment, the distal tip portion 114 of the shaft 112 preferably has a generally constant inner and outer diameter and is transparent to, or otherwise highly transmissive of, the wavelength of light emitted via the fiber tip 162. The fiber tip 162 includes a shaped surface 200 having at least one face or portion oriented non-perpendicularly to the longitudinal axis A of the optical fiber 152. The shaped surface 200 can be configured in accordance with a desired light dispersion pattern. For example, angle refraction physics and/or other scientific principles governing light behavior can be employed to determine a desired configuration for the shaped surface 200 and, thereby, control the emission of light from the light delivery device 150 to the HAS walls, the sheath distal tip portion 114, and/or delivered liquid.

In the illustrated embodiment, the shaped surface 200 has a generally conical configuration that terminates at a point coincident with the distal end of the optical fiber 152. The fiber tip 172 with the conical shaped surface 200 provides for more radial dispersion of the light as compared to, for example, a blunt end fiber tip 162, such as the fiber tip 162 shown in FIG. 3. In other words, more of the light is directed radially toward the adjacent HAS walls rather than axially into the lumen of the HAS located distally of the system 100. Other configurations are within the scope of the present disclosure. For example, the angled surface 200 can have a generally conical configuration that terminates proximally of the most distal end of the optical fiber 152 such that the fiber tip 162 terminates at a blunt surface orthogonal to the longitudinal axis of the optical fiber 152 and having a transverse sectional area less than that of portion of the core 156 covered by the jacket 160, which can sometimes be referred to as a frustoconical configuration. Other contemplated configurations include pyramidal, prismatic, and spherical surfaces.

Factors to consider when determining the configuration of the shaped surface 200 include the configuration and material of the distal tip portion 114 of the sheath 110. In some variations of this embodiment, the shape and material of the distal tip portion 114 can affect the path of the light emitted from the fiber tip 162. Conversely, the configuration and material of the distal tip portion 114 can be selected based on a predetermined configuration of the shaped surface 200. The shape and material of the distal tip portion 114 shown in FIGS. 12A and 12B are provided for illustrative purposes and are not intended to limit the present disclosure. The optical fiber 152 with the tip 162 having the shaped surface 200 can be utilized with any suitable sheath 110, including any of the sheaths 110 in the embodiments of FIGS. 1-11.

FIGS. 13-16 depict other embodiments of the system 100, which can be similar in structure, function, and use to the systems 100 shown in FIGS. 1-3, except as further discussed below. Each of the embodiments of FIGS. 13-16 can comprise a distally closed sheath 110 as depicted; differences between each of the embodiments of FIGS. 13-16 and FIGS. 1-3 are described below.

Figure 13:
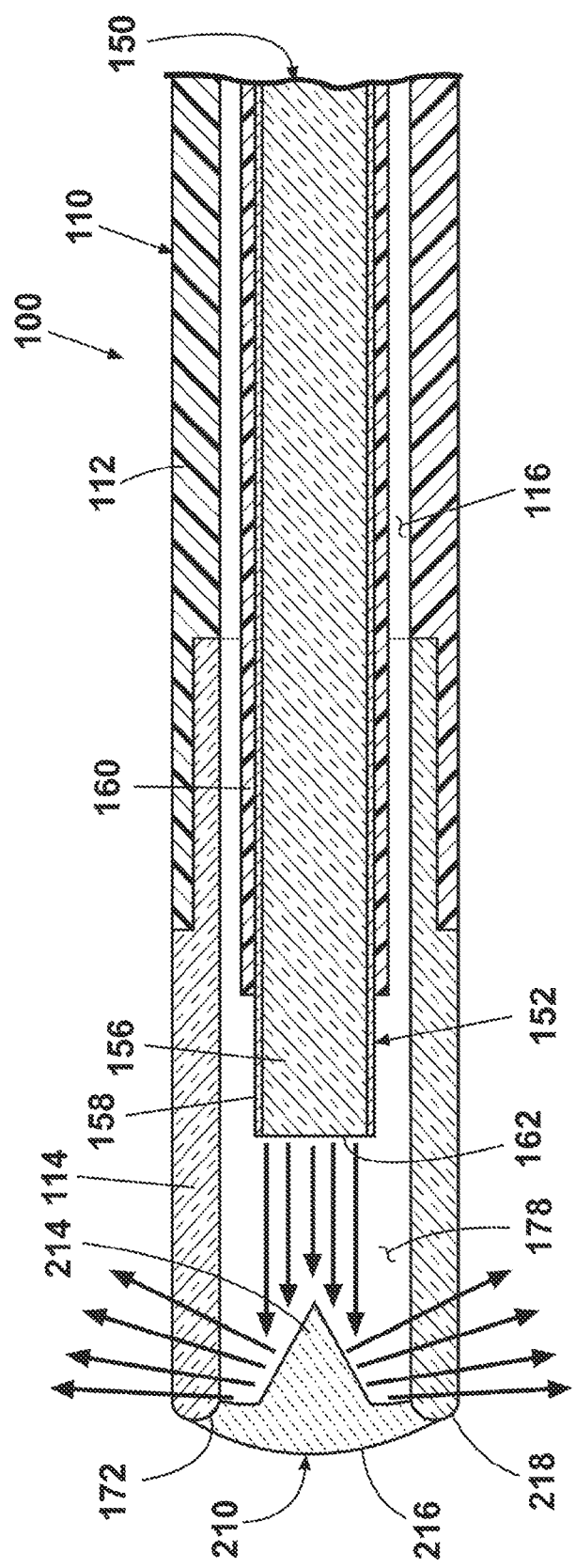
FIG. 13 is a side sectional view of a distal portion of another embodiment of the sheath with the light delivery device of FIG. 2.

In the embodiment of FIG. 13, a plug 210 located at the open distal end 172 of the distal tip portion 114 effectively closes the distal end of the sheath 110. The distal tip portion 114 is transparent to, or otherwise highly transmissive of, the wavelength(s) of light emitted via the fiber tip 162, while the plug 210 is substantially not transmissive or substantially opaque to the wavelength(s) of light. Any suitable material or combination of materials can constitute the plug 210, and one suitable material for the plug 210 is a metal.

The plug 210 includes a reflective body 214 extending proximally toward and aligned with the direction of light emission from the fiber tip 162. The reflective body 214 reflects the light emitted from the fiber tip 162 and disperses the light radially outward toward the HAS walls. Additionally, the reflective body 214 effectively disperses or spreads the light beam, thereby decreasing the flux density of the light relative to that of the light as it exits the fiber tip 162, which can contribute to minimizing blood boiling effects and coagulation problems, such as deep vein thrombosis. The reflective body 214 can be configured to reflect the light radially, radially and proximally, and/or radially and distally. In the illustrated embodiment, the reflective body 214 has a generally conical configuration, which provides 360-degree radial and radial/proximal reflection of the light from the fiber tip 162. The shape of the reflective body 214 shown in FIG. 13 is provided as an example; other configurations of the reflective body 214 are within the scope of the invention. Other examples of the reflective body 214 include, but are not limited to, pyramidal, prismatic, and spherical or hemispherical bodies. Further, the surface of the reflective body 214 can be treated, such as by polishing or coating, to provide a surface texture having a desired reflectivity.

In the illustrated embodiment, the plug 210 and the distal end 172 of the distal tip portion 114 both have a curved distal surface 216, 218 that together form a rounded distal end of the sheath. The rounded configuration facilitates insertion of the system 100 into a guide sheath or into the HAS.

The system 100 of FIG. 13 can employ any suitable light delivery device and is not limited to the light delivery device with the optical fiber 152 having the blunt fiber tip 162. For example, the system 100 can alternatively use the optical fiber 152 of FIGS. 12A and 12B having the fiber tip 162 with the shaped surface 200, which can further contribute to dispersion of the light beam. Other optical fibers 152 described and not described in this application can be used with the system 100 of FIG. 13.

In a variation of the embodiment of the system 100 of FIG. 13, the sheath 110 can include one or more ports, such as a port formed in the distal tip portion 114, for fluidly communicating the fluid delivery space 178 with the HAS lumen to render the system 100 suitable for fluid delivery into the HAS lumen. One or more such ports can additionally or alternatively be located in the plug 210.

In another variation, the plug 210 or a portion thereof can be formed of a material at least partially transmissive of the wavelength of light emitted via the fiber tip 162 such that a portion of the light reflects from the reflective body 214 and a portion transmits through the plug 210. For example, the reflective body 214 can be made opaque while the rest of the plug 210 can be made transmissive.

In yet another variation of the embodiment of the system 100 of FIG. 13, one or both of the plug 210 and the distal tip portion 114 can be removable from the shaft 112. Optionally, the plug 210 and/or the distal tip portion 114 can be modular or replaceable with other types of plug 210 and distal tip portion 114. The removable and replaceable features of the distal tip portion 114 and structures associated therewith can be applied to any of the embodiments of the system 100 described in this application.

Figure 14A:
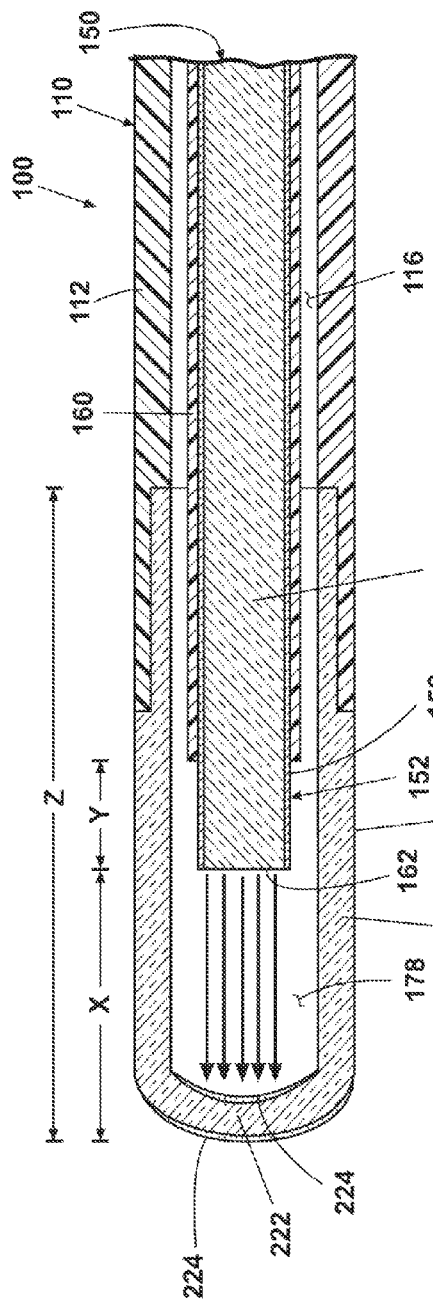
FIG. 14A is a side sectional view of a distal portion of another embodiment of the sheath with the light delivery device of FIG. 2.

In the embodiment of the system 100 in FIG. 14A, the distal tip portion 114 of the sheath 110 comprises a cylindrical region 220 terminating at a rounded distal end 222 that distally closes the sheath 110. The distal tip portion 114 is transparent to, or otherwise highly transmissive of, the wavelength(s) of light emitted via the fiber tip 162, except that the rounded distal end 222, or at least a portion of the rounded distal end 222, includes a light absorbing body 224 arranged within the path of the light emitted from the fiber tip 162. The light absorbing body 224 prevents or at least inhibits transmission of light therethrough, and the light absorbed by the body 224 heats the body 224, which in turn heats the HAS walls in contact with (and/or nearby) the body 224, as described in more detail below. The light absorbing body 224 can have any suitable form, such as a material deposited, coated, or otherwise attached to the rounded distal end 222 and can be located on a proximal and/or a distal surface of the rounded distal end 222. In the illustrated embodiment, the light absorbing body 224 is provided on both the proximal and distal surfaces of the rounded distal end 222. The material of the light absorbing body 224 is highly absorbent of the wavelength of light emitted via the fiber tip 162 such that the light heats the material. As a result of this configuration, light emitted from the fiber tip 162 can both be absorbed by the light absorbing body 224 and transmit through other areas of the distal tip portion 114. The light absorbed by the light absorbing body 224 heats the light absorbing body 224, which can thereby conductively heat the HAS walls in contact with the light absorbing body 224 (and/or otherwise heat the nearby HAS walls). The light transmitted through the distal tip portion 114 can heat the HAS walls via light energy transmission directly to the HAS walls.

The fiber 152 and the distal tip portion 114 can have any suitable relative size and positioning. As an example, a distance Y of the optical fiber 152 between the jacket 160 and the fiber tip 162 can be about 1-2 mm, the distance X between the fiber tip 162 and the most distal portion of the rounded distal end 222 can be about 3-5 mm, and a distance Z corresponding to the length of the distal tip portion 114 can be about 5-10 mm.

The system 100 of FIG. 14A can employ any suitable light delivery device and is not limited to the light delivery device with the optical fiber 152 having the blunt fiber tip 162. For example, the system 100 can alternatively use the optical fiber 152 of FIGS. 12A and 12B having the fiber tip 162 with the shaped surface 200. In such a variation, the light absorbing body 224 can be adapted according to the direction of light emission from the shaped surface 200 of the fiber tip 162. For example, a portion of the light absorbing body 224 can be extended to the cylindrical region 220 of the distal tip portion 114. Other optical fibers 152 described and not described in this application can be used with the system 100 of FIG. 14A.

Figure 14B:
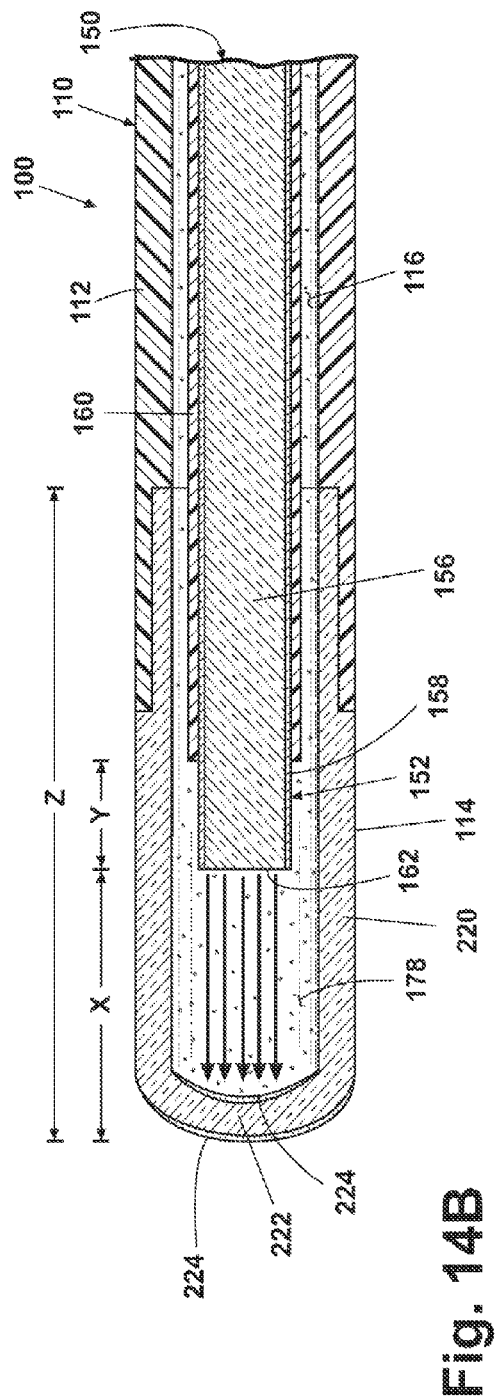
FIG. 14B is a side sectional view of a distal portion of the embodiment of the sheath shown in FIG. 14A with a light scattering material located inside the sheath.

In a variation of the embodiment of the system 100 of FIG. 14A, a light scattering material located in the space 178 between the optical fiber 152 and the distal tip portion 114, as illustrated in FIG. 14B, can facilitate transmission of the light to the light absorbing body 224 and through the distal tip portion 114. The light scattering material can be a liquid, a solid, or combination of a liquid and a solid. For example, the light scattering material can be a translucent liquid with a reflective solid particulate suspended in the liquid. For such a light scattering material, the liquid transmits the light for reflection by the solid particulate. The aggregate effect of the suspended particulate is to scatter the light incident on the scattering material from the fiber 152. This can include scattering the light radially, radially and distally, or radially and proximally.

In another variation of the embodiment of the system 100 of FIG. 14A, the light absorbing body 224 can be a body separate from and closing the distal tip portion 114, similar to the manner in which the plug 210 closes the distal tip portion 114 in the embodiment of FIG. 13. Further, the light absorbing body 224 and the rounded distal end 222 need not be rounded; other configurations, such as blunt and tapered, are within the scope of the invention.

In yet another variation of the embodiment of the system 100 of FIG. 14A, the sheath 110 can include one or more ports, such as a port formed in a sidewall of the distal tip portion 114, for fluidly communicating the fluid delivery space 178 with the HAS lumen. One or more ports can additionally or alternatively be located in the light absorbing body 224.

In the embodiment of the system 100 in FIG. 15, the distal tip portion 114 of the sheath 110 comprises the cylindrical region 220 terminating at the rounded distal end 222 that distally closes the sheath 110, similar to the sheath 110 in the embodiment of the device 100 shown in FIG. 14A. The distal tip portion 114 of the sheath 110 in FIG. 15, however, lacks the light absorbing body 224 of FIG. 14A. Instead, the entire distal tip portion 114 can transmit the light emitted from the fiber tip 162. The cylindrical region 220 and the rounded distal end 222 can be integrally formed, as illustrated, or formed of separate bodies joined in any suitable manner. In one variation, the rounded distal end 222 can be formed as a separate body removably coupled to the cylindrical region 220.

The system 100 of FIG. 15 includes the light delivery device 150 having the shaped surface 200 at the fiber tip 162 shown in the embodiment of FIGS. 12A and 12B and described above in detail. The system 100 of FIG. 15, however, can employ any suitable light delivery device and is not limited to the light delivery device with the optical fiber 152 having the fiber tip 162 with the shaped surface 200. For example, the system 100 can alternatively use the optical fiber 152 having the blunt fiber tip 162. Other optical fibers 152 described and not described in this application can be used with the system 100 of FIG. 15.

As described above for variations of the embodiment of FIG. 14A, variations of the embodiment of the system 100 in FIG. 15 can include other features, including a light scattering material in the space 178 between the optical fiber 152 and the distal tip portion 114 and/or one or more ports in the distal end or sidewall of the distal tip portion 114. In another variation, the rounded distal end 222 can have a configuration other than rounded, as discussed below with respect to the embodiment of the system 100 in FIG. 16.

The embodiment of the system 100 in FIG. 16 can be similar to the embodiment of the system 100 in FIG. 15, except that the distal end 222 has a generally conical configuration rather than a rounded configuration. The distal end 222 shown in FIG. 16 comprises a tapered region 230 that terminates at a closed tip 232. The tapered region 230 can be configured to transmit the light emitted from the fiber tip 162 in a desired pattern. For example, the tapered region 230 can be designed to refract the light distally and radially, completely radially, or proximally and radially. In the illustrated embodiment, the shape of the tapered region 230 effectively redirects the light emitted from the fiber tip 162 to provide more radial transmission of the light to the adjacent HAS walls, as indicated by the radially oriented arrows in FIG. 16, than would be present without the tapered region 230. The tapered region 230 can have any suitable configuration, and, as one example and as illustrated, the tapered region 230 can be angled differently than the shaped surface 200 of the fiber tip 162. As another example, the tapered region 230 can be angled at the same angle employed with the shaped surface 200 of the fiber tip 162.

The system 100 of FIG. 16 includes one suitable manner of joining the distal tip portion 114 and the shaft 112 of the sheath 110 different from that shown in the previous embodiments. While the distal end portion 114 and the shaft 112 can be joined in any suitable manner, a heat shrinkable sleeve 240 joins the distal tip portion 114 and the shaft 112 of the system 100 illustrated in FIG. 16. An adhesive, such as an epoxy, can be employed independently or in combination with the sleeve 240 to facilitate joining the distal tip portion 114 and the shaft 112.

The system 100 of FIG. 16 includes the light delivery device 150 having the shaped surface 200 at the fiber tip 162 shown in the embodiment of FIGS. 12A and 12B and described above in detail. The system 100 of FIG. 16, however, can employ any suitable light delivery device and is not limited to the light delivery device with the optical fiber 152 having the fiber tip 162 with the shaped surface 200. For example, the system 100 can alternatively use the optical fiber 152 having the blunt fiber tip 162. Other optical fibers 152 described and not described in this application can be used with the system 100 of FIG. 16.

In a variation of the embodiment of the system 100 of FIG. 16, the tip 232 of the tapered region 230 can be opened rather than closed. The opened tip 232 can facilitate delivery of fluid from the fluid delivery space 178 while still redirecting the light emitted from the fiber tip 162 and preventing contact of the fiber tip 162 with the HAS walls. As an alternative or addition, the distal tip portion 114 can include one or more fluid ports in the distal end or sidewall of the tip portion 114, as described above with respect to other embodiments. In another variation of the system 100 of FIG. 16, the system 100 can include a light scattering material in the space 178 between the optical fiber 152 and the distal tip portion 114, as described above for the embodiment of FIG. 14A.

FIGS. 17A-20B depict other embodiments of the light delivery device 150, which can be similar in structure, function, and use to the light delivery devices 150 shown in FIGS. 1-16, except as further discussed below.

Figure 17A:
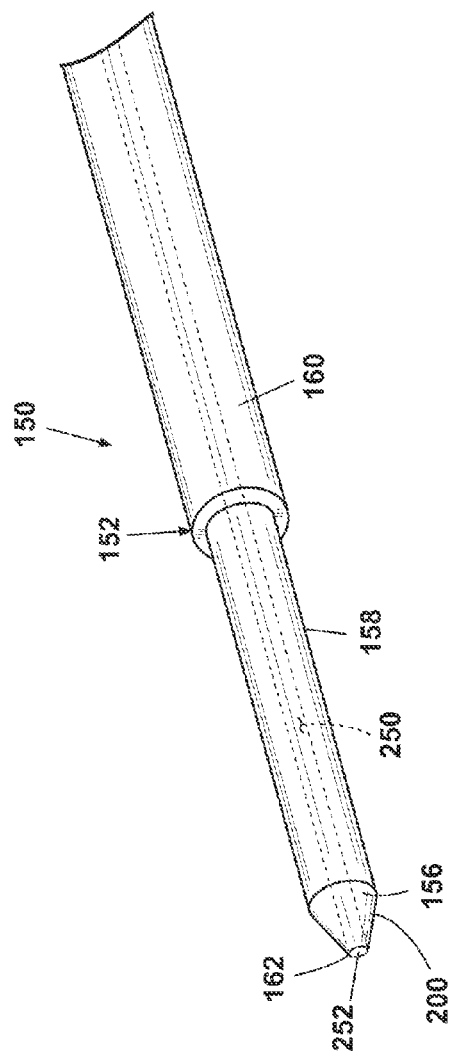
FIG. 17A is a perspective view of a distal portion of another embodiment of the light delivery device.
Figure 17B:
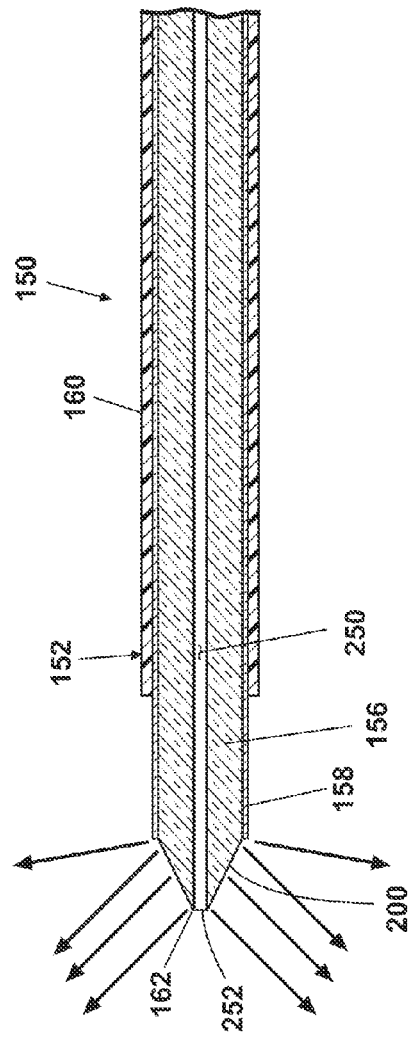
FIG. 17B is a side sectional view of the light delivery device of FIG. 17A.

The light delivery device 150 of FIGS. 17A and 17B can be similar to the light delivery device 150 in the embodiment of FIGS. 12A and 12B, except that the light delivery device 150 of FIGS. 17A and 17B includes a lumen 250 formed in the optical core 156 of the optical fiber 152 and terminating at a distal opening 252 at the fiber tip 162. While the lumen 250 can have any suitable size and cross-sectional shape, in one example, the optical fiber 152 can have an outer diameter in a range of about 300-1000 μm, and the lumen 250 can have a circular cross-section with an inner diameter in a range of about 300-600 μm. Further, the fiber tip 162 of the light delivery device 150 can include any desired configuration for the shaped surface 200 and is not limited to the generally conical shape shown in FIGS. 17A and 17B. For example, the fiber tip 162 can be prismatic, rounded, etc., according to a desired light emission pattern. Alternatively, the fiber tip 162 can be blunt.

In one variation of the embodiment, the lumen 250 can be fluidly coupled to the sidearm 122 (FIG. 1) or other fluid source such that fluid supplied to the lumen 250 via the fluid source flows through the lumen 250 and exits the lumen 250 at the distal opening 252 for delivery to the HAS. Internal reflection of the light in the lumen 250 can heat the fluid as it flows through the lumen 250.

In another variation of the light delivery device 150 of FIGS. 17A and 17B, the internal surface of the optical core 156 forming the lumen 250 can be coated with a material to prevent internal reflection of the light in the lumen 250. Such a coating can be beneficial when using the lumen 250 for fluid delivery if heating of the fluid is not desired.

The light delivery device 150 of FIGS. 17A and 17B can be employed with any suitable sheath, including any of the sheaths 110 shown with respect to the embodiments of FIGS. 1-16 and other sheaths not illustrated or described in this application, and used in a manner generally similar to that described above for the system 100 of FIGS. 1-3.

Embodiments of the light delivery device 150 illustrated in FIGS. 18-20B can be employed without a sheath to treat an HAS as described elsewhere herein. These embodiments are designed to prevent direct contact between the HAS walls and the fiber tip 162. Each of these embodiments, particularly the differences between them and the embodiments of the light delivery devices 150 previously presented are described below.

Figure 18:
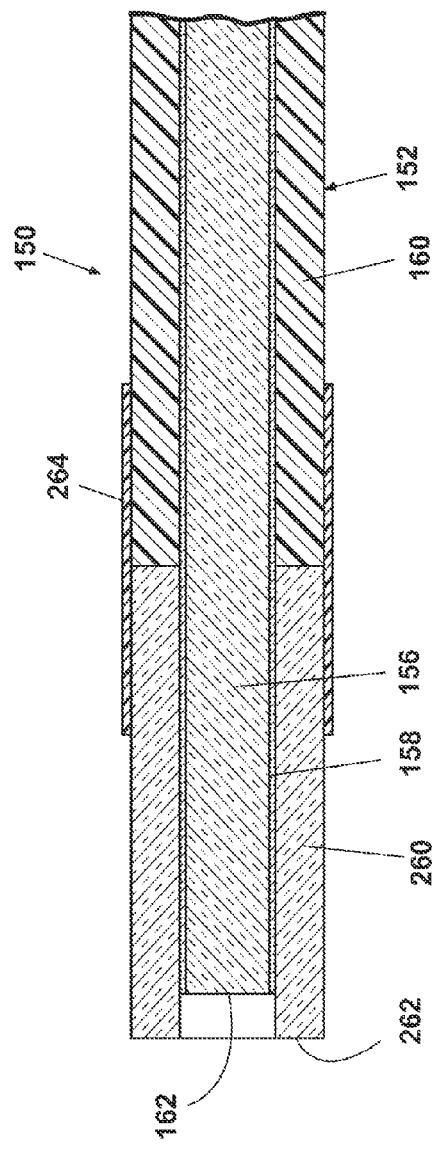
FIG. 18 is a side sectional view of a distal portion of another embodiment of the light delivery device.

The embodiment of the light delivery device 150 shown in FIG. 18 can be similar to the light delivery device 150 of the embodiment in FIGS. 1-3, except that the light delivery device 150 of FIG. 18 includes a distal tip portion 260 extending from the jacket 260 to a distal end 262 projecting beyond the fiber tip 162 a predetermined distance. The distal tip portion 260, similar to the distal tip portion 114 of the shaft 112 in previous embodiments, is transparent to, or otherwise highly transmissive of, the wavelength of light emitted via the fiber tip 162. Extension of the distal end 262 beyond the fiber tip 162 prevents contact between the HAS walls and the fiber tip 162. The distal end 262 can be blunt, as illustrated, or otherwise configured for a desired light emission pattern. The distal tip portion 260 can be coupled to the jacket 160 in any suitable manner, such as by a heat shrinkable sleeve 264 optionally combined with an adhesive, including epoxy adhesives.

Figure 19:
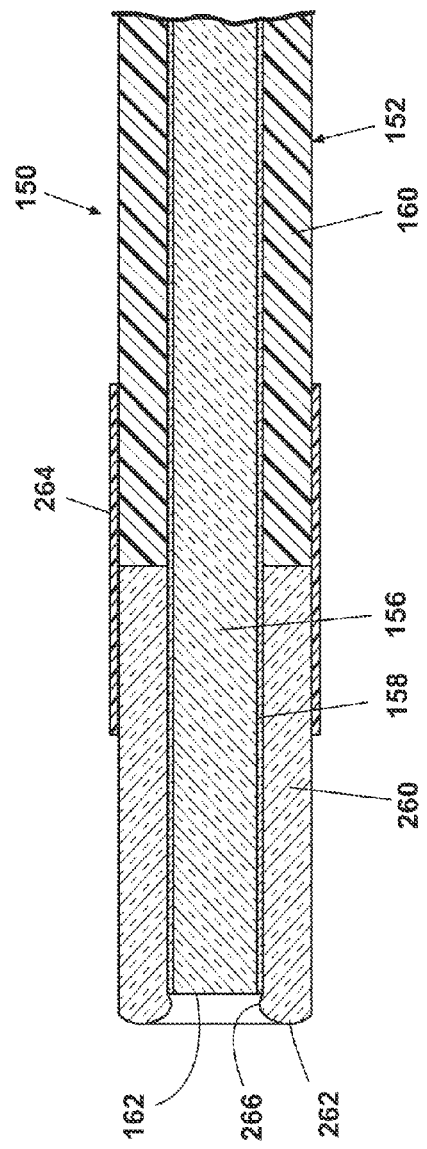
FIG. 19 is a side sectional view of a distal portion of another embodiment of the light delivery device.

The embodiment of the light delivery device 150 in FIG. 19 provides an example of modifying the distal end 262 of the distal tip portion 260. The light delivery device 150 of FIG. 19 can be otherwise similar to that of FIG. 18. The distal end 262 shown in FIG. 19 has a rounded configuration and includes an annular projection 266 extending radially inward distally of the fiber tip 162. The projection 266 inhibits inadvertent distal movement of the optical core 156 and the cladding 158 relative to the jacket 160 and the distal tip portion 260 beyond the position shown in FIG. 19, and the rounded configuration facilitates smooth insertion of the light delivery device into the HAS. While the rounded configuration can provide such a benefit, it is within the scope of the present disclosure for the distal end 262 and/or the projection 266 to be shaped otherwise.

Referring now to FIGS. 20A and 20B, another embodiment of the light delivery device 150 comprises the optical fiber 152 having the optical core 156, the cladding 158, and the jacket 160 as described above for the other embodiments of the light delivery device 150 and further includes a distal body 270 enclosing a distal portion of the optical fiber 152 including at least the fiber tip 162. In the illustrated embodiment, the distal body 270 encloses the portion of the optical core 156 not covered by the cladding 158 and the jacket 160. In a variation, the cladding 158 can extend along the portion of the optical core 156 enclosed by the distal body 270, except for the fiber tip 162. The distal body 270 can assume any suitable shape and is shown by way of example as having a tubular configuration with a rounded distal end 272.

The distal body 270 prevents direct contact between the fiber tip 162 and the HAS walls and can be transparent to, highly transmissive of, or absorbing of the wavelength of light emitted from the fiber tip 162. In one variation, the distal body 270 can contain a material, such as a fluid, a solid, or a combination fluid and solid, that absorbs the wavelength of light emitted by the fiber tip 162 such that the light energy heats the distal body 270. The heated distal body 270 conductively heats the HAS walls when in contact therewith. Alternatively or additionally, the heated distal body 270 can heat fluid in the HAS lumen, including fluid delivered by the system 100. In another variation, the distal body 270 can contain a material, such as a fluid, a solid, or a combination fluid and solid, at least partially transmissive of the light emitted from the fiber tip 162 such that the light travels through the distal body 270 to the HAS walls, thereby heating the HAS walls via light energy transmission. Optionally, the material can include reflective/scattering particles to facilitate in the dispersion of light to the HAS walls.

As stated above, the light delivery devices 150 of FIGS. 18-20B can be employed without a sheath. Each of these embodiments can include an element that precludes direct contact between the HAS walls and the fiber tip 162. For the embodiments of FIGS. 18 and 19, the projection of the distal end 262 beyond the fiber tip 162 inhibits contact between the HAS walls and the fiber tip 162. In the embodiment of FIGS. 20A and 20B, the distal body 270 provides a physical barrier between the HAS walls and the fiber tip 162. The manner of using the light delivery devices 150 of these embodiments without a sheath is substantially the same as described above for the embodiments of FIGS. 1-3, except that the process can be adapted slightly to accommodate the absence of the sheath. For example, a guide sheath can be inserted along the guide wire for purposes of introducing the light delivery device 150 and then withdrawn once the light delivery device 150 is situated in the HAS. Alternatively, the light delivery device 150 can be adapted for insertion along the guide wire such that a guide sheath or similar element is not needed. As still another alternative, the light delivery devices 150 of FIGS. 18-20B can be employed to treat an HAS (such as a vein) as described elsewhere herein, but without use of a guidewire or a sheath.

Alternatively, the embodiments of the light delivery devices 150 in FIGS. 18-20B can be used with a sheath, including the sheaths 110 shown with respect to the embodiments of FIGS. 1-16 and other sheaths not illustrated or described in this application. In such a case, the systems 100 with the light delivery device 150 of any of FIGS. 18-20B can be used in a manner generally similar to that described above for the system 100 of FIGS. 1-3.

FIGS. 21A-28 depict an alternative embodiment of the system 100, which can be similar in structure, use and function to the systems 100 shown in FIGS. 1-4A and 11-16, except as further discussed below. For each of the embodiments of FIGS. 21A-28, the system 100 is provided with a position limiter 400 which is configured to limit the position of the fiber tip 162 to a predetermined position suitable for emitting light from the optical fiber 152, which can also be termed a firing position. The firing position can comprise a position proximal of the distal end 172 of the distal tip portion 114. The position limiter 400 can be configured to assist the user in placing the fiber tip in the firing position by spacing the fiber tip 162 from the distal end 172 by the distance X of 2 mm to 20 mm, 2 mm to 10 mm, 2 mm to 8 mm, 2 mm to 5 mm, 2 mm to 4 mm, or 3 mm; or otherwise by a distance suitable to minimize, inhibit, or substantially prevent buildup of proteins, coagulum and/or carbonization on the fiber tip 162. The spacing can also be suitable to minimize, inhibit, or substantially prevent perforation of the HAS being treated (including veins in particular). The position limiter 400 is advantageous when the optical fiber 152 is inserted into the sheath 110 after the sheath 100 has been positioned in a HAS because the position limiter 400 provides tactile feedback to a user who is not able to visually determine when the fiber tip 162 reaches the firing position and further prevents the fiber tip 162 from being advanced distally beyond the firing position and into the HAS.

The position limiter 400 can be located anywhere along the length of the optical fiber 152 or the introducer sheath 110. It can be beneficial to place the position limiter nearer the fiber tip 162 or the distal tip portion 114, respectively, than the proximal end of either. Thus the distance between the position limiter 400 and the fiber tip 162 is minimized, which facilitates manufacture by minimizing the dimension requiring control during assembly of the position limiter to the fiber. With a smaller distance between the position limiter 400 and the fiber tip 162, that distance can be manufactured to a greater degree of precision and with less expense.

As illustrated, the position limiter 400 can comprise a stop configured to limit the relative movement of the optical fiber 152 within the lumen 116 when the fiber tip 162 is at the firing position or distance X. The stop can comprise cooperating structures on the optical fiber 152 and the sheath 110 that are configured to prevent the insertion or distal movement of the distal tip of the optical fiber 152 into the lumen 116 beyond the firing position. As illustrated, the cooperating structure on the optical fiber 152 can include a tube 402 or other protrusion at least partially surrounding the jacket 160 of the optical fiber 152 and having a fixed position relative to the fiber tip 162. The cooperating structure on the sheath 110 can include a shoulder 404 formed in a portion of the shaft 112 by inserting a distal end of the shaft 112 into the distal tip portion 114 to create a narrowed portion of the lumen 116 which tapers in the distal direction toward the distal tip portion 114. The outer diameter of the shaft 112 proximal of the shoulder 404 can be approximately equal to the outer diameter of the distal tip portion 114, which can optionally be approximately 1.75 mm. The wall of the shaft 112 can optionally be approximately 0.005 mm thick.

Figure 21A:
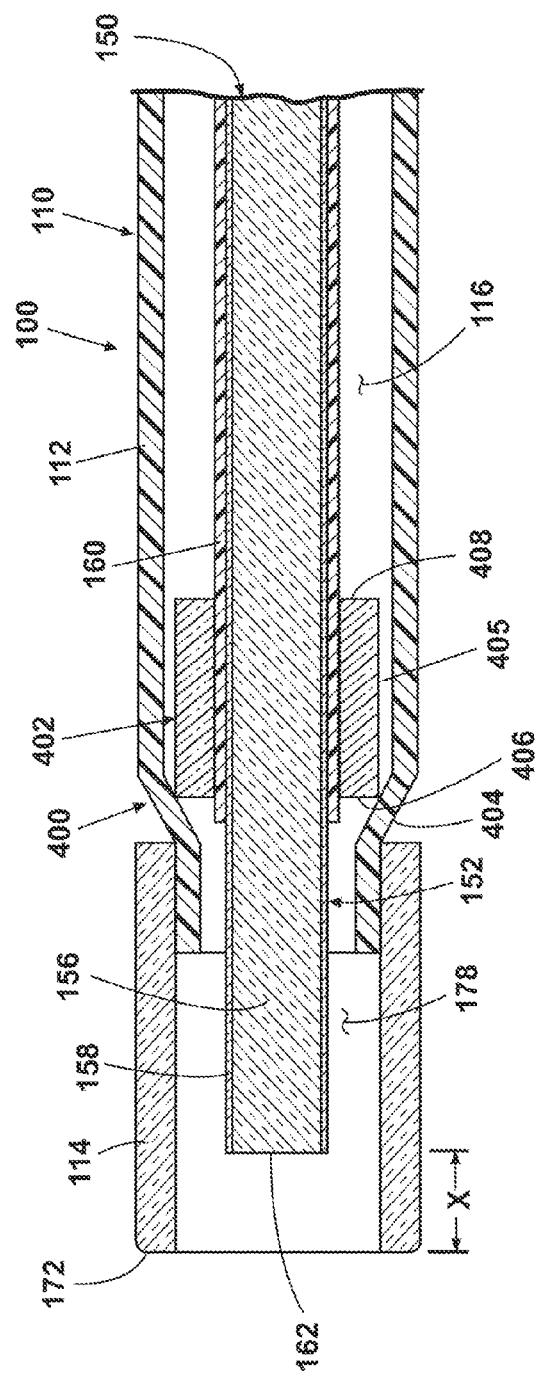
FIG. 21A is a side sectional view of a distal portion of another embodiment of the light delivery device comprising a position limiter.
Figure 21B:
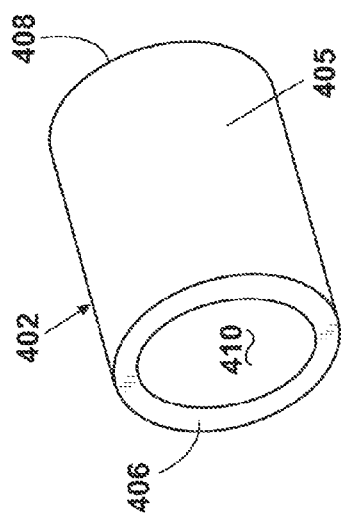
FIG. 21B is a perspective view of a portion of the position limiter of FIG. 21A.

In the embodiment of FIGS. 21A and 21B, the tube 402 comprises an open-ended hollow cylinder having an annular sidewall 405 with a distal face 406, a proximal face 408, and a channel 410 extending between the distal and proximal faces 406, 408. The tube 402 is mounted to the optical fiber 152 with the optical fiber 152 extending through the channel 410 and the fiber tip 162 spaced a predetermined distance from the distal face 406 selected such that upon insertion of the optical fiber 152 into the lumen 116, the distal face 406 will cooperate with the shoulder 404 to prevent movement of the fiber tip 162 beyond the predetermined firing position. The distal face 406 can optionally be located within 10-20 mm of the fiber tip 162, or 12 mm from the fiber tip 162.

In the embodiment of FIGS. 22A-22C, the tube 402 comprises an open-ended hollow cylinder similar to the tube 402 of FIGS. 21A and 21B, with the exception that the sidewall 405 comprises one or more recesses 412 formed adjacent the distal face 406. The recesses 412 provide flow passages that permit the passage of liquid from a liquid source, for example, liquid source 300 (FIGS. 4A and 4B) distally past the junction of the cooperating structures 402, 404 and into the fluid delivery space 178. The size of the recesses 412 can be selected to provide a fixed and predetermined liquid flow rate so that the tube 402 (or the cooperating structures 402, 404) function(s) as a liquid flow regulator in addition to a position limiter or stop. In this case, the flow rate of fluid to the fluid delivery space 178 can be controlled without the need for or use of a flow regulator (FIGS. 4B-4F) upstream of the sheath 112.

Figure 23A:
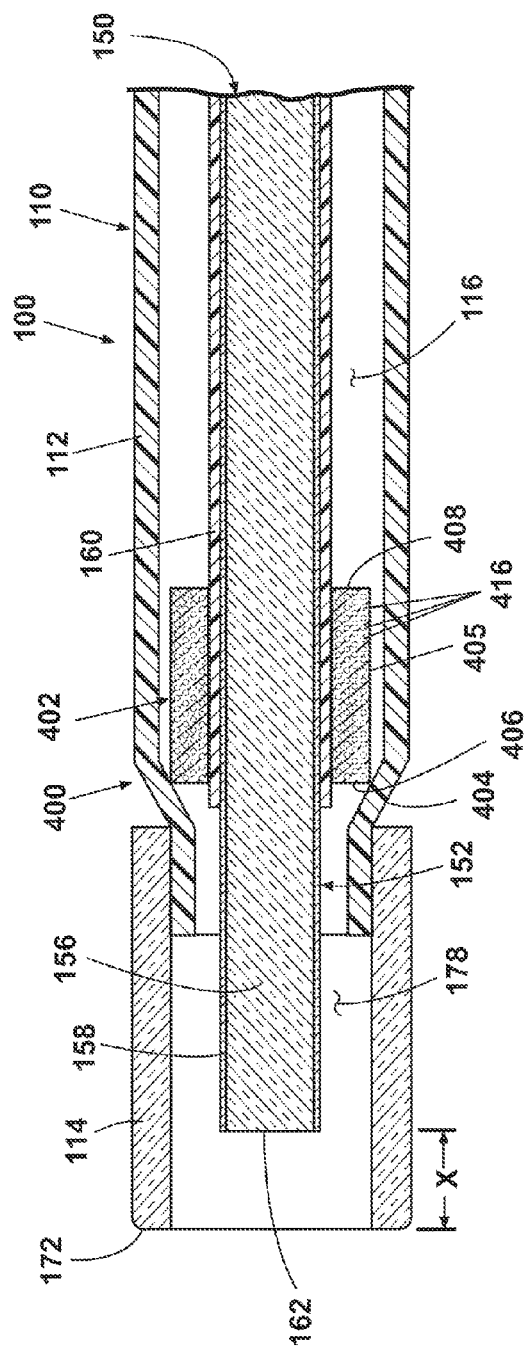
FIG. 23A is a side sectional view of a distal portion of another embodiment of the light delivery device comprising a position limiter.
Figure 23B:
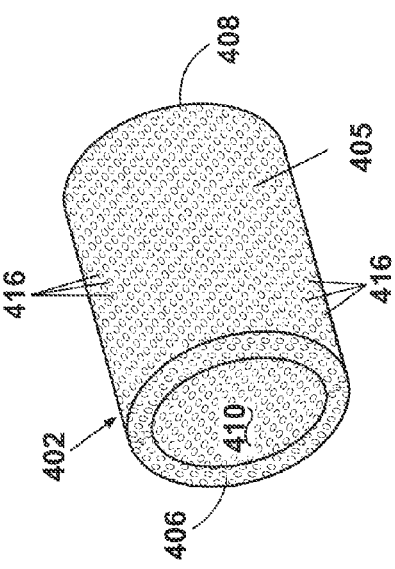
FIG. 23B is a perspective view of a portion of the position limiter of FIG. 23A.

In the embodiment of FIGS. 23A and 23B, the tube 402 comprises an open-ended hollow cylinder similar to the tube 402 of FIGS. 21A and 21B, with the exception that the tube 402 is fabricated from a porous material providing pores 416 through the tube 402 through which the liquid can flow. The pore size can be selected to provide a fixed and predetermined liquid flow rate through the tube walls so that the porous tube 402 can function as both a liquid flow regulator and a position limiter or stop. In this case, the flow rate of fluid to the fluid delivery space 178 can be controlled without the use of or need for a flow regulator 340 (FIGS. 4B-4F) upstream of the sheath 112. Suitable porous materials include ceramics and polymers such as UHMWPE, HDPE, LDPE, PP, PC, EVA, PVDF, and TPU. With this configuration, the fluid may enter the sidewall 405 or proximal face 408 and pass through the pores 416 to exit through the distal face 406. This configuration does not require the discrete flow paths through or around the tube 402 as found in the embodiment of FIGS. 22A-22C.

Figure 24A:
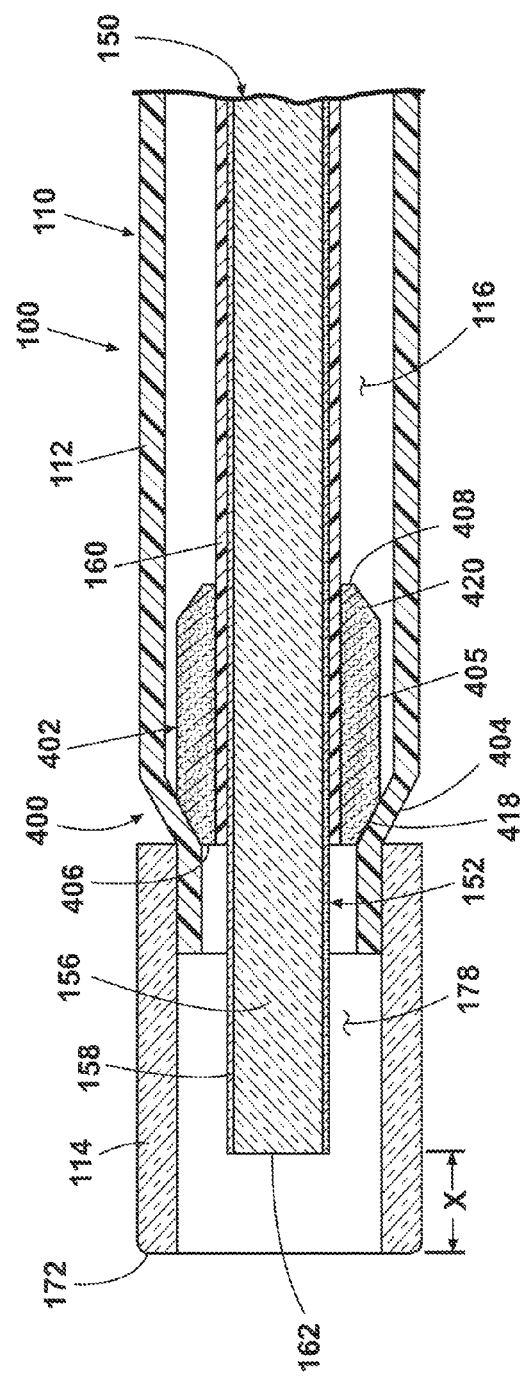
FIG. 24A is a side sectional view of a distal portion of another embodiment of the light delivery device comprising a position limiter.
Figure 24B:
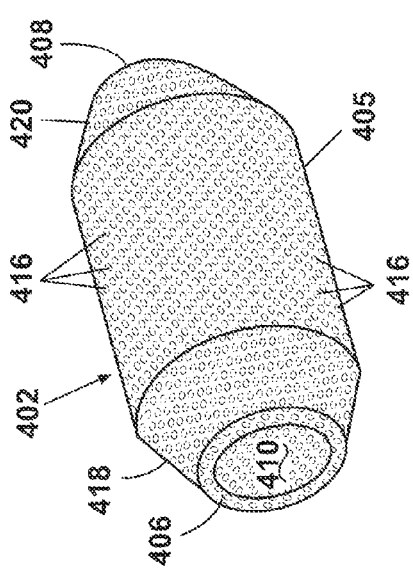
FIG. 24B is a perspective view of a portion of the position limiter of FIG. 24A.
Figure 26A:
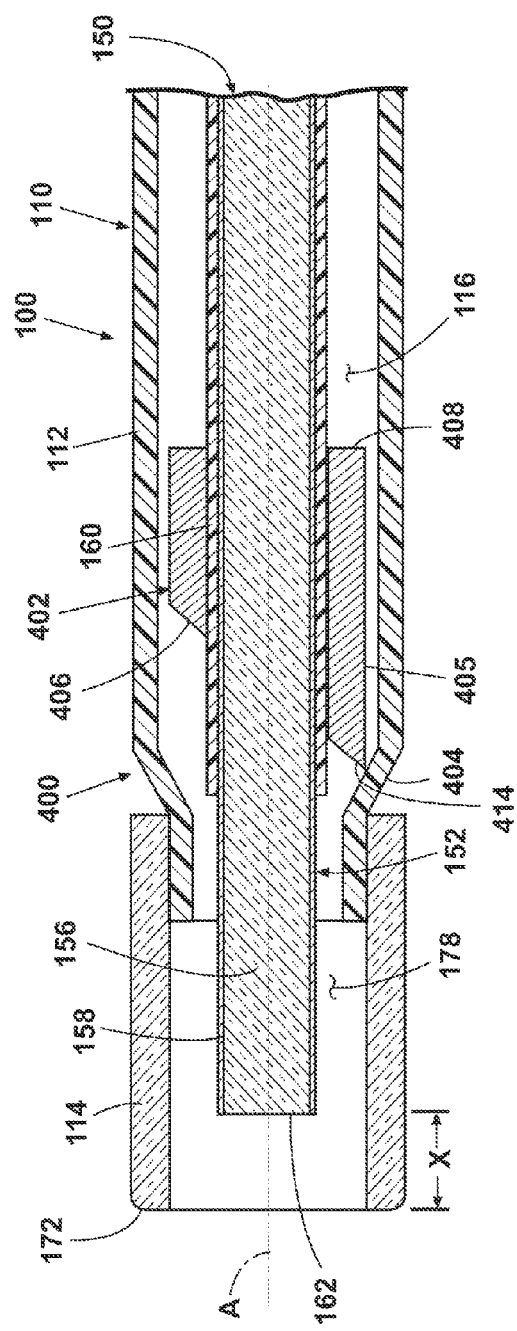
FIG. 26A is a side sectional view of a distal portion of another embodiment of the light delivery device comprising a position limiter.
Figure 26B:
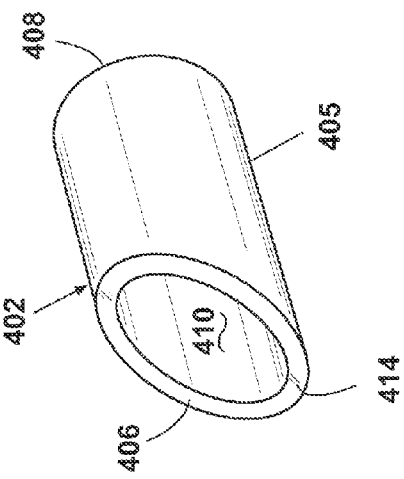
FIG. 26B is a perspective view of a portion of the position limiter of FIG. 26A.

In the embodiment of FIGS. 24A and 24B, the tube 402 is similar to the porous tube 402 of FIGS. 23A and 23B, with the exception that the sidewall 405 comprises a distal conical section 418 tapering toward the distal face 406 and a proximal conical section 420 tapering toward the proximal face 408. The taper of the distal conical section 418 can be generally complementary to the taper of the shoulder 404, as illustrated, so that the distal conical section 418 will match the shoulder 404 when the fiber tip 162 is in the predetermined firing position. With this configuration, the fluid may enter the sidewall 405, proximal face 408, or proximal conical section 420 and pass through the pores 416 to exit through the distal face 406. Alternately, if the taper of the distal conical section 418 is not complementary to the taper of the should 404, fluid may also exit through the distal conical section 418. Either configuration does not require the discrete flow paths through or around the tube 402 as found in the embodiment of FIGS. 22A-22C. The tube 402 can optionally be approximately 5 mm long, with an outer diameter of 1.2 mm. The channel 410 can optionally have an inner diameter of 0.8 mm.

In the embodiment of FIGS. 25A-25D, the tube 402 comprises an open-ended hollow cylinder similar to the tube 402 of FIGS. 21A and 21B, with the exception that the tube 402 comprises two angled faces 422 cut through the distal face 406 and the sidewall 405 at an angle with respect to the longitudinal axis A of the optical fiber 152. The angled faces 422 form two spaces 424 that permit the passage of liquid from a liquid source, for example, liquid source 300 (FIGS. 4A and 4B) between the angled faces 422 distally past the junction of the cooperating structures 402, 404 and into the fluid delivery space 178. The size of the spaces 424 can be selected to provide a fixed and predetermined flow rate so that the tube 402 (or the cooperating structures 402, 404) can function as both a liquid flow regulator and a position limiter or stop. In this case, the flow rate of fluid to the fluid delivery space 178 can be controlled without the need for or use of a flow regulator (FIGS. 4B-4F) upstream of the sheath 110. The size of the spaces 424 can be selected by changing the angle of the angled faces 422 with respect to the longitudinal axis A. The tube 402 can optionally have an outer diameter of 1.2 mm and an inner diameter of 0.85 mm. The angled face 422 can optionally extend approximately 3 mm proximally from the distal face 406 and be formed at an angle of 30-45 degrees to the longitudinal axis A.

In the embodiment of FIGS. 26A-26D, the tube 402 comprises an open-ended hollow cylinder similar to the tube 402 of FIGS. 21A and 21B, with the exception that the distal face 406 formed at an angle with respect to the longitudinal axis A of the optical fiber 152. The angled distal face 406 comprises a distal-most tip 414 that will cooperate with the shoulder 404 to prevent movement of the fiber tip 162 beyond the predetermined firing position. The angled distal face 406 recedes proximally from the distal-most tip 414 to provide a space between the angled distal face 406 and the shoulder 404 that permits the passage of liquid from a liquid source, for example, liquid source 300 (FIGS. 4A and 4B) into the fluid delivery space 178. The tube 402 can optionally have an outer diameter of 1.2 mm and an inner diameter of 0.85 mm. The angled distal face 406 can optionally extend approximately 3 mm along the longitudinally axis A and be formed at an angle of 20-45 degrees to the longitudinal axis A.

While the embodiments of FIGS. 21A-26D illustrate various position limiters 400 comprising tubes 402 cooperating with a portion of the shaft 112 to limit the position of the fiber tip 162, it is also understood that the distal tip portion 114 can be configured to cooperate with the tubes 402 of FIGS. 21A-26D to limit the position of the fiber tip 162. In the embodiment of FIG. 27, the cooperating structure on the optical fiber 152 comprises the open-ended tube 402 of FIGS. 21A and 21B, although any of the tubes 402 shown herein could be used, and the cooperating structure on the sheath 110 comprises a shoulder 426 formed in the distal tip portion 114 that creates a narrowed portion of the lumen 116 which tapers in the distal direction toward the distal end 172. The distal face 406 of the tube 402 will cooperate with the shoulder 426 to prevent movement of the fiber tip 162 beyond the predetermined firing position.

In the embodiment of FIG. 28, the cooperating structure on the optical fiber 152 comprises the open-ended tube 402 of FIGS. 21A and 21B, although any of the tubes 402 shown herein could be used, and the cooperating structure on the sheath 100 comprises a proximal face 428 of the distal tip portion 114. The distal face 406 of the tube 402 will cooperate with the proximal face 428 of the distal tip portion 114 to prevent movement of the fiber tip 162 beyond the predetermined firing position.

Additional embodiments comprise methods of sterilization. Certain such methods can comprise sterilizing, either terminally or sub-terminally, any of the apparatus disclosed herein that are intended for insertion into (or other contact with) the patient or that are intended for use at or near the surgical field during treatment of a patient. Any suitable method of sterilization, whether presently known or later developed, can be employed.

Accordingly, certain methods comprise sterilizing, either terminally or sub-terminally, any of the embodiments of the system 100 or any of the components or subsystems thereof disclosed herein, including but not limited to any of the embodiments of the sheath 110 or light delivery device 150 disclosed herein. Any suitable method of sterilization, whether presently known or later developed, can be employed. For example, the method can comprise sterilizing any of the above-listed apparatus with an effective dose of a sterilant such as cyclodextrin (Cidex(™)), ethylene oxide (EtO), steam, hydrogen peroxide vapor, electron beam (E-beam), gamma irradiation, x-rays, or any combination of these sterilants.

The sterilization methods can be performed on the apparatus in question while the apparatus is partially or completely assembled (or partially or completely disassembled); thus, the methods can further comprise partially or completely assembling (or partially or completely disassembling) the apparatus before applying a dose of the selected sterilant(s). The sterilization methods can also optionally comprise applying one or more biological or chemical indicators to the apparatus before exposing the apparatus to the sterilant(s), and assessing mortality or reaction state of the indicator(s) after exposure. As a further option, the sterilization methods can involve monitoring relevant parameters in a sterilization chamber containing the apparatus, such as sterilant concentration, relative humidity, pressure, and/or apparatus temperature.

In view of the foregoing discussion of methods of sterilization, further embodiments comprise sterile apparatus. Sterile apparatus can comprise any of the apparatus disclosed herein that are intended for insertion into (or other contact with) the patient or that are intended for use at or near the surgical field during treatment of a patient. More specifically, any one or combination of the following can be provided as a sterile apparatus: any of the embodiments of the system 100 or any of the components or subsystems thereof disclosed herein, including but not limited to any of the embodiments of the sheath 110 or light delivery device 150 disclosed herein.

While certain embodiments have been described, these embodiments have been presented by way of example only, and are not intended to limit the scope of the disclosure or of the patent protection sought in connection with this specification. Indeed, the novel methods and systems described herein may be embodied in a variety of other forms; furthermore, various omissions, substitutions and changes in the form of the methods and systems described herein may be made without departing from the spirit of the disclosure.

What is claimed is:

1. Apparatus for treating a hollow anatomical structure, the apparatus comprising:
   a sheath, the sheath having an elongate shaft defining an internal lumen, the shaft having a sidewall, a proximal portion, and a distal portion, the sidewall being more transmissive of therapeutic light energy in the distal portion than in the proximal portion, the distal portion forming a distal tip of the shaft and having a distal-facing opening at the distal tip;
   an optical fiber disposed within and movable along the lumen, the optical fiber having a fiber tip;
   a light propagation path which extends distally from the fiber tip and through the distal-facing opening; and
   a position limiter configured to limit distal movement of the fiber tip relative to the distal tip of the shaft such that the fiber tip cannot extend distally farther than 2 mm proximal of the distal tip of the shaft, the position limiter comprising a narrowed portion of the lumen in the distal portion of the shaft, the narrowed portion forming a shoulder, and a structure on the optical fiber configured to abut the shoulder;
   wherein the position limiter comprises a tube at least partially surrounding the optical fiber, and the tube includes at least one tab and at least one recess in a distal face thereof.

2. The apparatus according to claim 1, wherein the sidewall is made from a first material in the proximal portion and from a second material in the distal portion, the second material being more transmissive of therapeutic light than the first material.

3. The apparatus according to claim 2, wherein the second material is transmissive of wavelengths of light from 800 to 1500 nm.

4. The apparatus according to claim 2, wherein the first material is more flexible than the second material.

5. The apparatus according to claim 2, wherein the second material is one of quartz, sapphire, synthetic fused silica, polycarbonate, polyetheretherketone, polysufone, polyarylethersulfone, polyetherimide, and polyamide-imide.

6. The apparatus according to claim 1, wherein the shaft is sized for insertion into a vein.

7. The apparatus according to claim 1 further comprising a liquid flow advancing distally along the shaft lumen and contacting the fiber tip.

8. The apparatus according to claim 7 further comprising a liquid source in fluid communication with the shaft lumen, the liquid source configured to provide the liquid flow at a fixed and predetermined liquid flow rate.

9. The apparatus according to claim 8, wherein the liquid flow rate is 5-60cc/hr.

10. The apparatus according to claim 8, wherein the liquid source comprises a saline bag fluidly coupled to the shaft lumen through a flow regulator.

11. The apparatus according to claim 8, wherein the liquid source comprises a liquid reservoir, a liquid flow path from the reservoir to the shaft lumen, and a flow restriction comprising an orifice of a fixed size positioned in the flow path, the orifice size being smaller than that of the rest of the liquid flow path.

12. The apparatus according to claim 1, wherein the fiber tip is optically coupled to the distal-facing opening to form the light propagation path.

13. The apparatus according to claim 1, wherein the narrowed portion of the lumen in the distal portion of the shaft tapers in the distal direction toward the distal tip of the shaft.

14. Apparatus for treating a hollow anatomical structure, the apparatus comprising:
   a sheath, the sheath having an elongate shaft defining an internal lumen, the shaft having a sidewall, a proximal portion, and a distal portion, the sidewall being more transmissive of therapeutic light energy in the distal portion than in the proximal portion, the distal portion forming a distal tip of the shaft and having a distal-facing opening at the distal tip;
   an optical fiber disposed within and movable along the lumen, the optical fiber having a fiber tip;
   a light propagation path which extends distally from the fiber tip and through the distal-facing opening; and
   a position limiter configured to limit distal movement of the fiber tip relative to the distal tip of the shaft such that the fiber tip cannot extend distally farther than 2 mm proximal of the distal tip of the shaft, the position limiter comprising a narrowed portion of the lumen in the distal portion of the shaft, the narrowed portion forming a shoulder, and a structure on the optical fiber configured to abut the shoulder;
   wherein the position limiter comprises a tube at least partially surrounding the optical fiber, and the tube includes a plurality of pores configured to allow a predetermined positive liquid flow rate through the tube.

15. The apparatus according to claim 14, wherein the shaft is sized for insertion into a vein.

16. The apparatus according to claim 14, wherein the sidewall is made from a first material in the proximal portion and from a second material in the distal portion, the second material being more transmissive of therapeutic light than the first material.

17. The apparatus according to claim 16, wherein the second material is transmissive of wavelengths of light from 800 to 1500 nm.

18. The apparatus according to claim 16, wherein the first material is more flexible than the second material.

19. The apparatus according to claim 16, wherein the second material is one of quartz, sapphire, synthetic fused silica, polycarbonate, polyetheretherketone, polysufone, polyarylethersulfone, polyetherimide, and polyamide-imide.

20. The apparatus according to claim 14 further comprising a liquid flow advancing distally along the shaft lumen and contacting the fiber tip.

21. The apparatus according to claim 20 further comprising a liquid source in fluid communication with the shaft lumen, the liquid source configured to provide the liquid flow at a fixed and predetermined liquid flow rate.

22. The apparatus according to claim 21, wherein the liquid flow rate is 5-60 cc/hr.

23. The apparatus according to claim 21, wherein the liquid source comprises a saline bag fluidly coupled to the shaft lumen through a flow regulator.

24. The apparatus according to claim 21, wherein the liquid source comprises a liquid reservoir, a liquid flow path from the reservoir to the shaft lumen, and a flow restriction comprising an orifice of a fixed size positioned in the flow path, the orifice size being smaller than that of the rest of the liquid flow path.

25. The apparatus according to claim 14, wherein the fiber tip is optically coupled to the distal-facing opening to form the light propagation path.

26. The apparatus according to claim 14, wherein the narrowed portion of the lumen in the distal portion of the shaft tapers in the distal direction toward the distal tip of the shaft.

* * * * *